(12) United States Patent
Brünjes et al.

(10) Patent No.: US 9,078,440 B2
(45) Date of Patent: Jul. 14, 2015

(54) 6-(2-AMINOPHENYL)PICOLINATES AND THEIR USE AS HERBICIDES

(75) Inventors: Marco Brünjes, Hofheim (DE); Uwe Döller, Rodgau (DE); Hansjörg Dietrich, Liederbach am Taunus (DE); Michael Gerhard Hoffmann, Flörsheim (DE); Isolde Häuser-Hahn, Leverkusen (DE); Christopher Hugh Rosinger, Hofheim am Taunus (DE); Elmar Gatzweiler, Bad Nauheim (DE); Ines Heinemann, Hofheim (DE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 64 days.

(21) Appl. No.: 13/994,557

(22) PCT Filed: Dec. 12, 2011

(86) PCT No.: PCT/EP2011/072483
§ 371 (c)(1),
(2), (4) Date: Aug. 20, 2013

(87) PCT Pub. No.: WO2012/080187
PCT Pub. Date: Jun. 21, 2012

(65) Prior Publication Data
US 2013/0326735 A1    Dec. 5, 2013

Related U.S. Application Data

(60) Provisional application No. 61/424,299, filed on Dec. 17, 2010.

(51) Int. Cl.
*A01N 43/40* (2006.01)
*C07D 213/79* (2006.01)

(52) U.S. Cl.
CPC .............. *A01N 43/40* (2013.01); *C07D 213/79* (2013.01)

(58) Field of Classification Search
USPC .......... 504/100, 244, 260; 514/277, 352, 354; 546/304, 309, 310; 560/48, 102; 562/405, 426, 432, 433
See application file for complete search history.

(56) References Cited

U.S. PATENT DOCUMENTS

| | | | |
|---|---|---|---|
| 7,314,849 B2 * | 1/2008 | Balko et al. .................... | 504/244 |
| 8,003,799 B2 * | 8/2011 | Nieto-Roman et al. ...... | 546/309 |
| 8,536,331 B2 * | 9/2013 | Eckelbarger et al. ......... | 544/329 |
| 2010/0137137 A1 * | 6/2010 | Rosinger et al. .............. | 504/105 |

FOREIGN PATENT DOCUMENTS

| | | |
|---|---|---|
| WO | 200151468 A1 | 7/2001 |
| WO | 2003011853 A1 | 2/2003 |
| WO | 2006062979 A1 | 6/2006 |
| WO | 2007082098 A2 | 7/2007 |
| WO | 2007092184 A2 | 8/2007 |
| WO | 2009046090 A1 | 4/2009 |
| WO | 2009138712 A2 | 11/2009 |
| WO | 2010060581 A2 | 6/2010 |
| WO | 2010099279 A1 | 9/2010 |

OTHER PUBLICATIONS

International Search Report for PCT/EP2011/072483 Mailed March 9, 2012.

* cited by examiner

*Primary Examiner* — Jane C Oswecki
(74) *Attorney, Agent, or Firm* — Miles and Stockbridge

(57) ABSTRACT

The present invention relates to novel herbicidally active 6-(2-aminophenyl)picoline derivatives and to processes for preparation thereof. The present invention further provides for the use thereof as a herbicide, especially as a herbicide for selective control of weed plants in useful plant crops, and as a plant growth regulator alone or in combination with safeners and/or in a mixture with other herbicides.

12 Claims, No Drawings

6-(2-AMINOPHENYL)PICOLINATES AND THEIR USE AS HERBICIDES

CROSS REFERENCE TO RELATED APPLICATIONS

This application is a §371 National Stage Application of PCT/EP2011/072483, filed Dec. 12, 2011, which claims priority to European Application No. 10195356.0, filed Dec. 16, 2010, and U.S. Provisional Application No. 61/424,299, filed Dec. 17, 2010.

BACKGROUND OF THE INVENTION

1. Field of the Invention

The present invention relates to novel herbicidally active 6-(2-aminophenyl)picoline derivatives and to processes for preparation thereof. The present invention further provides for the use thereof as a herbicide, especially as a herbicide for selective control of weed plants in useful plant crops, and as a plant growth regulator alone or in combination with safeners and/or in a mixture with other herbicides.

2. Description of Related Art

It is known from various documents that similarly substituted picoline derivatives have herbicidal and/or pesticidal properties:

WO 2001/51468 and WO 2006/062979 describe herbicidally active derivatives of picolinic acids. In contrast to the present invention, however, these compounds do not bear a phenyl substituent in the 6 position.

WO 2003/011853, WO 2007/082098, WO 2007/092184 and WO 2009/046090 likewise describe herbicidally active, differently substituted 6-phenylpicolinates. In contrast to the present invention, however, these documents do not disclose any 6-(2-aminophenyl)-substituted picolinates.

WO 2010/099279 discloses exclusively N-alkoxyamide derivatives of 6-phenyl-substituted picolinic acids. The prior art, however, does not disclose any 6-(2-aminophenyl)-substituted picolinic acid derivatives.

WO 2010/060581 discloses 6-phenylpicolinates and the use thereof as herbicides.

In contrast to the present invention, accordingly, none of the documents cited describes picolinic acids or picolinic esters which have an unsubstituted amino group in the 2 position on the aryl substituent.

The active ingredients known from the documents cited above have disadvantages in use, for example that they have (a) zero or else only inadequate herbicidal action against weed plants, (b) too narrow a spectrum of weed plants controlled, or (c) too low a selectivity in useful plant crops.

It is therefore desirable to provide chemical active ingredients which can be used with advantages as herbicides or plant growth regulators.

SUMMARY

It has now been found that, surprisingly, particular substituted 6-(2-aminophenyl)picoline derivatives have good herbicidal action and at the same time increased compatibility with respect to useful plants. The present invention therefore further provides compounds of the formula (I), and the N-oxides, salts and agrochemically suitable derivatives thereof,

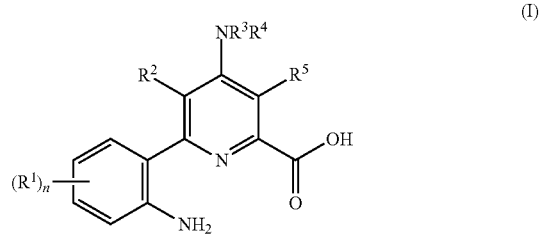

in which the radicals are each defined as follows:

n is an integer selected from 0, 1, 2, 3, 4;

$R^1$ is selected from the group consisting of hydrogen, halogen, cyano, nitro, amino, hydroxyl, $(C_1-C_6)$alkyl, $(C_1-C_6)$haloalkyl, $(C_1-C_4)$hydroxyalkyl, $(C_2-C_6)$alkoxyalkyl, $(C_2-C_6)$haloalkoxyalkyl, $(C_2-C_6)$alkenyl, $(C_2-C_6)$haloalkenyl, $(C_2-C_6)$alkynyl, $(C_3-C_6)$haloalkynyl, $(C_1-C_6)$alkoxy, $(C_1-C_6)$haloalkoxy, $(C_2-C_6)$alkenyloxy, $(C_2-C_6)$haloalkenyloxy, $(C_2-C_6)$alkynyloxy, $(C_3-C_6)$haloalkynyloxy, $(C_1-C_6)$alkylthio, $(C_2-C_6)$alkylthioalkyl, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, $(C_2-C_6)$alkenylthio, $(C_2-C_6)$haloalkenylthio, $(C_2-C_6)$alkenylsulfinyl, $(C_2-C_6)$haloalkenylsulfinyl, $(C_2-C_6)$alkenylsulfonyl, $(C_2-C_6)$haloalkenylsulfonyl, $(C_2-C_6)$alkynylthio, $(C_3-C_6)$haloalkynylthio, $(C_3-C_6)$alkynylsulfinyl, $(C_3-C_6)$haloalkynylsulfinyl, $(C_3-C_6)$alkynylsulfonyl, $(C_3-C_6)$haloalkynylsulfonyl, $(C_1-C_6)$alkylamino, $(C_2-C_6)$dialkylamino, $(C_2-C_6)$alkylaminoalkyl, $(C_2-C_6)$alkylcarbonyl, $(C_2-C_6)$alkoxycarbonyl, $(C_2-C_6)$aminocarbonyl, $(C_2-C_6)$alkylaminocarbonyl, $(C_3-C_8)$dialkylaminocarbonyl, $(C_3-C_6)$trialkylsilyl, phenyl, phenoxy and 5- or 6-membered heteroaromatic rings, where each phenyl ring, phenoxy ring or 5- or 6-membered heteroaromatic ring may optionally be substituted by 1-3 $R^{25}$ radicals; or where two adjacent $R^1$ radicals may together form an —OCH$_2$O—, —CH$_2$CH$_2$O—, —OCH$_2$CH$_2$O—, —OCH(CH$_3$)O—, —OC(CH$_3$)$_2$O—, —OCF$_2$O—, —CF$_2$CF$_2$O—, —OCF$_2$CF$_2$O— or —CH═CH—CH═CH— group;

$R^2$ is hydrogen, halogen, cyano, nitro, $(C_1-C_6)$alkyl, $(C_1-C_6)$haloalkyl, $(C_1-C_6)$alkoxy, $(C_1-C_6)$alkylamino, $(C_1-C_6)$dialkylamino, $(C_1-C_6)$thioalkoxy, $(C_2-C_6)$alkenyl, $(C_2-C_6)$haloalkenyl, $(C_2-C_6)$alkynyl;

$R^3$ is hydrogen, $(C_1-C_4)$alkyl optionally substituted by one or two $R^6$ radicals, $(C_2-C_4)$alkenyl optionally substituted by 1-2 $R^7$ radicals, or $(C_2-C_4)$alkynyl optionally substituted by one or two $R^8$ radicals; or $R^3$ is C(═O)R$^9$, NO$_2$, OR$^{10}$, S(O)$_2$R$^{11}$, N(R$^{12}$)R$^{13}$ or N═C(R$^{14}$)R$^{15}$;

$R^4$ is hydrogen, $(C_1-C_4)$alkyl optionally substituted by one or two $R^6$ radicals, or C(═O)R$^9$; or $R^3$ and $R^4$ together form a —(CH$_2$)$_4$—, —(CH$_2$)$_5$—, —CH$_2$CH═CHCH$_2$— or —(CH$_2$)$_2$O(CH$_2$)$_2$— group optionally substituted by one or two $R^{16}$ radicals; or $R^3$ and $R^4$ together form a ═C(R$^{17}$)N(R$^{18}$)R$^{19}$ or ═C(R$^{20}$)OR$^{21}$ group;

where each $R^6$, $R^7$ and $R^8$ radical is independently selected from halogen, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino and $(C_2-C_4)$alkoxycarbonyl;

$R^5$ is hydrogen, halogen, cyano, nitro, formyl, $(C_1-C_6)$alkyl, $(C_2-C_6)$alkenyl, $(C_2-C_6)$alkynyl, $(C_1-C_6)$haloalkyl, $(C_2-C_6)$haloalkenyl, $(C_1-C_6)$alkoxy, $(C_1-C_6)$thioalkoxy, $(C_2-C_6)$alkoxyalkyl, $(C_2-C_6)$thioalkoxyalkyl;

$R^9$ is hydrogen, $(C_1-C_4)$alkyl, $(C_1-C_4)$haloalkyl, $(C_1-C_4)$alkoxy, phenyl, phenoxy, benzyl or benzyloxy;

$R^{10}$ is hydrogen, $(C_1-C_4)$alkyl, $(C_1-C_3)$haloalkyl or $CHR^{22}C(O)OR^{23}$;

$R^{11}$ is $(C_1-C_4)$alkyl, $(C_1-C_4)$haloalkyl or phenyl optionally substituted by one, two or three radicals selected independently from $CH_3$, Cl and $OCH_3$;

$R^{12}$ is hydrogen, $(C_1-C_4)$alkyl or $C(=O)R^{24}$;

$R^{13}$ is hydrogen or $(C_1-C_4)$alkyl;

$R^{14}$ is hydrogen, $(C_1-C_4)$alkyl or phenyl optionally substituted by one, two or three radicals selected independently from $CH_3$, Cl or $OCH_3$;

$R^{15}$ is hydrogen or $(C_1-C_4)$alkyl; or $R^{14}$ and $R^{15}$ together form a $—(CH_2)_4—$ or $—(CH_2)_5—$ group;

$R^{16}$ is independently halogen, $(C_1-C_3)$alkyl, $(C_1-C_3)$alkoxy, $(C_1-C_3)$haloalkoxy, $(C_1-C_3)$alkylthio, $(C_1-C_3)$haloalkylthio, amino, $(C_1-C_3)$alkylamino, $(C_2-C_4)$dialkylamino or $(C_2-C_4)$alkoxycarbonyl;

$R^{17}$ is hydrogen or $(C_1-C_4)$alkyl;

$R^{18}$ and $R^{19}$ are each independently selected from hydrogen and $(C_1-C_4)$alkyl; or $R^{18}$ and $R^{19}$ together form a $—(CH_2)_4—$, $—(CH_2)_5—$, $—CH_2CH=CHCH_2—$ or $—(CH_2)_2O(CH_2)_2—$ group;

$R^{20}$ is hydrogen or $(C_1-C_4)$alkyl;

$R^{21}$ ist $(C_1-C_4)$alkyl;

$R^{22}$ is hydrogen, $(C_1-C_4)$alkyl, $(C_1-C_3)$haloalkyl, $(C_1-C_4)$alkoxy, phenyl, phenoxy or benzyloxy;

$R^{23}$ is hydrogen, $(C_1-C_4)$alkyl or $(C_1-C_4)$alkoxy;

$R^{24}$ is hydrogen, $C_1-C_4$ alkyl or benzyl; and $R^{25}$ is independently halogen, cyano, nitro, $(C_1-C_6)$alkyl, $(C_1-C_6)$haloalkyl, $(C_2-C_4)$alkenyl, $(C_2-C_4)$haloalkenyl, $(C_3-C_4)$alkynyl, $(C_3-C_4)$haloalkynyl, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$alkylsulfonyl, $(C_1-C_4)$alkylamino, $(C_2-C_8)$dialkylamino, $(C_2-C_4)$alkylcarbonyl, $(C_2-C_6)$alkoxycarbonyl, $(C_2-C_6)$alkylaminocarbonyl, $(C_3-C_8)$dialkylaminocarbonyl or $(C_3-C_6)$trialkylsilyl.

In the radicals mentioned, the total number of carbon atoms is always reported; for example, a dimethylaminocarbonyl radical is a $C_3$ radical.

DETAILED DESCRIPTION OF A PREFERRED EMBODIMENT

The expression "agrochemically suitable derivatives", which is used to describe the inventive variations of the carboxylic acid function in the 2 position, refers to any esters, acyl hydrazides, imidates, thioimidates, amidines, amides, orthoesters, acyl cyanides, acyl halides, thioesters, thionoesters, dithiol esters, nitriles or other carboxylic acid derivatives known in the prior art which (a) do not significantly impair the herbicidal activity of the active ingredients and (b) are or can be hydrolyzed, oxidized or metabolized in the plant or in the soil to the picolinic acids of the formula (I), which are present in dissociated or undissociated form as a function of the pH.

Preferred agrochemically suitable derivatives of the picolinic acids of the formula (I) are therefore salts, amides and esters.

Equally, the expression "agrochemically suitable derivatives", with regard to the amino groups present, also describes any silylamines, phosphorylamines, phosphinimines, phosphoramidates, sulfonamides, sulfilimides, sulfoximines, aminals, hemiaminals, amides, thioamides, carbamates, thiocarbamates, amidines, ureas, imines, nitro, nitroso, azido or other nitrogen-containing derivatives which are described in the prior art and (a) do not significantly impair the herbicidal activity of the active ingredients and (b) are or can be hydrolyzed, oxidized or metabolized in the plant or in the soil to the free amines of the formula (I), which are present in dissociated or undissociated form as a function of the pH.

Preferred agrochemically suitable derivatives with regard to the amino groups are therefore salts, amides, sulfonamides and carbamates.

Agrochemically suitable derivatives, esters and salts preferred in the context of the present invention are represented by the formulae (I-a) to (I-c).

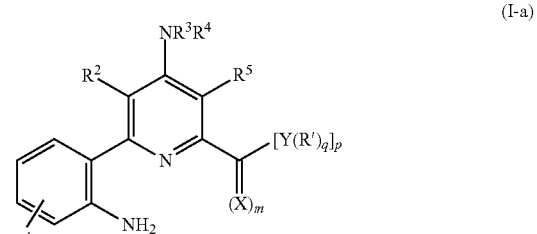

(I-a)

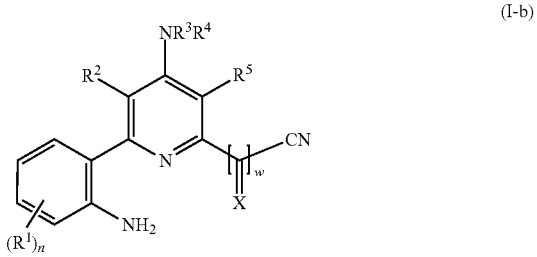

(I-b)

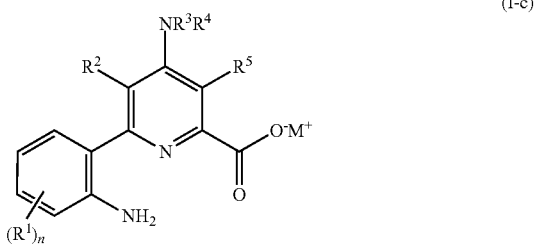

(I-c)

In formula (I-a), the radicals are each defined as follows:

X is selected from O, S, NH and NR" where R" is a $(C_1-C_4)$alkyl group;

m is 0 or 1;

Y is selected from halogen, O, S and N;

q is 0, 1 or 2;

p is 1, 2 or 3;

R' is selected from hydrogen, halogen, $(C_1-C_4)$alkyl, $(C_1-C_4)$haloalkyl, $(C_2-C_4)$alkoxyalkyl, $(C_2-C_4)$alkylthioalkyl, $(C_2-C_4)$alkenyl, oxiranyl, $(C_1-C_4)$alkyloxiranyl, oxiranyl-$(C_1-C_4)$alkyl, $(C_2-C_4)$haloalkenyl, 2-halooxiranyl, 3-halooxiranyl, 2,3-dihalooxiranyl, $(C_3-C_6)$alkoxyalkenyl, $(C_3-C_6)$alkylthioalkenyl, $(C_2-C_4)$alkynyl, $(C_2-C_4)$haloalkynyl, formyl, $(C_2-C_4)$alkylcarbonyl, $(C_2-C_4)$haloalkylcarbonyl, $(C_1-C_4)$alkoxy, $(C_1-C_4)$haloalkoxy, $(C_1-C_4)$alkylthio, $(C_1-C_4)$haloalkylthio, hydroxyl and $NH_2$;

where the remaining radicals are as defined below;

the radicals in formula (I-b) are each defined as follows:

X is selected from O and S;

Q is 0 or 1;

where the remaining radicals are each as defined below;

M+ in formula (I-c) is defined as a cation, particular preference being given to the sodium, potassium and ammonium salts of the inventive compounds of the formula (I).

The remaining radicals the definitions given below have. For instance, formula (I-a)

where X=O, m=1, Y=O, R'=($C_1$-$C_4$)alkyl, q=1, p=1 represents the corresponding esters of the inventive compounds of the formula (I);

where X=O, m=1, Y=NH, R'=$NH_2$, q=1, p=1 represents the corresponding acyl hydrazides of the inventive compounds of the formula (I);

where X=NH or NR'', m=1, Y=O, R'=H or ($C_1$-$C_4$)alkyl, q=1, p=1 represents the corresponding imidates of the inventive compounds of the formula (I);

where X=NH or NR'', m=1, Y=S, R'=H or ($C_1$-$C_4$)alkyl, q=1, p=1 represents the corresponding thioimidates of the inventive compounds of the formula (I);

where X=NH or NR'', m=1, Y=N, R'=H or ($C_1$-$C_4$)alkyl, q=2, p=1 represents the corresponding amidines of the inventive compounds of the formula (I);

where X=O, m=1, Y=N, R'=H or ($C_1$-$C_4$)alkyl, q=2, p=1 represents the corresponding amides of the inventive compounds of the formula (I);

where m=0, Y=O, R'=($C_1$-$C_4$)alkyl, q=1, p=3 represents the corresponding ortho esters of the inventive compounds of the formula (I);

where X=O, m=1, Y=S, R'=H or ($C_1$-$C_4$)alkyl, q=1, p=1 represents the corresponding thioesters of the inventive compounds of the formula (I);

where X=S, m=1, Y=O, R'=H or ($C_1$-$C_4$)alkyl, q=1, p=1 represents the corresponding thionoesters of the inventive compounds of the formula (I);

where X=S, m=1, Y=S, R'=H or ($C_1$-$C_4$)alkyl, q=1, p=1 represents the corresponding dithiol esters of the inventive compounds of the formula (I);

where X=O, m=1, Y=halogen, q=0, p=1 represents acyl halides of the inventive compounds of the formula (I);

where X=O, m=1, Y=N, R'=OH or ($C_1$-$C_4$)alkoxy, q=2, p=1 represents hydroxamic acids or alkoxy amides of the inventive compounds of the formula (I).

In addition, formula (I-b)

where X=O and w=1 represents the corresponding acyl cyanides, where w=0 represents the corresponding nitriles.

Formula (I-c) represents salt derivatives of the inventive compounds of the formula (I).

Salt formation can be effected in a known manner, for example by the action of a base on compounds of the formula (I). Suitable bases are, for example, organic amines such as trialkylamines, morpholine, piperidine or pyridine, and also ammonia, ammonium, alkali metal or alkaline earth metal hydroxides, ammonium, alkali metal or alkaline earth metal carbonates and ammonium, alkali metal or alkaline earth metal hydrogencarbonates, especially sodium and potassium hydroxide, sodium and potassium carbonate and sodium and potassium hydrogencarbonate. These salts are compounds in which the acidic hydrogen is replaced by a cation suitable for agriculture, for example metal salts, especially alkali metal salts or alkaline earth metal salts, especially sodium and potassium salts, or else salts with organic amines or ammonium salts, for example with ammonium ions of the formula [NRR'R''R''']+, in which R, R', R'' and R''' are each independently H or an organic radical, especially ($C_1$-$C_6$)alkyl, ($C_6$-$C_{10}$)aryl, ($C_7$-$C_{20}$)aralkyl or ($C_7$-$C_{20}$)alkylaryl. Examples are $[NH_4]^+$, $[NH_3CH_3]^+$, $[NH_2(CH_3)_2]^+$, $[NH(CH_3)_3]^+$, $[N(CH_3)_4]^+$, $[NH_2CH_3C_2H_5]^+$ or $[NH_2CH_3C_6H_5]^+$. Also useful are alkylsulfonium and alkylsulfoxonium salts, such as ($C_1$-$C_4$)-trialkylsulfonium and ($C_1$-$C_4$)-trialkylsulfoxonium salts.

Particular preference is given to the sodium, potassium and ammonium salts of the inventive compounds of the formula (I).

Preference is given to compounds of the formula (I) or to the N-oxides, salts and agrochemically suitable derivatives of the formulae (1-a), (1-b) and (1-c) thereof, in which the radicals are each defined as follows:

n is an integer selected from 0, 1, 2, 3, 4;

$R^1$ is independently selected from hydrogen, halogen, cyano, nitro, amino, ($C_1$-$C_6$)alkyl, ($C_1$-$C_6$)haloalkyl, ($C_2$-$C_6$)alkoxyalkyl, ($C_2$-$C_6$)haloalkoxyalkyl, ($C_2$-$C_6$)alkenyl, ($C_2$-$C_6$)haloalkenyl, ($C_2$-$C_6$)alkynyl, ($C_1$-$C_6$)alkoxy, ($C_1$-$C_6$)haloalkoxy, ($C_2$-$C_6$)haloalkenyloxy, ($C_1$-$C_6$)alkylthio, ($C_2$-$C_6$)alkylthioalkyl, ($C_1$-$C_6$)haloalkylthio, ($C_1$-$C_6$)alkylsulfonyl, ($C_1$-$C_6$)haloalkylsulfonyl, ($C_2$-$C_6$)alkenylthio, ($C_2$-$C_6$)haloalkenylthio, ($C_1$-$C_6$)alkylamino, ($C_2$-$C_6$)dialkylamino, ($C_2$-$C_6$)alkylaminoalkyl, ($C_2$-$C_6$)alkylcarbonyl, ($C_2$-$C_6$)alkoxycarbonyl, ($C_2$-$C_6$)aminocarbonyl, ($C_2$-$C_6$)alkylaminocarbonyl, ($C_3$-$C_8$)dialkylaminocarbonyl, or two adjacent $R^1$ radicals together form an —$OCH_2O$—, —$CH_2CH_2O$—, —$OCH_2CH_2O$—, —OCH($CH_3$)O—, —$OC(CH_3)_2O$—, —$OCF_2O$—, —$CF_2CF_2O$—, —$OCF_2CF_2O$— or —CH=CH—CH=CH— group;

$R^2$ is hydrogen, halogen, cyano;

$R^3$ is hydrogen, ($C_1$-$C_4$)alkyl, ($C_2$-$C_4$)alkenyl, ($C_2$-$C_4$)alkynyl or C(=O)$R^9$, $OR^{10}$, $S(O)_2R^{11}$, $N(R^{12})R^{13}$ or N=C($R^{14}$)$R^{15}$;

$R^4$ is hydrogen, ($C_1$-$C_4$)alkyl optionally substituted by one or two $R^6$ radicals, or C(=O)$R^9$; or $R^3$ and $R^4$ together form a —$(CH_2)_4$—, —$(CH_2)_5$—, —$(CH_2)_2O(CH_2)$— or =C($R^{17}$)N($R^{18}$)$R^{19}$ group;

each $R^6$ radical is independently halogen, ($C_1$-$C_3$)alkoxy, ($C_1$-$C_3$)haloalkoxy, ($C_1$-$C_3$)alkylthio, ($C_1$-$C_3$)haloalkylthio, amino, ($C_1$-$C_3$)alkylamino, ($C_2$-$C_4$)dialkylamino or ($C_2$-$C_4$)alkoxycarbonyl;

$R^5$ is hydrogen, halogen, cyano;

$R^9$ is independently hydrogen, ($C_1$-$C_4$)alkyl, ($C_1$-$C_4$)haloalkyl, ($C_1$-$C_4$)alkoxy, phenyl, phenoxy, benzyl or benzyloxy;

$R^{10}$ is hydrogen, ($C_1$-$C_4$)alkyl or ($C_1$-$C_3$)haloalkyl;

$R^{11}$ is ($C_1$-$C_4$)alkyl or phenyl optionally substituted by one, two or three radicals selected independently from $CH_3$, Cl or $OCH_3$;

$R^{12}$ is hydrogen, ($C_1$-$C_4$)alkyl or C(=O)$R^{24}$;

$R^{13}$ is hydrogen or ($C_1$-$C_4$)alkyl;

$R^{14}$ is hydrogen or ($C_1$-$C_4$)alkyl;

$R^{15}$ is hydrogen or ($C_1$-$C_4$)alkyl;

or $R^{14}$ and $R^{15}$ together form a —$(CH_2)_4$— or —$(CH_2)_5$— group;

$R^{17}$ is hydrogen or ($C_1$-$C_4$)alkyl;

$R^{18}$ and $R^{19}$ are each independently hydrogen or ($C_1$-$C_4$)alkyl;

or $R^{18}$ and $R^{19}$ together form a —$(CH_2)_4$—, —$(CH_2)_5$—, —$CH_2CH=CHCH_2$— or —$(CH_2)_2O(CH_2)_2$— group;

$R^{24}$ is hydrogen, $C_1$-$C_4$ alkyl or benzyl.

Particular preference is given to compounds of the formula (I) or to the N-oxides, salts and agrochemically suitable derivatives of the formulae (1-a), (1-b) and (1-c) thereof, in which the radicals are each defined as follows:

n is an integer selected from 0, 1, 2, 3, 4;

$R^1$ is independently selected from hydrogen, fluorine, chlorine, bromine, iodine, methyl, cyclopropyl, trifluoromethyl, methoxymethyl, methoxy, methylthio, methoxycarbonyl, dimethylamino;

$R^2$ is hydrogen, fluorine or chlorine;
$R^3$ is hydrogen, methyl, ethyl or C(=O)CH$_3$ (acetyl);
$R^4$ is hydrogen, methyl, ethyl or C(=O)CH$_3$ (acetyl);
$R^5$ is hydrogen, fluorine or chlorine.

If the compounds can form, through a hydrogen shift, tautomers whose structure is not formally covered by the formula (I), these tautomers are nevertheless covered by the definition of the inventive compounds of the formula (I), unless a particular tautomer is under consideration.

For example, many carbonyl compounds may be present both in the keto form and in the enol form, both forms being encompassed by the definition of the compound of the formula (I).

According to the nature and the bonding of the substituents, the compounds of the formula (I) may be present as stereoisomers. The possible stereoisomers defined by the specific three-dimensional form thereof, such as enantiomers, diastereomers, Z and E isomers, geometric isomers and atropisomers and mixtures thereof, are all embraced by the formula (I).

When, for example, one or more alkenyl groups are present, diastereomers (Z and E isomers) may occur. When, for example, one or more asymmetric carbon atoms (=asymmetrically substituted carbon atoms) are present, and/or asymmetric sulfur atoms in the form of sulfoxides, which may exist in two enantiomeric forms, enantiomers and diastereomers may occur. Stereoisomers can be obtained from the mixtures obtained in the preparation by customary separation methods, for example by chromatographic separation processes. It is equally possible to selectively prepare stereoisomers by using stereoselective reactions using optically active starting materials and/or auxiliaries. The invention thus also relates to all stereoisomers which are embraced by the formula (I) but are not shown in their specific stereomeric form, and to mixtures thereof.

If one enantiomer is present in excess in a mixture of enantiomers, this excess is referred to as enantiomeric excess, abbreviated to "ee", which is defined as follows:

$$ee=(2X-1)\times 100\%$$

X is the mole fraction (=molar parts) of the enantiomer present in excess in the mixture. For example, 40% ee means an enantiomeric ratio of 70:30.

The "ee" can be determined by various physical methods, for example by chromatography on chiral sorbents in the liquid phase or else in the gas phase, NMR measurements with chiral derivatives, or by determining the specific rotation, but this requires that the specific rotation of the pure enantiomer is known. The optical purity p determinable in this way $$p=[\alpha]/[\alpha]_{max}$$

is often used in practice for characterization of enantiomer mixtures, where [α] is the measured specific rotation of polarized light of a particular frequency and $[\alpha]_{max}$ is the specific rotation of the pure enantiomer.

The optical purity multiplied by 100 is referred to as the optical yield P and is equivalent to the enantiomeric excess, "ee" for short:

$$P=p\times 100\%$$

The same applies to the characterization of diastereomer mixtures, with the difference that the measurement of the specific rotation is insufficient to characterize the diastereomer mixture. In this case, physical methods, for example chromatography on chiral sorbents in the liquid phase or else in the gas phase, can be employed.

The compounds of the formula (I) may form salts. Salts can be formed by the action of a base on those compounds of the formula (I) which bear an acidic hydrogen atom, for example in the case that a COOH group or a sulfonamide group —NHSO$_2$— is present. Suitable bases are, for example, organic amines such as trialkylamines, morpholine, piperidine or pyridine, and also ammonium, alkali metal or alkaline earth metal hydroxides, carbonates and hydrogencarbonates, especially sodium and potassium hydroxide, sodium and potassium carbonate and sodium and potassium hydrogencarbonate. These salts are compounds in which the acidic hydrogen is replaced by an agriculturally suitable cation, for example metal salts, especially alkali metal salts or alkaline earth metal salts, especially sodium and potassium salts, or else ammonium salts, salts with organic amines or quaternary ammonium salts, for example with cations of the formula [NRR'R"R'"]$^+$ in which R to R'" are each independently an organic radical, especially alkyl, aryl, aralkyl or alkylaryl. Also possible are alkylsulfonium and alkylsulfoxonium salts, such as (C$_1$-C$_4$)trialkylsulfonium and (C$_1$-C$_4$)trialkylsulfoxonium salts.

The compounds of the formula (I) can form salts by addition of a suitable inorganic or organic acid, for example mineral acids, for example HCl, HBr, H$_2$SO$_4$, H$_3$PO$_4$ or HNO$_3$, or organic acids, for example carboxylic acids such as formic acid, acetic acid, propionic acid, oxalic acid, lactic acid or salicylic acid, or sulfonic acids, for example p-toluenesulfonic acid, onto a basic group, for example amino, alkylamino, dialkylamino, piperidino, morpholino or pyridino. These salts then contain the conjugate base of the acid as the anion.

Suitable substituents present in deprotonated form, for example sulfonic acids or carboxylic acids, can form internal salts with groups which are themselves protonatable, such as amino groups.

The compounds of the formula (I) and the salts, N-oxides and agrochemically suitable derivatives thereof are also referred to hereinafter as "compounds (I)" according to the invention or used in accordance with the invention.

The names used above and below are familiar to the person skilled in the art and have, more particularly, the meanings elucidated hereinafter:

An inorganic radical is a radical without carbon atoms, preferably halogen, OH and the inorganic salts thereof, in which the H is replaced by a cation, for example alkali metal and alkaline earth metal salts, —NH$_2$ and the ammonium salts thereof with (inorganic) acids, for example mineral acids, —N$_3$ (azide), —N$_2$+A$^-$ (diazonium group, where A$^-$ is an anion), —NO, —NHOH, —NHNH$_2$, —NO$_2$, —ONO, —ONO$_2$, —SH, SOH (sulfenic acid group), S(O)OH (sulfinic acid group), S(O)$_2$OH (or else SO$_3$H for short, sulfonic acid group), —O—SO$_2$H (sulfite group), —O—SO$_3$H (sulfate group), —SO$_2$NH$_2$ (sulfamoyl group), —SO$_2$NHOH (hydroxysulfamoyl group), —NHS(O)OH (sulfinoamino group), —NHS(O)$_2$OH (sulfoamino group), —P(O)(OH)$_2$ (phosphonic acid group), —O—P(OH)$_3$, (phosphate group), —P(O)(NH$_2$)$_2$, —PO(OH)(NH$_2$), —PS(OH)$_2$, —PS(NH$_2$)$_2$ or —PS(OH)(NH$_2$), —B(OH)$_2$ (boronic acid group) and the hydrated or dehydrated forms of the acid groups and the (inorganic) salts thereof;

the expression "inorganic radical" also includes the hydrogen radical (the hydrogen atom), the latter in the definitions often already being part of the unsubstituted base structure of an organic radical (example: "unsubstituted phenyl");

the expression "inorganic radical" here preferably does not include pseudohalogen groups such as CN, SCN, organic metal complexes, carbonate or COOH, which are better assigned to the organic radicals due to the content of carbon atoms.

The term "halogen" means, for example, fluorine, chlorine, bromine or iodine.

When the term is used for a radical, "halogen" means, for example, a fluorine, chlorine, bromine or iodine atom.

Alkyl means a straight-chain, branched or cyclic hydrocarbyl radical. The expression "$(C_1$-$C_4)$-alkyl", for example, is a brief notation for alkyl having one to 4 carbon atoms according to the range stated for carbon atoms and encompasses, for example, the methyl, ethyl, 1-propyl, 2-propyl, 1-butyl, 2-butyl, 2-methylpropyl, tert-butyl, cyclopropyl and cyclobutyl radicals. General alkyl radicals with a larger specified range of carbon atoms, e.g. "$(C_1$-$C_6)$-alkyl", correspondingly also encompass straight-chain, branched or cyclic alkyl radicals with a greater number of carbon atoms, i.e. according to the example also the alkyl radicals having 5 and 6 carbon atoms.

Unless stated specifically, for the hydrocarbyl radicals such as alkyl, alkenyl and alkynyl radicals, including in composite radicals, preference is given to the lower carbon skeletons, for example having 1 to 6 carbon atoms, or having 2 to 6 carbon atoms in the case of unsaturated groups. Alkyl radicals, including in the composite radicals such as alkoxy, haloalkyl etc., mean, for example, methyl, ethyl, cyclo-, n- or i-propyl, cyclo-, n-, i-, t- or 2-butyl, pentyls such as cyclopentyl, n-pentyl, i-pentyl and 1-methylbutyl, hexyls such as cyclohexyl, n-hexyl, i-hexyl and 1,3-dimethylbutyl, heptyls such as cycloheptyl, n-heptyl, 1-methylhexyl and 1,4-dimethylpentyl.

Preferred cyclic alkyl radicals preferably have 3-8 ring carbon atoms, for example cyclopropyl, cyclobutyl, cyclopentyl or cyclohexyl. In the case of optionally substituted cyclic alkyl radicals, cyclic systems with substituents are included, also including substituents with a double bond on the cyclic alkyl radical, for example an alkylidene group such as methylidene.

In the case of optionally substituted cyclic alkyl radicals, polycyclic aliphatic systems are also included, such as bicyclo[1.1.0]butan-1-yl, bicyclo[1.1.0]butan-2-yl, bicyclo[2.1.0]pentan-1-yl, bicyclo[2.1.0]pentan-2-yl, bicyclo[2.1.0]pentan-5-yl, bicyclo[2.2.1]hept-2-yl (norbornyl), adamantan-1-yl and adamantan-2-yl.

In the case of optionally substituted cyclic alkyl radicals, spirocyclic aliphatic systems are also included, for example spiro[2.2]pent-1-yl, spiro[2.3]hex-1-yl, spiro[2.3]hex-4-yl, 3-spiro[2.3]hex-5-yl.

Alkenyl and alkynyl radicals are defined as the possible straight-chain, branched or cyclic unsaturated radicals corresponding to the alkyl radicals, containing at least one double bond and triple bond respectively. Preference is given to radicals having one double bond or having one triple bond.

Alkenyl also includes straight-chain, branched or cyclic hydrocarbyl radicals having more than one double bond, such as 1,3-butadienyl, 1,4-pentadienyl or cyclohexadienyl, but also allenyl or cumulenyl radicals having one or more cumulated double bonds, for example allenyl (1,2-propadienyl), 1,2-butadienyl and 1,2,3-pentatrienyl.

Alkynyl also includes straight-chain, branched or cyclic hydrocarbyl radicals having more than one triple bond, or else having one or more triple bonds and one or more double bonds, for example 1,3-butatrienyl or 3-penten-1-yn-1-yl.

Alkenyl is, for example, vinyl which may optionally be substituted by further alkyl radicals, for example prop-1-en-1-yl, but-1-en-1-yl, allyl, 1-methylprop-2-en-1-yl, 2-methylprop-2-en-1-yl, but-2-en-1-yl, 1-methylbut-3-en-1-yl and 1-methylbut-2-en-1-yl, 2-methylprop-1-en-1-yl, 1-methylprop-1-en-1-yl, 1-methylprop-2-en-1-yl, 2-methylprop-2-en-1-yl, but-2-en-1-yl, but-3-en-1-yl, 1-methylbut-3-en-1-yl or 1-methylbut-2-en-1-yl, pentenyl, 2-methylpentenyl or hexenyl.

$(C_2$-$C_6)$-Alkynyl is, for example, ethynyl, propargyl, 1-methylprop-2-yn-1-yl, 2-butynyl, 2-pentynyl or 2-hexynyl, preferably propargyl, but-2-yn-1-yl, but-3-yn-1-yl or 1-methylbut-3-yn-1-yl.

Cyclic alkenyl radicals are a carbocyclic, nonaromatic, partly unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cyclic alkyl radicals apply correspondingly.

Alkylidene, for example including in the form of $(C_1$-$C_{10})$ alkylidene, is the radical of a straight-chain, branched or cyclic hydrocarbyl radical bonded via a double bond. Possible bonding sites for alkylidene are naturally only positions on the base structure where two hydrogen atoms can be replaced by the double bond; radicals are, for example, $=CH_2$, $=CH-CH_3$, $=C(CH_3)-CH_3$, $=C(CH_3)-C_2H_5$ or $=C(C_2H_5)-C_2H_5$.

Aryl is a mono-, bi- or polycyclic aromatic system having preferably 6 to 14, especially 6 to 10, ring carbon atoms, for example phenyl, naphthyl, anthryl, phenanthrenyl and the like, preferably phenyl.

In the case of optionally substituted aryl, polycyclic systems, such as tetrahydronaphthyl, indenyl, indanyl, fluorenyl, biphenylyl are also included, where the point of attachment is on the aromatic system. In systematic terms, "aryl" is generally also encompassed by the term "optionally substituted phenyl".

The definition "substituted by one or more radicals", unless defined differently, independently means one or more identical or different radicals, where two or more radicals on one cycle as a base structure may form one or more rings.

Substituted radicals such as a substituted alkyl, alkenyl, alkynyl, aryl, phenyl, benzyl, heterocyclyl and heteroaryl radicals are, for example, a substituted radical derived from the unsubstituted base structure, where the substituents are, for example, one or more, preferably 1, 2 or 3, radicals from the group of halogen, alkoxy, alkylthio, hydroxyl, amino, nitro, carboxyl or a group equivalent to the carboxyl group, cyano, isocyano, azido, alkoxycarbonyl, alkylcarbonyl, formyl, carbamoyl, mono- and dialkylaminocarbonyl, substituted amino such as acylamino, mono- and dialkylamino, trialkylsilyl and optionally substituted cyclic alkyl, optionally substituted aryl, optionally substituted heterocyclyl, where each of the latter cyclic groups may also be bonded via heteroatoms or divalent functional groups as in the alkyl radicals mentioned, and alkylsulfinyl, including both enantiomers of the alkylsulfonyl group, alkylsulfonyl, alkylphosphinyl, alkylphosphonyl and, in the case of cyclic radicals (="cyclic base structure"), also alkyl, haloalkyl, alkylthioalkyl, alkoxyalkyl, optionally substituted mono- and dialkylaminoalkyl and hydroxyalkyl; the expression "substituted radicals", such as substituted alkyl (e.g. straight-chain, branched or cyclic alkyl) etc., includes, as substituents, in addition to the saturated hydrocarbonaceous radicals mentioned, corresponding unsaturated aliphatic and aromatic radicals such as optionally substituted alkenyl, alkynyl, alkenyloxy, alkynyloxy, alkenylthio, alkynylthio, alkenyloxycarbonyl, alkynyloxycarbonyl, alkenylcarbonyl, alkynylcarbonyl, mono- and dialkenylaminocarbonyl, mono- and dialkynylaminocarbonyl, mono- and dialkenylamino, mono- and dialkynylamino, trialkenylsilyl, trialkynylsilyl, phenyl, phenoxy etc. In the case of substituted cylic radicals with aliphatic components in the ring, cyclic systems with those substituents bonded to the ring by a double bond are also included, for example substituted by an alkylidene group such as methylidene or ethylidene, or an oxo group, imino group or substituted imino group.

When two or more radicals form one or more rings, these may be carbocyclic, heterocyclic, saturated, partly saturated, unsaturated, for example also aromatic and optionally further substituted. The fused rings are preferably 5- or 6-membered rings, particular preference being given to benzofused cycles.

The substituents mentioned by way of example ("first substituent level") may, if they contain hydrocarbonaceous moieties, optionally be further substituted therein ("second substituent level"), for example by one of the substituents as defined for the first substituent level. Corresponding further substituent levels are possible. The term "substituted radical" preferably embraces just one or two substituent levels.

Preferred substituents for the substituent levels are, for example, amino, hydroxyl, halogen, nitro, cyano, isocyano, mercapto, isothiocyanato, carboxyl, carbonamide, $SF_5$, aminosulfonyl, alkyl, alkenyl, alkynyl, monoalkylamino, dialkylamino, N-alkanoylamino, alkoxy, alkenyloxy, alkynyloxy, alkoxycarbonyl, alkenyloxycarbonyl, alkynyloxycarbonyl, aryloxycarbonyl, alkanoyl, alkenylcarbonyl, alkynylcarbonyl, arylcarbonyl, alkylthio, alkenylthio, alkynylthio, alkylsulfenyl, alkylsulfinyl, including both enantiomers of the alkylsulfinyl group, alkylsulfonyl, monoalkylaminosulfonyl, dialkylaminosulfonyl, alkylphosphinyl, alkylphosphonyl, including both enantiomers for alkylphosphinyl and alkylphosphonyl, N-alkylaminocarbonyl, N,N-dialkylaminocarbonyl, N-alkanoylaminocarbonyl, N-alkanoyl-N-alkylaminocarbonyl, aryl, aryloxy, benzyl, benzyloxy, benzylthio, arylthio, arylamino, benzylamino, heterocyclyl and trialkylsilyl.

Substituents composed of more than one substituent level are preferably, for example, alkoxyalkyl such as monoalkoxyalkyl or dialkoxyalkyl, alkylthioalkyl, alkylthioalkoxy, alkoxyalkoxy such as monoalkoxyalkoxy or dialkoxyalkoxy, benzyl, phenethyl, benzyloxy, haloalkyl, haloalkoxy, haloalkylthio, haloalkanoyl, haloalkylcarbonyl, haloalkoxycarbonyl, haloalkoxyalkoxy, haloalkoxyalkylthio, haloalkoxyalkanoyl, haloalkoxyalkyl, alkanoylalkyl, haloalkanoylalkyl, alkanoyloxyalkyl.

In the case of radicals with carbon atoms, preference is given to those having 1 to 6 carbon atoms, preferably 1 to 4 carbon atoms, especially 1 or 2 carbon atoms. Preference is generally given to substituents from the group of halogen, e.g. fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Particular preference is given here to the substituents methyl, methoxy, fluorine and chlorine.

Substituted amino such as mono- or disubstituted amino is a radical from the group of the substituted amino radicals which are N-substituted, for example, by one or two identical or different radicals from the group of alkyl, hydroxyl, amino, alkoxy, acyl and aryl; preferably mono- and dialkylamino, mono- and diarylamino, such as optionally substituted anilines, acylamino, N,N-diacylamino, N-alkyl-N-arylamino, N-alkyl-N-acylamino and saturated N-heterocycles; preference is given to alkyl radicals having 1 to 4 carbon atoms; aryl is preferably phenyl or substituted phenyl; the definition given below applies to acyl, preferably $(C_1-C_4)$alkanoyl. The same applies to substituted hydroxylamino or hydrazino.

Substituted amino also includes quaternary ammonium compounds (salts) with four organic substituents on the nitrogen atom.

A group equivalent to the carboxyl group is, for example, an alkyl ester, aryl ester, O-alkyl thioester, S-alkyl dithioester, S-alkyl thioester, carboximide ester, carboximide thioester; 5,6-dihydro-1,2,4-dioxazin-3-yl; 5,6-dihydro-1,2,4-oxathiazin-3-yl, trialkyl orthoester, dialkoxyalkylamino ester, dialkylaminoalkoxy ester, trialkylamino ester, amidines, dialkoxyketene acetals or dialkyldithioketene acetals.

Optionally substituted phenyl is preferably phenyl which is unsubstituted or mono- or polysubstituted, preferably up to trisubstituted, by identical or different radicals from the group of halogen, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, $(C_1-C_4)$alkylthio, $(C_1-C_4)$haloalkylthio, cyano, isocyano and nitro, for example o-, m- and p-tolyl, dimethylphenyls, 2-, 3- and 4-chlorophenyl, 2-, 3- and 4-fluorophenyl, 2-, 3- and 4-trifluoromethyl- and -trichloromethylphenyl, 2,4-, 3,5-, 2,5- and 2,3-dichlorophenyl, o-, m- and p-methoxyphenyl.

Optionally substituted cycloalkyl is preferably cycloalkyl, which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl and $(C_1-C_4)$haloalkoxy, especially by one or two $(C_1-C_4)$alkyl radicals.

Optionally substituted heterocyclyl is preferably heterocyclyl which is unsubstituted or mono- or polysubstituted, preferably up to trisubstituted, by identical or different radicals from the group of halogen, cyano, $(C_1-C_4)$alkyl, $(C_1-C_4)$alkoxy, $(C_1-C_4)$alkoxy-$(C_1-C_4)$alkoxy, $(C_1-C_4)$alkoxy-$(C_1-C_4)$alkyl, $(C_1-C_4)$haloalkyl, $(C_1-C_4)$haloalkoxy, nitro and oxo, especially mono- or polysubstituted by radicals from the group of halogen, $(C_1-C_4)$alkyl, $(C_1-C_4)$alkoxy, $(C_1-C_4)$haloalkyl and oxo, most preferably substituted by one or two $(C_1-C_4)$alkyl radicals.

Haloalkyl, -alkenyl and -alkynyl are, respectively, alkyl, alkenyl and alkynyl partly or fully substituted by identical or different halogen atoms, for example monohaloalkyl such as $CH_2CH_2Cl$, $CH_2CH_2F$, $CHClCH_3$, $CHFCH_3$, $CH_2Cl$, $CH_2F$; perhaloalkyl such as $CCl_3$ or $CF_3$ or $CF_2CF_3$; polyhaloalkyl such as $CHF_2$, $CH_2F$, $CH_2CHFCl$, $CHCl_2$, $CF_2CF_2H$, $CH_2CF_3$; haloalkoxy is, for example, $OCF_3$, $OCHF_2$, $OCH_2F$, $OCF_2CF_3$, $OCH_2CF_3$ and $OCH_2CH_2Cl$; the same applies to haloalkenyl and other halogen-substituted radicals.

An organic acid radical is a radical of an oxo acid or thio acid of the general formula

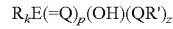

where
R is an organic radical,
E is an atom from the group of C, S, P,
Q is independently an atom or a molecule fragment from the group of O, S, NR' and
R' is independently a hydrogen atom, alkyl, haloalkyl, alkoxyalkyl or in some cases aryl,
k,p are natural numbers, k=1,2; p=0-2;
z is a natural number or zero.

The organic acid radical arises in a formal sense through removal of a hydroxyl group on the acid function, where the organic R radical in the acid may also be bonded to the acid function via one or more heteroatoms:

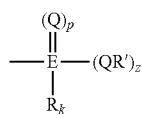

For oxo acids of carbon, this is described in the IUPAC Compendium of Chemical Terminology (1997).

Examples of organic acid radicals derived from the oxo acids or thio acids of sulfur (E=S) are $S(O)OCH_3$, $SO_2OH$, $SO_2OCH_3$ or $SO_2NHR$(N-substituted sulfonamide acids).

In the case that k=1, alkylsulfonyl and alkylsulfinyl radicals, for example $(H_3C)S(O)_2$, $(F_3C)S(O)_2$, p-tolyl$S(O)_2$, $(H_3C)S(O)(NH$-n-$C_4H_9)$, $(C_6H_5)S(S)(O)$ or $(C_6H_5)S(O)$ are also included.

Examples of organic acid radicals derived from the oxo acids or thio acids of phosphorus (E=P) are radicals derived from phosphinic acid and phosphonic acid, where these radicals may be further esterified, for example $—PO(OCH_3)_2$, $(C_2H_5O)P(O)OH$, $(C_2H_{5O})P(O)(SC_6H_5)$, $(H_3CO)P(O)NH(C_6H_5)$ or $—PO(NMe_2)_2$.

In the case that k=1, alkylphosphinyl and alkylphosphonyl radicals are also included, for example $(H_3C)_2$ P(O), $(C_6H_5)_2P(O)$, $(H_3C)(C_6H_5)P(O)$; $(H_3C)P(O)OCH_3$, $(H_5C_2)P(O)(OC_2H_5)$, $(C_6H_5)P(O)(OC_2H_5)$, $(C_2H_5)P(O)(SC_6H_5)$, $(H_3C)P(O)NH(C_6H_5)$, $(H_3C)P(S)(NH$-i-$C_3H_7)$, $(C_6H_5)P(S)(OC_2H_5)$ or $(C_6H_5)P(S)(SC_2H_5)$.

Organic acid radicals derived from the oxo acids of carbon (E=C, Q=O) are also referred to in the narrower sense by the term "acyl".

Examples of acyl are the —CO—R radical of a carboxylic acid HO—CO—R and radicals of acids derived therefrom, or the radical of carbonic monoesters or N-substituted carbamic acids, and carbonates and the esters thereof.

Acyl is, for example, formyl, oxalyl (ester), alkylcarbonyl such as $[(C_1$-$C_4)$alkyl]carbonyl, haloalkylcarbonyl, phenylcarbonyl, alkyloxycarbonyl, especially tert-butyloxycarbonyl, phenyloxycarbonyl, benzyloxycarbonyl, fluorenyloxycarbonyl, N-alkyl-1-iminoalkyl, N-alkyl- and N,N-dialkylcarbamoyl. The radicals may each be substituted further in the alkyl or phenyl moiety, for example in the alkyl moiety by one or more radicals from the group of halogen, cyano, alkoxy, phenyl and phenoxy; examples of substituents in the phenyl moiety are the substituents already mentioned above in general for substituted phenyl.

Acyl is preferably an acyl radical in the narrower sense, i.e. a radical of an organic acid in which the acid group is bonded directly to the carbon atom of an organic radical, for example alkanoyl such as formyl and acetyl, aroyl such as phenylcarbonyl, and other radicals of saturated or unsaturated organic acids.

"Aroyl" is an aryl radical as defined above which is bonded via a carbonyl group, for example the benzoyl group.

When a general radical is defined as "hydrogen", this means a hydrogen atom.

The "yl position" of a radical denotes the bonding site thereof.

The present invention also provides methods for preparing the inventive compounds. The inventive compounds can be prepared by various alternative processes.

In some of the processes which follow, solvents are used. In this context, "inert solvents" refers in each case to solvents which are inert under the particular reaction conditions, but need not be inert under all reaction conditions.

Picolinic acids of the formula (I) can be prepared, for example, by hydrolyzing the corresponding carboxylic esters of the formula (I) in which, for example, R'=methyl, ethyl, isopropyl, using LiOH, NaOH, KOH or other suitable bases. The reaction can be performed, for example, in various solvents such as water, methanol, ethanol, tetrahydrofuran, dioxane, diethyl ether, dichloromethane, dichloroethane, acetonitrile, toluene or other suitable solvents, or corresponding mixtures. The reaction temperatures are generally between 0° C. and 100° C.

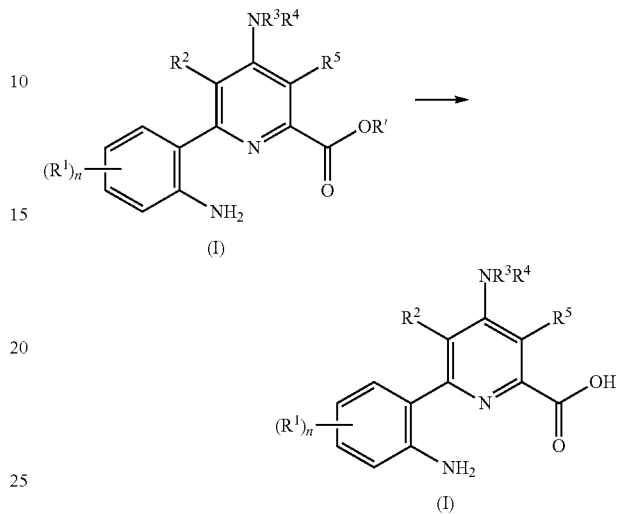

Alternatively, compounds of the formula (I) can also be converted by reaction of halogen compounds of the formula (II) with boronic acids ($R^X$ and $R^Y$=H) or boronic esters ($R^X$ and $R^Y$=alkyl, aryl; where both radicals together also include cyclic structures, for example pinacol or catechol esters) of the formula (III). It is also possible to use the corresponding trifluoroborate salts for this reaction.

In the reaction generally known as the Suzuki coupling, compounds of the formula (II) react with the compounds of the formula (III) with use of a suitable base, for example triethylamine, potassium tert-butoxide, potassium carbonate, potassium acetate, potassium phosphate, sodium hydrogencarbonate, sodium carbonate, barium hydroxide, sodium hydroxide, cesium carbonate or cesium fluoride, and a suitable palladium catalyst, for example $Pd(PPh_3)_4$, $Pd(OAc)_2$, $Pd(dppf)_2Cl_2$ or $Pd_2(dba)_3$. The addition of further ligands, for example, X-Phos, S-Phos, Ru-Phos, $P(tBu)_3$, $P(Cy)_3$, P(o-Tol)$_3$ leads in some cases to improved yields, or actually enables any reaction at all. Suitable solvents for this reaction are, for example, methanol, ethanol, toluene, dimethylformamide, dimethyl sulfoxide, dioxane, tetrahydrofuran, dimethoxyethane, ethylene glycol and water; it is also possible to use various solvent mixtures. The reactions proceed generally at a temperature between 20° C. and 200° C. Particularly at relatively high temperatures, the use of microwave technology is suitable (see, for example: "Microwaves in Organic and Medicinal Chemistry", C. O. Kappe and A. Stadler, Verlag Wiley, 2005).

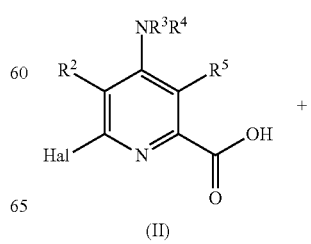

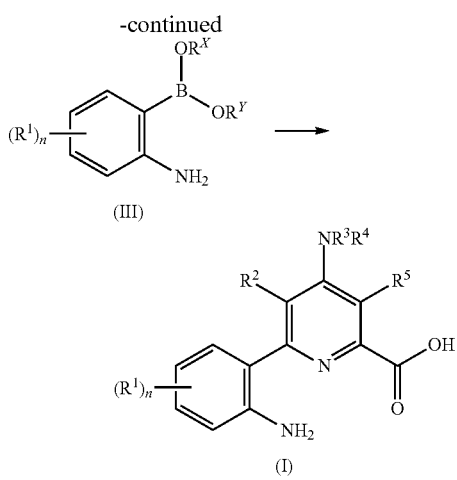

When esters of the formula (IV) in which, for example, R'=methyl, ethyl or isopropyl are used analogously to the above-described conversion (Suzuki coupling), the corresponding carboxylic esters of the formula (I) are obtained with use of suitable solvents, bases, catalysts and reaction conditions.

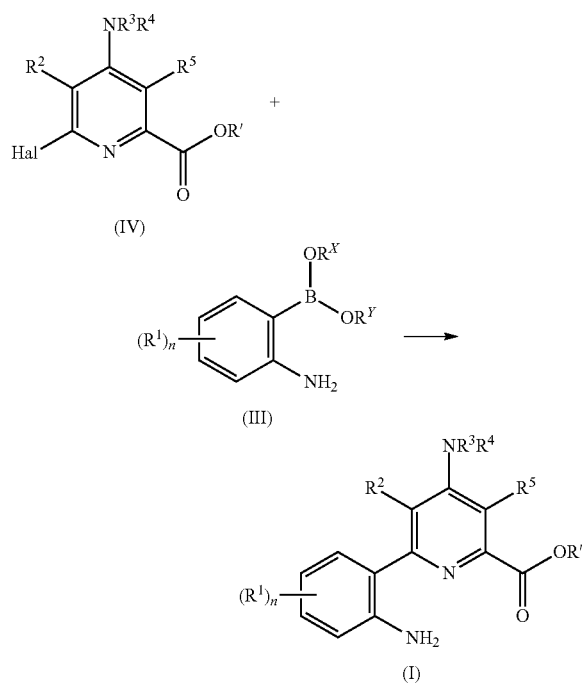

The preparation of compounds of the formulae (II) and (IV) has already been described in various literature references and patent specifications: W. K. Brewster et al., Tetrahedron Lett. 2010, 51, 79-81; G. Liu et al., Bioorg. Med. Chem. Lett. 2006, 16, 5723-5730; WO 2001/51468; WO 2005142524; WO 2006/62979; WO 2009/89263; U.S. Pat. Nos. 4,336,384; 6,297,197; US 2003/114311; US 2004/198608; US 2006/173050; US 2007/179060.

Some compounds of the formula (I) where, for example, $R^5$=alkyl, alkenyl or alkynyl, and, for example, R'=methyl, ethyl or isopropyl, can be prepared by means of the reaction commonly known as Stille coupling from tin compounds of the formula (V) and the appropriately halogenated compounds of the formula (I-1) wherein, preferably, Hal=chlorine, bromine or iodine. Reactions of this kind are known from the literature (see, for example, "Organic Reactions, Vol. 50", V. Farina et al., Verlag John Wiley & Sons Inc., 1997) and have already been described with similar compounds in WO 2009/046090:

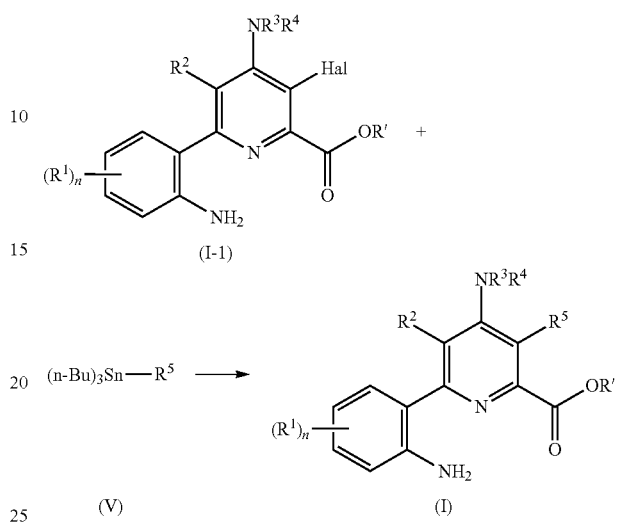

The preparation of the boronic acid derivatives of the formula (III) mentioned is described in detail in the literature (see, for example: "Boronic Acids", Dennis G. Hall, Wiley-VCH Verlag, Weinheim 2005).

One means of preparing compounds of the formula (III) is the reaction of ortho-halogenated anilines of the formula (V) with boronates of the formula (VI) or diboranes of the formula (VII). Using a suitable base, for example triethylamine, potassium tert-butoxide, potassium acetate, potassium phosphate, sodium carbonate or cesium fluoride, and a suitable palladium catalyst, for example $Pd(PPh_3)_4$, $Pd(OAc)_2$, $Pd(dppf)_2Cl_2$ or $Pd_2(dba)_3$, it is possible to generate the boronic esters of the formula (III). Suitable solvents for this reaction are, for example, toluene, dimethylformamide, dimethyl sulfoxide, dioxane, tetrahydrofuran, dimethoxyethane or ethylene glycol. The reactions generally proceed at a temperature between 20° C. and 200° C.

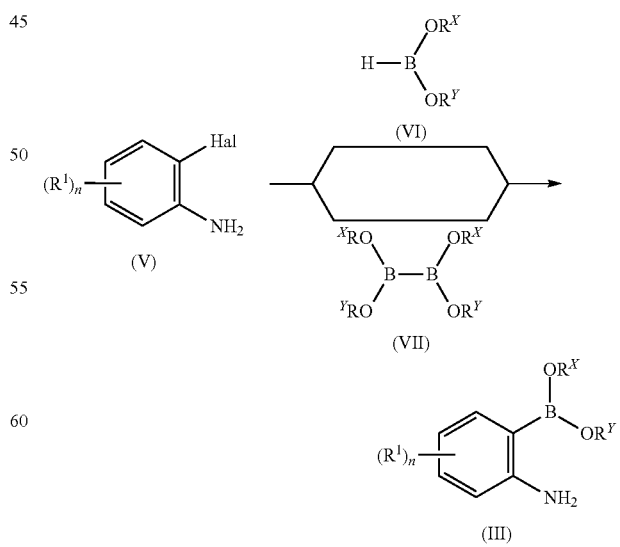

The trifluoroborate salts already mentioned above are obtained by reacting the corresponding boronic acids or boronic esters of the formula (III) with KHF$_2$ (in this regard, see: G. Molander, *Acc. Chem. Res.* 2007, 40, 275-286).

Libraries of inventive compounds which can be synthesized by the above-mentioned reactions can also be prepared in a parallelized manner.

In addition to the methods described here, inventive compounds can be prepared completely or partially by solid phase-supported methods. Either on a solid phase or in the liquid phase, the performance of single or multiple synthesis steps can be supported by the use of microwave technology. The specialist literature describes a series of experimental protocols, for example Microwaves in Organic and Medicinal Chemistry (editors C. O. Kappe and A. Stadler), Verlag Wiley, 2005.

The inventive compounds of the formula (I) (and/or the salts, esters or agrochemically suitable derivatives thereof), referred to collectively hereinafter as "inventive compounds", have excellent herbicidal efficacy against a broad spectrum of economically important monocotyledonous and dicotyledonous annual weed plants. The active ingredients also have good control over perennial weed plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example weed plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be applied, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though there is no intention to restrict the enumeration to particular species:

monocotyledonous weed plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.* dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the inventive compounds are applied to the soil surface before germination, either the weed seedlings are prevented completely from emerging or the weeds grow until they have reached the cotyledon stage, but then stop growing and, eventually, after three to four weeks have passed, die completely.

When the active ingredients are applied post-emergence to the green parts of the plants, growth stops after the treatment, and the weed plants remain at the growth stage at the time of application, or they die completely after a certain time, such that competition by the weeds, which is harmful to the crop plants, is thus eliminated very early and in a sustained manner.

Even though the inventive compounds display excellent herbicidal activity against monocotyledonous and dicotyledonous weeds, damage to crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia,* or monocotyledonous crops of the genera *Allium, Ananas, Asparagus, Avena, Hordeum, Oryza, Panicum, Saccharum, Secale, Sorghum, Triticale, Triticum, Zea,* especially *Zea* and *Triticum,* depending on the structure of the particular inventive compound and its application rate, is only insignificant or entirely absent. For these reasons, the present compounds are very suitable for selective control of unwanted plant growth in plant crops such as agriculturally useful plants or ornamentals.

Furthermore, the inventive compounds (depending on their particular structure and the application rate applied) have outstanding growth-regulating properties in crop plants. They intervene in the plant's own metabolism with a regulatory effect, and can thus be used to control plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, this can reduce or completely prevent lodging.

Owing to their herbicidal and plant growth-regulating properties, the active ingredients can also be used to control weed plants in crops of known genetically modified plants or of those yet to be developed. In general, the transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other special properties relate, for example, to the harvested material with regard to quantity, quality, storability, composition and specific constituents. For instance, there are known transgenic plants with an elevated starch content or altered starch quality, or with a different fatty acid composition in the harvested material. Further special properties may be tolerance or resistance to abiotic stress factors, for example heat, cold, drought, salinity and ultraviolet radication.

Preference is given to the use of the inventive compounds of the formula (I) and/or salts thereof in economically important transgenic crops of useful plants and ornamental plants, for example of cereals such as wheat, barley, rye, oats, sorghum and millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been many descriptions of:

- genetic modifications of crop plants for the purpose of modifying the starch synthesized in the plants (for example WO 92/011376 A, WO 92/014827 A, WO 91/019806 A),
- transgenic crop plants which are resistant to certain herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (Glyphosate ALS Tolerant),
- transgenic crop plants, for example cotton, which is capable of producing *Bacillus thuringiensis* toxins (Bt toxins), which make the plants resistant to certain pests (EP 0142924 A, EP 0193259 A),
- transgenic crop plants having a modified fatty acid composition (WO 91/013972 A),
- genetically modified crop plants with novel constituents or secondary metabolites, for example novel phytoalexins, which bring about an increased disease resistance (EP 0309862 A, EP 0464461 A),
- genetically modified plants with reduced photorespiration which feature higher yields and higher stress tolerance (EP 0305398 A),
- transgenic crop plants which produce pharmaceutically or diagnostically important proteins ("molecular pharming"),
- transgenic crop plants which are notable for higher yields or better quality,
- transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.) Gene Transfer to Plants, Springer Lab Manual (1995), Springer Verlag Berlin, Heidelberg, or Christou, "Trends in Plant Science" 1 (1996) 423-431.

For such recombinant manipulations, nucleic acid molecules which allow mutagenesis or a sequence change by recombination of DNA sequences can be introduced into plasmids. With the aid of standard methods, it possible, for example, to undertake base exchanges, remove parts of sequences or add natural or synthetic sequences. For the joining of the DNA fragments to one another, adaptors or linkers can be attached to the fragments; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone", VCH Weinheim 2nd edition 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product.

For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give complete plants. In principle, the transgenic plants may be plants of any desired plant species, i.e. both monocotyledonous and dicotyledonous plants.

Thus, it is possible to obtain transgenic plants whose properties are altered by overexpression, suppression or inhibition of homologous (=natural) genes or gene sequences, or expression of heterologous (=foreign) genes or gene sequences. The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The inventive compounds can be used with particular preference in transgenic crop plants which are resistant to a combination of glyphosates and glufosinates, glyphosates and sulfonylureas or imidazolinones. The inventive compounds can be used with very particular preference in transgenic crop plants, for example corn or soybeans with the trade name or the designation Optimum™ GAT™ (Glyphosate ALS Tolerant).

On employment of the inventive active ingredients in transgenic crops, not only do the effects toward weed plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds of the formula (I) as herbicides for control of weed plants in transgenic crop plants.

The inventive compounds can be used in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Examples of possible formulations include: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes.

These individual formulation types are known in principle and are described, for example, in: Winnacker-Küchler, "Chemische Technologie" [Chemical Technology], volume 7, C. Hanser Verlag Munich, 4th ed. 1986; Wade van Valkenburg, "Pesticide Formulations", Marcel Dekker, N.Y., 1973; K. Martens, "Spray Drying" Handbook, 3rd ed. 1979, G. Goodwin Ltd. London.

The necessary formulation assistants, such as inert materials, surfactants, solvents and further additives are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry"; 2nd ed., J. Wiley & Sons, N.Y.; C. Marsden, "Solvents Guide"; 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesell., Stuttgart 1976; Winnacker-1-Küchler, "Chemische Technologie", volume 7, C. Hanser Verlag Munich, 4th ed. 1986.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tankmix.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate. To produce the wettable powders, the herbicidally active ingredients are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers).

The emulsifiers used may be, for example: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or granulated inert material. Suitable active ingredients can also be granulated in the manner customary for the production of fertilizer granules—if desired as a mixture with fertilizers.

Water-dispersible granules are prepared generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th ed., Blackwell Scientific Publications, Oxford, 1968, pages 101-103.

The agrochemical formulations contain generally 0.1 to 99% by weight, especially 0.1 to 95% by weight, of inventive compounds.

In wettable powders, the active ingredient concentration is, for example, about 10 to 90% by weight; the remainder to 100% by weight consists of the customary formulation constituents. In emulsifiable concentrates, the active ingredient concentration may be about 1 to 90% and preferably 5 to 80% by weight. Dust-type formulations contain 1 to 30% by weight of active ingredient, preferably usually 5 to 20% by weight of active ingredient; sprayable solutions contain about 0.05 to 80% and preferably 2 to 50% by weight of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

The inventive compounds can be combined with further active fungicidal, insecticidal, nematicidal or herbicidal ingredients, or with safeners.

Usable combination partners for the inventive compounds in mixture formulations or in a tankmix are, for example, known active ingredients based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 15th edition, The British Crop Protection Council and the Royal Soc. of Chemistry, 2006 and literature cited therein.

Known herbicides or plant growth regulators which can be combined with the inventive compounds include, for example, the following active ingredients (the compounds are referred to by the common name according to the International Organization for Standardization (ISO) or by the chemical name or by the code number) and always include all use forms, such as salts, acids, esters and isomers such as stereoisomers and optical isomers. By way of example, one and in some cases even several use forms are mentioned: acetochlor, acifluorfen, acifluorfen-sodium, aclonifen, alachlor, allidochlor, alloxydim, alloxydim-sodium, ametryn, amicarbazone, amidochlor, amidosulfuron, aminocyclopyrachlor, aminocyclopyrachlor-potassium, aminocyclopyrachlor-methyl, aminopyralid, amitrole, ammoniumsulfamate, anilofos, asulam, atrazine, azafenidin, azimsulfuron, beflubutamid, benazolin, benazolin-ethyl, benfluralin, benfuresate, bensulfuron, bensulfuron-methyl, bensulide, bentazone, benzobicyclon, benzofenap, bicyclopyrone, bifenox, bilanafos, bilanafos-sodium, bispyribac, bispyribac-sodium, bromacil, bromobutide, bromofenoxim, bromoxynil, bromoxynil-butyrate, -potassium, -heptanoate and -octanoate, busoxinone, butachlor, butafenacil, butamifos, butenachlor, butralin, butroxydim, butylate, cafenstrole, carbetamide, carfentrazone, carfentrazone-ethyl, chloramben, chlorbromuron, chlorfenac, chlorfenac-sodium, chlorfenprop, chlorflurenol, chlorflurenol-methyl, chloridazon, chlorimuron, chlorimuron-ethyl, chlorophthalim, chlorotoluron, chlorthaldimethyl, chlorsulfuron, cinidon, cinidon-ethyl, cinmethylin, cinosulfuron, clethodim, clodinafop, clodinafop-propargyl, clomazone, clomeprop, clopyralid, cloransulam, cloransulam-methyl, cumyluron, cyanamide, cyanazine, cycloate, cyclosulfamuron, cycloxydim, cyhalofop, cyhalofop-butyl, cyprazine, 2,4-D, 2,4-D-butoyl, -butyl, -dimethylammonium, -diolamine, -ethyl, 2-ethylhexyl, dazomet, -isobutyl, -isooctyl, -isopropylammonium, -potassium, -triisopropanolammonium and -trolamine, 2,4-DB, 2,4-DB-butyl, -dimethylammonium isooctyl, -potassium and -sodium, daimuron (dymron), dalapon, n-decanol, desmedipham, detosyl-pyrazolate (DTP), dicamba, dichlobenil, dichlorprop, dichlorprop-P, diclofop, diclofop-methyl, diclofop-P-methyl, diclosulam, difenzoquat, diflufenican, diflufenzopyr, diflufenzopyr-sodium, dimefuron, dimepiperate, dimethachlor, dimethametryn, dimethenamid, dimethenamid-P, dimetrasulfuron, dinitramine, dinoterb, diphenamid, diquat, diquat-dibromide, dithiopyr, diuron, DNOC, endothal, EPTC, esprocarb, ethalfluralin, ethametsulfuron, ethametsulfuron-methyl, ethiozin, ethofumesate, ethoxyfen, ethoxyfenethyl, ethoxysulfuron, etobenzanid, F-5331, i.e. N-[2-chloro-4-fluoro-5-[4-(3-fluoropropyl)-4,5-dihydro-5-oxo-1H-tetrazol-1-yl]phenyl]ethanesulfonamide, F-7967, i.e. 3-[7-chloro-5-fluoro-2-(trifluoromethyl)-1H-benzimidazol-4-yl]-1-methyl-6-(trifluoromethyl)pyrimidine-2,4(1H,3H)-dione, fenoxaprop, fenoxaprop-P, fenoxaprop-ethyl, fenoxaprop-P-ethyl, fenoxasulfone, fentrazamide, flamprop, flamprop-M-isopropyl, flamprop-M-methyl, flazasulfuron, florasulam, fluazifop, fluazifop-P, fluazifop-butyl, fluazifop-P-butyl, flucarbazone, flucarbazone-sodium, flucetosulfuron, fluchloralin, flufenacet (thiafluamide), flufenpyr, flufenpyr-ethyl, flumetsulam, flumiclorac, flumiclorac-pentyl, flumioxazin, fluometuron, flurenol, flurenol-butyl, -dimethylammonium and -methyl, fluoroglycofen, fluoroglycofen-ethyl, flupropenate, flupyrsulfuron, flupyrsulfuron-methyl-sodium, fluridone, fluorochloridone, fluoroxypyr, fluoroxypyr-meptyl, flurtamone, fluthiacet, fluthiacet-methyl, fluthiamide, fomesafen, fomesafen-sodium, foramsulfuron, fosamine, glufosinate, glufosinate-ammonium, glufosinate-P-sodium, glufosinate-P-ammonium, glufosinate-P-sodium, glyphosate, glyphosate-ammonium, -isopropylammonium, -diammonium, -dimethylammonium, -potassium, -sodium and -trimesium, H-9201, i.e. O-(2,4-dimethyl-6-nitrophenyl)-O-ethyl-isopropyl phosphoramidothioate, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, hexazinone, HW-02, i.e. 1-(dimethoxyphosphoryl)ethyl (2,4-dichlorophenoxy)acetate, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazethapyr, imazethapyr-immonium, imazosulfuron, indanofan, indaziflam, iodosulfuron, iodosulfuron-methyl-sodium, ioxynil, ioxynil-octanoate, -potassium and sodium, ipfencarbazone, isoproturon, isouron, isoxaben, isoxaflutole, karbutilate, KUH-043, i.e. 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, ketospiradox, lactofen, kenacil, kinuron, MCPA, MCPA-butotyl, -dimethylammonium, -2-ethylhexyl, -isopropylammonium, -potassium and -sodium, MCPB, MCPB-methyl, -ethyl and -sodium, mecoprop, mecoprop-sodium, and -butotyl, mecoprop-P, mecoprop-P-butotyl, dimethylammonium, -2-ethylhexyl and -potassium, mefenacet, mefluidide, mesosulfuron, mesosulfuron-methyl, mesotrione, methabenzthiazuron, metam, metamifop, metamitron, metazachlor, metazosulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinat, monolinuron, monosulfuron, monosulfuron-ester, MT-128, i.e. 6-chloro-N-[(2E)-3-chloroprop-2-en-1-yl]-5-methyl-N-phenylpyridazin-3-amine, MT-5950, i.e. N-[3-chloro-4-(1-methylethyl)-phenyl]-2-methylpentanamide, NGGC-011, napropamide, NC-310, i.e. 4-(2,4-dichlorobenzoyl)-1-methyl-5-benzyloxypyrazole, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefon, oxyfluorfen, paraquat, paraquat dichloride, pebulate, pendimethalin, penoxsulam, pentachlorphenol, pentoxazone, pethoxamid, petroleum oils, phenmedipham, picloram, picolinafen, pinoxaden, piperophos, pretilachlor, primisulfuron, primisulfuron-methyl, prodiamine, prifluraline, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quizalofop, quizalofop-ethyl, quizalofop-P, quizalofop-P-ethyl, quizalofop-P-tefuryl, rimsulfuron, saflufenacil, sethoxydim, siduron, simazine, simetryn, sulcotrion, sulfentrazone, sulfometuron, sulfometuron-methyl, sulfosulfuron, SW-065, SYN-523, SYP-249, i.e. 1-ethoxy-3-methyl-1-oxobut-3-en-2-yl 5-[2-chloro-4-(trifluoromethyl)phenoxy]-2-nitrobenzoate, SYP-300, i.e. 1-[7-fluoro-3-oxo-4-(prop-2-yn-1-yl)-3,4-dihydro-2H-1,4-benzoxazin-6-yl]-3-propyl-2-thioxoimidazolidine-4,5-dione, 2,3,6-TBA, TCA (trifluoroacetic acid), TCA-sodium, tebuthiuron, tefuryltrione, tembotrione, tepraloxydim, terbacil, terbucarb, terbumeton, terbuthylazin, terbutryn, thenylchlor, thiazopyr, thiencarbazone, thiencarbazone-methyl, thifensulfuron, thifensulfuron-methyl, thiobencarb, topramezone, tralkoxydim, triafamone, tri-allate, triasulfuron, triaziflam, tribenuron, tribenuron-methyl, triclopyr, trietazine, trifloxysulfuron, trifloxysulfuron-sodium, trifluralin, triflusulfuron, triflusulfuron-methyl, tritosulfuron, urea sulfate, vernolate, ZJ-0862, i.e. 3,4-dichloro-N-{2-[(4,6-dimethoxypyrimidin-2-yl)oxy]benzyl}aniline, and the following compounds:

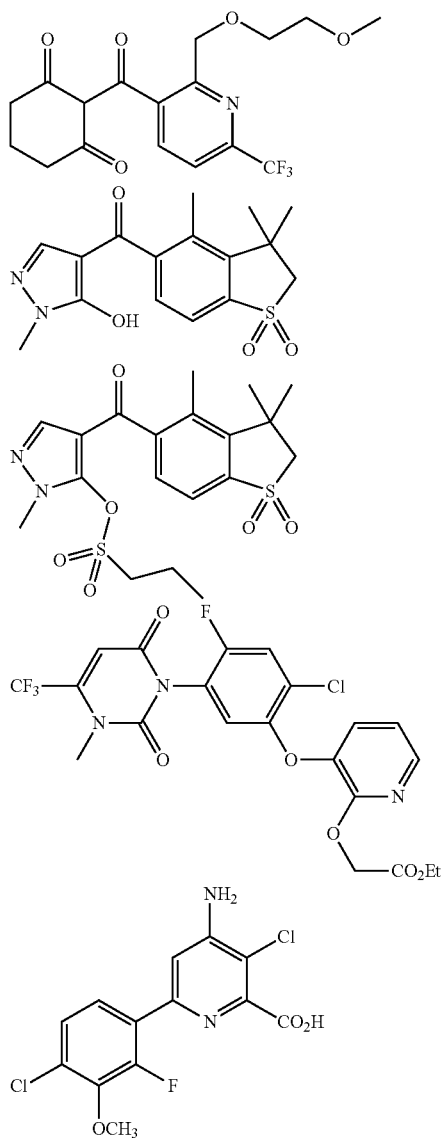

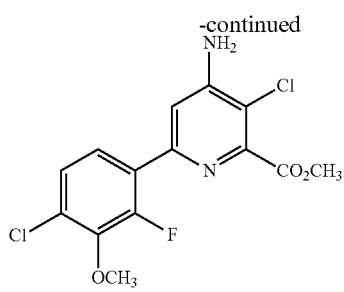

Examples of plant growth regulators as possible mixing partners are:
acibenzolar, acibenzolar-S-methyl, 5-aminolevulinic acid, ancymidol, 6-benzylaminopurine, brassinolide, catechol, chlormequat chloride, cloprop, cyclanilide, 3-(cycloprop-1-enyl)propionic acid, daminozide, dazomet, n-decanol, dikegulac, dikegulac-sodium, endothal, endothal-dipotassium, -disodium, and mono(N,N-dimethylalkylammonium), ethephon, flumetralin, flurenol, flurenol-butyl, flurprimidol, forchlorfenuron, gibberellic acid, inabenfide, indol-3-acetic acid (IAA), 4-indol-3-ylbutyric acid, isoprothiolane, probenazole, jasmonic acid, jasmonic acid methyl ester, maleic hydrazide, mepiquat chloride, 1-methylcyclopropene, 2-(1-naphthyl)acetamide, 1-naphthylacetic acid, 2-naphthyloxyacetic acid, nitrophenolate mixture, 4-oxo-4-[(2-phenylethyl)amino]butyric acid, paclobutrazol, N-phenylphthalamic acid, prohexadione, prohexadione-calcium, prohydrojasmone, salicylic acid, strigolactone, tecnazene, thidiazuron, triacontanol, trinexapac, trinexapac-ethyl, tsitodef, uniconazole, uniconazole-P.

Of particular interest is the selective control of weed plants in crops of useful plants and ornamentals. Even though the inventive compounds already have very good to adequate selectivity in many crops, it is possible in principle for phytotoxicities on the crop plants to occur in some crops, and in particular also in the case of mixtures with other, less selective herbicides. Of particular interest in this regard are combinations which comprise the inventive compounds in combination with safeners, and optionally further pesticides such as herbicides. The safeners, which are used in an antidotically effective content, reduce the phytotoxic side effects of the pesticides used, for example in economically important crops such as cereals (e.g. wheat, barley, rye, corn, rice, millet), sugar beet, sugar cane, oilseed rape, cotton and soybeans, preferably cereals.

The following groups of compounds, for example, are useful as safeners:
S1) compounds from the group of heterocyclic carboxylic acid derivatives:
S1$^a$) compounds of the dichlorophenylpyrazoline-3-carboxylic acid type (S1$^a$), preferably compounds such as 1-(2,4-dichlorophenyl)-5-(ethoxycarbonyl)-5-methyl-2-pyrazoline-3-carboxylic acid, 1-(2,4-dichlorophenyl)-5-(ethoxycarbonyl)-5-methyl-2-pyrazoline-3-carboxylic acid ethyl ester (S1-1) ("mefenpyr-diethyl"), and related compounds, as described in WO-A-91/07874;
S1$^b$) derivatives of dichlorophenylpyrazolecarboxylic acid (S1$^b$), preferably compounds such as 1-(2,4-dichlorophenyl)-5-methylpyrazole-3-carboxylic acid ethyl ester (S1-2), 1-(2,4-dichlorophenyl)-5-isopropylpyrazole-3-carboxylic acid ethyl ester (S1-3), 1-(2,4-dichlorophenyl)-5-(1,1-dimethylethyl)pyrazole-3-carboxylic acid ethyl ester (S1-4) and related compounds, as described in EP-A-333 131 and EP-A-269 806;

S1$^c$) derivatives of 1,5-diphenylpyrazole-3-carboxylic acid (S1$^c$), preferably compounds such as 1-(2,4-dichlorophenyl)-5-phenylpyrazole-3-carboxylic acid ethyl ester (S1-5), 1-(2-chlorophenyl)-5-phenylpyrazole-3-carboxylic acid methyl ester (S1-6) and related compounds, as described, for example, in EP-A-268554;

S1$^d$) compounds of the triazolecarboxylic acid type (S1$^d$), preferably compounds such as fenchlorazol(-ethyl ester), i.e. 1-(2,4-dichlorophenyl)-5-trichloromethyl-(1H)-1,2,4-triazole-3-carboxylic acid ethyl ester (S1-7), and related compounds, as described in EP-A-174 562 and EP-A-346 620;

S1$^e$) compounds of the 5-benzyl- or 5-phenyl-2-isoxazoline-3-carboxylic acid type, or of the 5,5-diphenyl-2-isoxazoline-3-carboxylic acid type (S1$^e$), preferably compounds such as 5-(2,4-dichlorobenzyl)-2-isoxazoline-3-carboxylic acid ethyl ester (S1-8) or 5-phenyl-2-isoxazoline-3-carboxylic acid ethyl ester (S1-9) and related compounds, as described in WO-A-91/08202, or 5,5-diphenyl-2-isoxazolinecarboxylic acid (S1-10) or 5,5-diphenyl-2-isoxazoline-3-carboxylic acid ethyl ester (S1-11) ("isoxadifen-ethyl") or 5,5-diphenyl-2-isoxazoline-3-carboxylic acid n-propyl ester (S1-12) or of the 5-(4-fluorophenyl)-5-phenyl-2-isoxazoline-3-carboxylic acid ethyl ester type (S1-13), as described in patent application WO-A-95/07897.

S2) Compounds from the group of 8-quinolinyloxy derivatives (S2):

S2$^a$) compounds of the 8-quinolinoxyacetic acid type (S2$^a$), preferably (5-chloro-8-quinolinoxy)acetic acid 1-methylhexyl ester ("cloquintocet-mexyl") (S2-1), (5-chloro-8-quinolinoxy)acetic acid 1,3-dimethylbut-1-yl ester (S2-2), (5-chloro-8-quinolinoxy)acetic acid 4-allyloxybutyl ester (S2-3), (5-chloro-8-quinolinoxy)acetic acid 1-allyloxyprop-2-yl ester (S2-4), (5-chloro-8-quinolinoxy)acetic acid ethyl ester (S2-5), (5-chloro-8-quinolinoxy)acetic acid methyl ester (S2-6), (5-chloro-8-quinolinoxy)acetic acid allyl ester (S2-7), (5-chloro-8-quinolinoxy)acetic acid 2-(2-propylideneiminoxy)-1-ethyl ester (S2-8), (5-chloro-8-quinolinoxy)acetic acid 2-oxoprop-1-yl ester (S2-9) and related compounds, as described in EP-A-86 750, EP-A-94 349 and EP-A-191 736 or EP-A-0 492 366, and also (5-chloro-8-quinolinoxy)acetic acid (S2-10) and the hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^b$) compounds of the (5-chloro-8-quinolinoxy)malonic acid type (S2$^b$), preferably compounds such as (5-chloro-8-quinolinoxy)malonic acid diethyl ester, (5-chloro-8-quinolinoxy)malonic acid diallyl ester, (5-chloro-8-quinolinoxy)malonic acid methyl ethyl ester and related compounds, as described in EP-A-0 582 198.

S3) Active ingredients of the dichloroacetamide type (S3), which are frequently used as pre-emergence safeners (soil-active safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N—[(allylaminocarbonyl)methyl]-dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "diclonon" (dicyclonone) or "BAS145138" or "LAB145138" (S3-9) ((RS)-1-dichloroacetyl-3,3,8a-trimethylperhydropyrrolo[1,2-a]pyrimidin-6-one from BASF, "furilazol" or "MON 13900" ((RS)-3-dichloroacetyl-5-(2-furyl)-2,2-dimethyl-oxazolidine) (S3-10), and the (R) isomer thereof (S3-11).

S4) Compounds from the class of acylsulfonamides (S4):

S4$^a$) N-acylsulfonamides of the formula (S4$^a$) and salts thereof, as described in WO-A-97/45016,

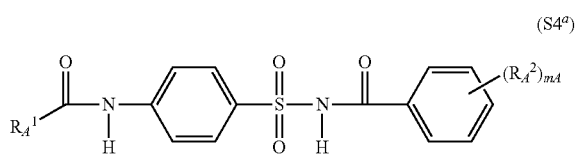

(S4$^a$)

in which $R_A^1$ is $(C_1-C_6)$alkyl, $(C_3-C_6)$cycloalkyl, the 2 latter radicals being substituted by $v_A$ substituents from the group of halogen, $(C_1-C_4)$alkoxy, $(C_1-C_6)$haloalkoxy and $(C_1-C_4)$alkylthio, and, in the case of cyclic radicals, also by $(C_1-C_4)$alkyl and $(C_1-C_4)$haloalkyl;

$R_A^2$ is halogen, $(C_1-C_4)$alkyl, $(C_1-C_4)$alkoxy, $CF_3$;

$m_A$ is 1 or 2;

$V_A$ is 0, 1, 2 or 3;

S4$^b$) compounds of the 4-(benzoylsulfamoyl)benzamide type of the formula (S4$^b$) and salts thereof, as described in WO-A-99/16744,

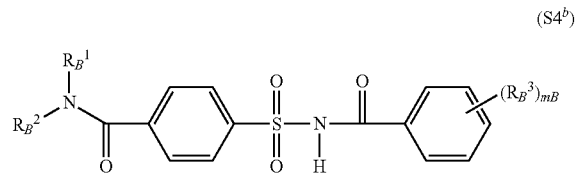

(S4$^b$)

in which $R_B^1$, $R_B^2$ are each independently hydrogen, $(C_1-C_6)$alkyl, $(C_3-C_6)$cycloalkyl, $(C_3-C_6)$alkenyl, $(C_3-C_6)$alkynyl, $R_B^3$ is halogen, $(C_1-C_4)$alkyl, $(C_1-C_4)$haloalkyl or $(C_1-C_4)$alkoxy and $m_B$ is 1 or 2, for example those in which $R_B^1$=cyclopropyl, $R_B^2$=hydrogen and $(R_B^3)$=2-OMe (S4-1, "cyprosulfamide"), $R_B^1$=cyclopropyl, $R_B^2$=hydrogen and $(R_B^3)$=5-Cl-2-OMe (S4-2), $R_B^1$=ethyl, $R_B^2$=hydrogen and $(R_B^3)$=2-OMe (S4-3), $R_B^1$=isopropyl, $R_B^2$=hydrogen and $(R_B^3)$=5-Cl-2-OMe (S4-4) and $R_B^1$=isopropyl, $R_B^2$=hydrogen and $(R_B^3)$=2-OMe (S4-5).

S4$^c$) compounds from the class of benzoylsulfamoylphenylureas of the formula (S4$^c$), as described in EP-A-365484

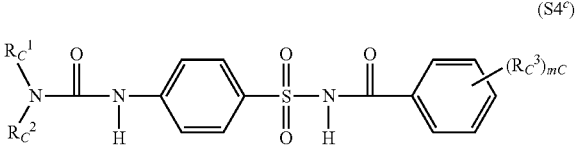

(S4$^c$)

in which $R_C^1$, $R_C^2$ are each independently hydrogen, $(C_1-C_8)$alkyl, $(C_3-C_8)$cycloalkyl, $(C_3-C_6)$alkenyl, $(C_3-C_6)$alkynyl, $R_C^3$ is halogen, $(C_1-C_4)$alkyl, $(C_1-C_4)$alkoxy, $CF_3$ $m_C$ is 1 or 2;

for example
1-[4-(N-2-methoxybenzoylsulfamoyl)phenyl]-3-methylurea,
1-[4-(N-2-methoxybenzoylsulfamoyl)phenyl]-3,3-dimethylurea,
1-[4-(N-4,5-dimethylbenzoylsulfamoyl)phenyl]-3-methylurea.

S5) Active ingredients from the class of hydroxyaromatics and aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active ingredients from the class of 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of diphenylmethoxyacetic acid derivatives (S7), e.g. methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8) as described in WO-A-98/27049

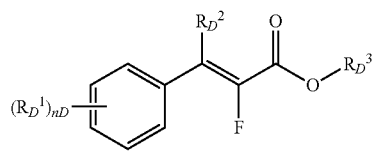

(S8)

in which the symbols and indices have the following meanings:
$R_D^1$ is halogen, $(C_1-C_4)$alkyl, $(C_1-C_4)$haloalkyl, $(C_1-C_4)$alkoxy, $(C_1-C_4)$haloalkoxy,
$R_D^2$ is hydrogen or $(C_1-C_4)$alkyl
$R_D^3$ is hydrogen, $(C_1-C_8)$alkyl, $(C_2-C_4)$alkenyl, $(C_2-C_4)$alkynyl, or aryl, where each of the aforementioned carbon-containing radicals is unsubstituted or substituted by one or more, preferably up to three, identical or different radicals from the group consisting of halogen and alkoxy; or salts thereof
$n_D$ is an integer from 0 to 2.

S9) Active ingredients from the class of 3-(5-tetrazolylcarbonyl)-2-quinolones (S9), e.g. 1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolyl-carbonyl)-2-quinolone (CAS Reg. No. 95855-00-8), as described in WO-A-1 999/000020.

S10) Compounds of the formulae (S10$^a$) and (S10$^b$) as described in WO-A-2007/023719 and WO-A-2007/023764

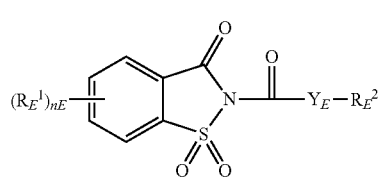

(S10$^a$)

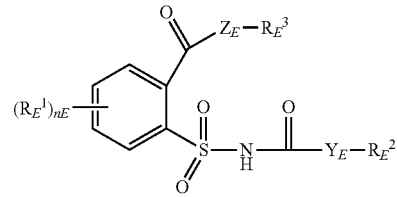

(S10$^b$)

in which
$R_E^1$ is halogen, $(C_1-C_4)$alkyl, methoxy, nitro, cyano, $CF_3$, $OCF_3$
$Y_E, Z_E$ are each independently O or S,
$n_E$ is an integer from 0 to 4,
$R_E^2$ is $(C_1-C_{16})$alkyl, $(C_2-C_6)$alkenyl, $(C_3-C_6)$cycloalkyl, aryl, benzyl, halobenzyl,
$R_E^3$ is hydrogen or $(C_1-C_6)$alkyl.

S11) Active ingredients of the oxyimino compound type (S11) which are known as seed dressings, for example "oxabetrinil" ((Z)-1,3-dioxolan-2-ylmethoxyimino(phenyl)acetonitrile) (S11-1), which is known as a seed dressing safener for barley to counter metolachlor damage, "fluxofenim" (1-(4-chlorophenyl)-2,2,2-trifluoro-1-ethanone O-(1,3-dioxolan-2-ylmethyl)oxime) (S11-2), which is known as a seed dressing safener for barley to counter metolachlor damage, and "cyometrinil" or "CGA-43089" ((Z)-cyanomethoxyimino(phenyl)acetonitrile) (S11-3), which is known as a seed dressing safener for barley to counter metolachlor damage.

S12) Active ingredients from the class of isothiochromanones (S12), for example methyl [(3-oxo-1H-2-benzothiopyran-4(3H)ylidene)methoxy]acetate (CAS Reg. No. 205121-04-6) (S12-1) and related compounds from WO-A-1998/13361.

S13) One or more compounds from group (S13):
"naphthalic anhydride" (1,8-naphthalinedicarboxylic anhydride) (S13-1), which is known as a seed dressing safener for corn to counter thiocarbamate herbicide damage,
"fenclorim" (4,6-dichloro-2-phenylpyrimidine) (S13-2), which is known as a safener for pretilachlor in sown rice,
"flurazole" (benzyl-2-chloro-4-trifluoromethyl-1,3-thiazole-5-carboxylate) (S13-3), which is known as a seed dressing safener for barley to counter alachlor and metolachlor damage,
"CL 304415" (CAS Reg. No. 31541-57-8) (4-carboxy-3,4-dihydro-2H-1-benzopyran-4-acetic acid) (S13-4) from American Cyanamid, which is known as a safener for corn to counter imidazolinone damage,
"MG 191" (CAS Reg. No. 96420-72-3) (2-dichloromethyl-2-methyl-1,3-dioxolane) (S13-5) from Nitrokemia, which is known as a safener for corn,
"MG-838" (CAS Reg. No. 133993-74-5) (2-propenyl 1-oxa-4-azaspiro[4.5]decane-4-carbodithioate) (S13-6) from Nitrokemia "disulfoton" (O,O-diethyl S-2-ethylthioethylphosphorodithioate) (S13-7), "dietholate" (O,O-diethyl O-phenylphosphorothioate) (S13-8), "mephenate" (4-chlorophenyl methylcarbamate) (S13-9).

S14) Active ingredients which, as well as a herbicidal effect against harmful plants, also have a safener effect on crop plants such as rice, for example "dimepiperate" or "MY-93" (S-1-methyl-1-phenylethyl piperidine-1-carbothioate), which is known as a safener for rice to counter damage by the herbicide molinate, "daimuron" or "SK 23" (1-(1-methyl-1-phenylethyl)-3-p-tolylurea), which is known as a safener for rice to counter damage by the herbicide imazosulfuron, "cumyluron"="JC-940" (3-(2-chlorophenylmethyl)-1-(1-methyl-1-phenylethyl)urea, see JP-A-60087254), which is known as a safener for rice to counter damage by a number of herbicides, "methoxyphenone" or "NK 049" (3,3'-dimethyl-4-methoxybenzophenone), which is known as a safener for rice to counter damage by a number of herbicides, "CSB" (1-bromo-4-(chloromethylsulfonyl)benzene) from Kumiai, (CAS Reg. No. 54091-06-4), which is known as a safener to counter damage by a number of herbicides in rice.

S15) Compounds of the formula (S15) or tautomers thereof as described in WO-A-2008/131861 and WO-A-2008/131860

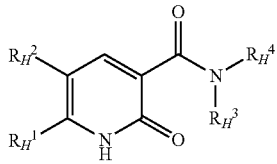

(S15)

in which
$R_H^1$ is a $(C_1$-$C_6)$haloalkyl radical and
$R_H^2$ is hydrogen or halogen and
$R_H^3$, $R_H^4$ are each independently hydrogen, $(C_1$-$C_{16})$alkyl, $(C_2$-$C_{16})$alkenyl or $(C_2$-$C_{16})$alkynyl,
  where each of the latter three radicals is unsubstituted or substituted by one or more radicals from the group of halogen, hydroxyl, cyano, $(C_1$-$C_4)$alkoxy, $(C_1$-$C_4)$haloalkoxy, $(C_1$-$C_4)$alkylthio, $(C_1$-$C_4)$alkylamino, di[$(C_1$-$C_4)$alkyl]-amino, [$(C_1$-$C_4)$haloalkoxy]-carbonyl, $(C_3$-$C_6)$cycloalkyl which is unsubstituted or substituted, phenyl which is unsubstituted or substituted, and heterocyclyl which is unsubstituted or substituted,
  or $(C_3$-$C_6)$cycloalkyl, $(C_4$-$C_6)$cycloalkenyl, $(C_3$-$C_6)$cycloalkyl fused on one side of the ring to a 4- to 6-membered saturated or unsaturated carbocyclic ring, or $(C_4$-$C_6)$cycloalkenyl fused on one side of the ring to a 4- to 6-membered saturated or unsaturated carbocyclic ring,
  where each of the 4 latter radicals is unsubstituted or substituted by one or more radicals from the group of halogen, hydroxyl, cyano, $(C_1$-$C_4)$alkyl, $(C_1$-$C_4)$haloalkyl, $(C_1$-$C_4)$alkoxy, $(C_1$-$C_4)$haloalkoxy, $(C_1$-$C_4)$alkylthio, $(C_1$-$C_4)$alkylamino, di[$(C_1$-$C_4)$alkyl]-amino, [$(C_1$-$C_4)$ alkoxy]-carbonyl, [$(C_1$-$C_4)$haloalkoxy]-carbonyl, $(C_3$-$C_6)$cycloalkyl which is unsubstituted or substituted, phenyl which is unsubstituted or substituted, and heterocyclyl which is unsubstituted or substituted,
  or
$R_H^3$ is $(C_1$-$C_4)$alkoxy, $(C_2$-$C_4)$alkenyloxy, $(C_2$-$C_6)$alkynyloxy or $(C_2$-$C_4)$haloalkoxy and
$R_H^4$ is hydrogen or $(C_1$-$C_4)$-alkyl or
$R_H^3$, $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1$-$C_4)$alkyl, $(C_1$-$C_4)$haloalkyl, $(C_1$-$C_4)$alkoxy, $(C_1$-$C_4)$haloalkoxy and $(C_1$-$C_4)$alkylthio.

S16) Active ingredients which are used primarily as herbicides but also have safener effect on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy) butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichloro-ethyl).

Some of the safeners are also known as herbicides and thus, in addition to herbicidal action toward weed plants, also display protective action toward the crop plants.

The weight ratios of herbicide (mixture) to safener depend generally on the herbicide application rate and the efficacy of the safener in question and may vary within wide limits, for example in the range from 200:1 to 1:200, preferably 100:1 to 1:100, especially 20:1 to 1:20. Analogously to the inventive compounds or mixtures thereof, the safeners can be formulated with further pesticides and be provided and employed as a finished formulation or tankmix with the inventive compounds.

For application, the formulations present in commercial standard form are, if appropriate, diluted in a customary manner, for example with water in the case of wettable powders, emulsifiable concentrates, dispersions and water-dispersible granules. Dust-type formulations, granules for soil application or granules for broadcasting and sprayable solutions are not normally diluted further with other inert substances prior to application.

The required application rate of the inventive compounds varies with the external conditions such as temperature, humidity and the type of herbicide used, among others. It can vary within wide limits, for example between 0.001 and 10.0 kg/ha or more of active substance, but it is preferably between 0.005 and 5 kg/ha.

EXAMPLES

The respective synthesis routes of compounds used, for example methyl 4-amino-6-bromo-3-chloropyridine-2-carboxylate, methyl 4-amino-3,6-dichloropyridine-2-carboxylate, methyl 4-amino-3,6-dichloro-5-fluoropyridine-2-carboxylate and 4-amino-6-bromo-3-chloropyridine-2-carboxylic acid, have already been described in patent specification U.S. Pat. No. 6,297,197.

General Synthesis Method (A):

Methyl 4-amino-6-bromo-3-chloropyridine-2-carboxylate or methyl 4-amino-3,6-dichloro-5-fluoropyridine-2-carboxylate (1.0 equivalent) and the particular 2-aminophenyl-1-boronic acid pinacol ester or the appropriate 2-aminophenyl-1-boronic acid (1.2 equivalents) are dissolved in dimethoxyethane (3 ml/mmol of the pyridine used), and aqueous sodium carbonate solution (2M, 1.5 eq.) is added. The reaction mixture is degassed with nitrogen, the Pd(PPh$_3$)$_4$ catalyst is added (0.05 equivalent), and the mixture is heated to 130° C. in a closed vessel in a microwave for hours. Subsequently, the mixture is admixed with ethyl acetate and water, and the organic phase is removed, dried over magnesium sulfate and concentrated under reduced pressure. The resulting crude product is purified chromatographically using silica gel with different eluents (preferably a mixture of ethyl acetate/n-heptane or methanol/dichloromethane) or recrystallized to obtain the pure product.

General Synthesis Method (B):

The respective 2-bromoaniline (1.8 equivalents), pinacoldiborane (3.0 equivalents), potassium acetate (9.0 equivalents)

and Pd(dppf)Cl*CH$_2$Cl$_2$ (0.05 equivalent) are suspended in 1,2-dimethoxyethane and degassed by introducing nitrogen. The mixture is heated in a closed vessel to 150° C. in a microwave for 20 minutes. Without further workup, methyl 4-amino-6-bromo-3-chloropyridine-2-carboxylate or methyl 4-amino-3,6-dichloro-5-fluoropyridine-2-carboxylate (1.0 equivalent), Pd(PPh$_3$)$_4$ (0.05 equivalent) and 2M aqueous sodium carbonate solution (2.5 equivalents) are then added. After degassing again with nitrogen, the mixture is heated in a closed vessel to 130° C. in a microwave for 2 hours. Subsequently, the reaction mixture is added to water and extracted with ethyl acetate. The organic phase is dried over magnesium sulfate and concentrated under reduced pressure. The resulting crude product is purified chromatographically using silica gel with different eluents (preferably a mixture of ethyl acetate/n-heptane or methanol/dichloromethane) and/or recrystallized to obtain the pure product.

General Synthesis Method (C):

The methyl ester obtained from synthesis method (A) or (B) (1.0 equivalent) is dissolved in tetrahydrofuran (3 ml/mmol of the methyl ester used) and sodium hydroxide solution (1.2 equivalents, 0.5 molar) is added. The mixture is stirred at room temperature for four hours and then acidified with 10% sulfuric acid. The mixture is extracted repeatedly with ethyl acetate, and the organic phases are dried with magnesium sulphate and concentrated under reduced pressure. The resulting crude product is purified by means of preparative HPLC or recrystallized to obtain the pure product.

A. Synthesis Examples and Physical Data

Syntheses of inventive compounds of the formula (I) are described by way of example hereinafter, though these examples do not have limiting character. Methods for the physical data reported: $^1$H NMR (Bruker DRX-400, 400 MHz, 294K, deuterated solvents as specified in each case, tetramethylsilane=0.0 ppm):

1. methyl 4-amino-6-(2-amino-4-chlorophenyl)-3-chloropyridine-2-carboxylate (ex. no. 58)
    The substance is prepared analogously to general synthesis method (A). The yield is 70%. $^1$H NMR (CDCl$_3$): δ 7.32 (d, 1H), 7.00 (s, 1H), 6.69 (m, 2H), 5.79 (bs, 2H), 4.82 (bs, 2H), 3.97 (s, 3H) ppm.
2. methyl 4-amino-6-(2-aminophenyl)-3-chloropyridine-2-carboxylate (ex. no. 2)
    The substance is prepared analogously to general synthesis method (A). The yield is 40%. $^1$H NMR (CDCl$_3$): δ 7.39 (d, 1H), 7.15 (dd, 1H), 7.03 (s, 1H), 6.73 (m, 2H), 5.59 (bs, 2H), 4.80 (bs, 2H), 3.97 (s, 3H) ppm.
3. methyl 4-amino-6-(2-amino-4-chlorophenyl)-3-chloro-5-fluoropyridine-2-carboxylate (ex. no. 62)
    The substance is prepared analogously to general synthesis method (A). The yield is 35%. $^1$H NMR (CDCl$_3$): δ 7.40 (m, 1H), 6.75 (m, 2H), 5.27 (bs, 2H), 4.93 (bs, 2H), 3.97 (s, 3H) ppm.
4. methyl 4-amino-6-(2-aminophenyl)-3-chloro-5-fluoropyridine-2-carboxylate (ex. no. 3)
    The substance is prepared analogously to general synthesis method (A). The yield is 28%. $^1$H NMR (CDCl$_3$): δ 7.44 (m, 1H), 7.19 (dd, 1H), 6.78 (m, 2H), 5.02 (bs, 2H), 4.92 (bs, 2H), 3.96 (s, 3H) ppm.
5. methyl 4-amino-6-[2-amino-4-(methoxycarbonyl)phenyl]-3-chloropyridine-2-carboxylate (ex. no. 90)
    The substance is prepared analogously to general synthesis method (A). The yield is 30%. $^1$H NMR ([D$_6$]-DMSO): δ 7.46 (d, 1H), 7.40 (s, 1H), 7.17 (m, 2H), 6.78 (bs, 2H), 6.56 (bs, 2H), 3.89 (s, 3H), 3.83 (s, 3H) ppm.
6. methyl 4-amino-6-[2-amino-4-(methoxycarbonyl)phenyl]-3-chloro-5-fluoropyridine-2-carboxylate (ex. no. 91)
    The substance is prepared analogously to general synthesis method (A). The yield is 19%. $^1$H NMR ([D$_6$]-DMSO): δ 7.41 (s, 1H), 7.30 (d, 1H), 7.17 (d, 1H), 6.97 (bs, 2H), 5.77 (bs, 2H), 3.86 (s, 3H), 3.84 (s, 3H) ppm.
7. methyl 4-amino-6-(2-amino-5-fluorophenyl)-3-chloropyridine-2-carboxylate (ex. no. 30)
    The substance is prepared analogously to general synthesis method (A). The yield is 63%. $^1$H NMR (CDCl$_3$): δ 7.10 (dd, 1H), 6.97 (m, 1H), 6.89 (m, 1H), 6.65 (dd, 1H), 5.40 (bs, 2H), 4.86 (bs, 2H), 3.97 (s, 3H) ppm.
8. 4-amino-6-(2-amino-4-chlorophenyl)-3-chloropyridine-2-carboxylic acid (ex. no. 371)
    The substance is prepared analogously to general synthesis method (C). The yield is 92%. $^1$H NMR ([D$_6$]-DMSO): δ 7.32 (d, 1H), 7.00 (s, 1H), 6.76 (d, 1H), 6.60 (dd, 1H), 6.50 (bs, 2H) ppm.
9. 4-amino-6-(2-amino-4-chlorophenyl)-3-chloro-5-fluoropyridine-2-carboxylic acid (ex. no. 375)
    The substance is prepared analogously to general synthesis method (C). The yield is 56%. $^1$H NMR ([D$_6$]-DMSO): δ 7.22 (dd, 1H), 6.86 (bs, 2H), 6.82 (dd, H), 6.62 (dd, 1H).
10. methyl 4-amino-6-[2-amino-3-methoxy-4-chlorophenyl]-3-chloropyridine-2-carboxylate (ex. no. 202)
    The substance is prepared analogously to general synthesis method (A). The yield is 30%. $^1$H NMR (CDCl$_3$): δ 7.13 (d, 1H), 7.02 (s, 1H), 6.69 (d, 1H), 4.88 (bs, 4H), 3.99 (s, 3H), 3.88 (s, 3H) ppm.
11. methyl 4-amino-6-(2-amino-4,5-dichlorophenyl)-3-chloropyridine-2-carboxylate (ex. no. 174)
    The substance is prepared analogously to general synthesis method (A). The yield is 8%. $^1$H NMR (CDCl$_3$): δ 7.48 (s, 1H), 7.01 (s, 1H), 6.82 (s, 1H), 4.87 (bs, 2H), 3.98 (s, 3H) ppm.
12. methyl-4-amino-6-(2-amino-4,6-difluorophenyl)-3-chloropyridine-2-carboxylate (ex. no. 139)
    The substance is prepared analogously to general synthesis method (A). The yield is 15%. $^1$H NMR (CDCl$_3$): δ 6.83 (s, 1H), 6.24 (m, 2H), 4.77 (bs, 2H), 3.97 (s, 3H) ppm.
13. methyl 4-amino-6-(2-amino-3,5-difluorophenyl)-3-chloropyridine-2-carboxylate (ex. no. 167)
    The substance is prepared analogously to general synthesis method (A). The yield is 18%. $^1$H NMR (CDCl$_3$): δ 6.99 (s, 1H), 6.97 (m, 1H), 6.83 (m, 1H), 5.56 (bs, 2H), 4.88 (bs, 2H), 3.99 (s, 3H) ppm.
14. Methyl 4-amino-6-(2-amino-3-chloro-6-fluorophenyl)-3-chloropyridine-2-carboxylate (Ex. No. 627)
    The substance is prepared analogously to general synthesis method (A).
    The yield is 50%. $^1$H NMR (CDCl$_3$): δ 7.20 (dd, 1H), 7.03 (d, 1H), 6.44 (dd, 1H), 4.88 (bs, 2H), 3.98 (s, 3H) ppm.
15. Methyl 4-amino-6-(2-amino-4,5,6-trifluorophenyl)-3-chloropyridine-2-carboxylate (Ex. No. 628)
    The substance is prepared analogously to general synthesis method (B).
    The yield is 29%. $^1$H NMR (CDCl$_3$): δ 7.00 (d, 1H), 6.30 (m, 1H), 4.88 (bs, 2H), 3.98 (s, 3H) ppm.
16. Methyl 4-amino-6-(2-amino-5-chlorophenyl)-3-chloropyridine-2-carboxylate (Ex. No. 37)
    The substance is prepared analogously to general synthesis method (A).
    The yield is 54%. $^1$H NMR (CDCl$_3$): δ 7.37 (d, 1H), 7.10 (dd, 1H), 7.01 (s, 1H), 6.65 (d, 1H), 5.64 (bs, 2H), 4.85 (bs, 2H), 3.97 (s, 3H) ppm.

17. Methyl 4-amino-6-(2-amino-3-fluorophenyl)-3-chloropyridine-2-carboxylate (Ex. No. 97)
   The substance is prepared analogously to general synthesis method (A).
   The yield is 28%. $^1$H NMR (CDCl$_3$): δ 7.19 (d, 1H), 7.03 (s, 1H), 6.99 (m, 1H), 6.63 (m, 1H), 5.77 (bs, 2H), 4.85 (bs, 2H), 3.98 (s, 3H) ppm.

18. Methyl 4-amino-6-(2-amino-5-methylphenyl)-3-chloropyridine-2-carboxylate (Ex. No. 629)
   The substance is prepared analogously to general synthesis method (B).
   The yield is 15%. $^1$H NMR (CDCl$_3$): δ 7.20 (d, 1H), 7.04 (s, 1H), 6.97 (dd, 1H), 6.65 (d, 1H), 5.40 (bs, 2H), 4.80 (bs, 2H), 3.97 (s, 3H), 2.26 (s, 3H) ppm.

19. Methyl 4-amino-6-(2-amino-4-chloro-5-methoxyphenyl)-3-chloropyridine-2-carboxylate (Ex. No. 630)
   The substance is prepared analogously to general synthesis method (A).
   The yield is 11%. $^1$H NMR (CDCl$_3$): δ 6.98 (s, 1H), 6.97 (s, 1H), 6.79 (s, 1H), 5.30 (bs, 2H), 4.87 (bs, 2H), 3.98 (s, 3H), 3.86 (s, 3H) ppm.

20. Methyl 4-amino-6-(2-amino-4,5-difluorophenyl)-3-chloropyridine-2-carboxylate (Ex. No. 160)
   The substance is prepared analogously to general synthesis method (B).
   The yield is 30%. $^1$H NMR (CDCl$_3$): δ 7.23 (m, 1H), 7.04 (s, 1H), 6.52 (m, 1H), 5.77 (bs, 2H), 5.53 (bs, 2H), 3.96 (s, 3H) ppm.

21. Methyl 4-amino-6-(2-amino-3,4,5-trichlorophenyl)-3-chloro-5-fluorpyridine-2-carboxylate (Ex. No. 631)
   Methyl 4-amino-6-(2-amino-4-chlorophenyl)-3-chloro-5-fluorpyridine-2-carboxylate (Ex. No. 62) is dissolved in acetonitrile, and N-chlorosuccinimide (3.0 equivalents) is added. The mixture is boiled under reflux for two hours, added to diethyl ether and then washed with water. The organic phase is dried over magnesium sulfate, concentrated and filtered through silica gel, and the crystals obtained are washed with a little diethyl ether.
   The yield is 64%. $^1$H NMR (CDCl$_3$): δ 7.54 (s, 1H), 5.90 (bs, 2H), 5.01 (bs, 2H), 3.98 (s, 3H) ppm.

22. Methyl 4-amino-6-(2-amino-3-fluoro-5-methylphenyl)-3-chloropyridine-2-carboxylate (Ex. No. 632)
   The substance is prepared analogously to general synthesis method (B).
   The yield is 37%. $^1$H NMR (CDCl$_3$): δ 7.02 (s, 1H), 7.00 (s, 1H), 6.84 (d, 1H), 5.53 (bs, 2H), 4.83 (bs, 2H), 3.98 (s, 3H), 2.26 (s, 3H) ppm.

23. Methyl 4-amino-6-(2-amino-3-fluoro-5-chlorophenyl)-3-chloropyridine-2-carboxylate (Ex. No. 633)
   The substance is prepared analogously to general synthesis method (B).
   The yield is 50%. $^1$H NMR (CDCl$_3$): δ 7.22 (m, 1H), 7.03 (m, 2H), 5.81 (bs, 2H), 4.89 (bs, 2H), 3.99 (s, 3H) ppm.

24. Methyl 4-amino-6-(2-amino-4-nitrophenyl)-3-chloropyridine-2-carboxylate (Ex. No. 634)
   The substance is prepared analogously to general synthesis method (B).
   The yield is 31%. $^1$H NMR (CDCl$_3$): δ 7.55 (s, 1H), 7.53 (m, 2H), 7.08 (s, 1H), 6.02 (bs, 2H), 4.94 (bs, 2H), 4.00 (s, 3H) ppm.

25. Methyl 4-amino-6-(2-amino-5-methoxyphenyl)-3-chloropyridine-2-carboxylate (Ex. No. 44)
   The substance is prepared analogously to general synthesis method (B).
   The yield is 25%. $^1$H NMR ([D$_6$]-DMSO): δ 9.70 (bs, 2H), 7.72 (d, 1H), 7.44 (s, H), 7.33 (dd, 1H), 7.24 (d, 1H), 6.78 (bs, 1H), 3.88 (s, 3H) ppm.

26. Methyl 4-amino-6-(2-amino-3-methyl-5-chlorophenyl)-3-chloropyridine-2-carboxylate (Ex. No. 635)
   The substance is prepared analogously to general synthesis method (B).
   The yield is 51%. $^1$H NMR (CDCl$_3$): δ 7.26 (d, 1H), 7.05 (d, 1H), 7.00 (s, 1H), 5.64 (bs, 2H), 4.85 (bs, 2H), 3.98 (s, 3H), 2.17 (s, 3H) ppm.

27. Methyl 4-amino-6-(2-amino-4-chloro-5-methylphenyl)-3-chloropyridine-2-carboxylate (Ex. No. 636)
   The substance is prepared analogously to general synthesis method (B).
   The yield is 20%. $^1$H NMR (CDCl$_3$): δ 7.23 (s, 1H), 7.00 (s, 1H), 6.74 (s, 1H), 5.55 (bs, 2H), 4.82 (bs, 2H), 3.97 (s, 3H), 2.27 (s, 3H) ppm.

28. Methyl 4-amino-6-(2-amino-4-methoxyphenyl)-3-chloropyridine-2-carboxylate (Ex. No. 83)
   The substance is prepared analogously to general synthesis method (B).
   The yield is 9%. $^1$H NMR ([D$_6$]-DMSO): δ 7.32 (d, 1H), 7.08 (s, 1H), 6.72 (bs, 2H), 6.34 (m, 2H), 3.88 (s, 3H), 3.72 (s, 3H) ppm.

29. Methyl 4-amino-6-(2-amino-5-cyanophenyl)-3-chloropyridine-2-carboxylate (Ex. No. 637)
   The substance is prepared analogously to general synthesis method (B).
   The yield is 31%. $^1$H NMR (CDCl$_3$): δ 8.29 (s, 1H), 7.38 (d, 1H), 7.06 (s, 1H), 6.69 (d, 1H), 6.40 (bs, 2H), 4.92 (bs, 2H), 3.99 (s, 3H) ppm.

30. Methyl 4-amino-6-(2-amino-3-chloro-5-fluorophenyl)-3-chloropyridine-2-carboxylate (Ex. No. 638)
   The substance is prepared analogously to general synthesis method (B).
   The yield is 34%. $^1$H NMR (CDCl$_3$): δ 7.08 (m, 2H), 6.98 (s, 1H), 5.95 (bs, 2H), 4.89 (bs, 2H), 3.99 (s, 3H) ppm.

31. Methyl 4-amino-6-(2-amino-3-fluoro-5-chlorophenyl)-3,5-dichloropyridine-2-carboxylate (Ex. No. 639)
   Methyl 4-amino-6-(2-amino-3-chloro-5-fluorophenyl)-3-chloropyridine-2-carboxylate (Ex. No. 638) is dissolved in acetonitrile, and N-chlorosuccinimide (1.1 equivalent) is added. The mixture is stirred at room temperature for 48 hours, added to ethyl acetate and then washed with water. The organic phase is dried over magnesium sulfate, concentrated and purified by chromatography.
   The yield is 50%. $^1$H NMR (CDCl$_3$): δ 7.14 (s, 1H), 7.07 (d, 1H), 5.14 (bs, 2H), 3.97 (s, 3H) ppm.

32. Methyl 4-amino-6-(2-amino-3-fluoro-5-chlorophenyl)-3-chloro-5-fluoropyridine-2-carboxylate (Ex. No. 640)
   The substance is prepared analogously to general synthesis method (B).
   The yield is 21%. $^1$H NMR (CDCl$_3$): δ 7.31 (d, 1H), 7.07 (dd, 1H), 5.30 (bs, 2H), 4.98 (bs, 2H), 3.97 (s, 3H) ppm.

33. Methyl 4-amino-6-(2-amino-3,5-difluoro-4-chlorophenyl)-3-chloropyridine-2-carboxylate (Ex. No. 280)
   The substance is prepared analogously to general synthesis method (A).
   The yield is 8%. $^1$H NMR (CDCl$_3$): δ 7.09 (d, 1H), 6.99 (s, 1H), 5.75 (bs, 2H), 4.90 (bs, 2H), 3.99 (s, 3H) ppm.

34. Methyl 4-amino-6-(2-amino-4-fluorophenyl)-3-chloropyridine-2-carboxylate (Ex. No. 51)
   The substance is prepared analogously to general synthesis method (B).
   The yield is 27%. $^1$H NMR (CDCl$_3$): δ 7.35 (dd, 1H), 6.97 (s, 1H), 6.41 (m, 2H), 5.82 (bs, 2H), 4.82 (bs, 2H), 3.97 (s, 3H) ppm.

35. Methyl 4-amino-6-(2-amino-3,4,5-trichlorophenyl)-3-chloropyridine-2-carboxylate (Ex. No. 641)

The substance is prepared analogously to general synthesis method (B).

The yield is 44%. $^1$H NMR ([D$_6$]-DMSO): δ 7.59 (s, 1H), 7.20 (s, 1H), 6.94 (bs, 2H), 6.84 (bs, 2H), 3.88 (s, 3H) ppm.

36. Methyl 4-amino-6-(2,4-diamino-3-chloro-5-fluorophenyl)-3-chloropyridine-2-carboxylate (Ex. No. 642)

The substance is prepared analogously to general synthesis method (B).

The yield is 5%. $^1$H NMR (CDCl$_3$): δ 7.10 (d, 1H), 6.91 (s, 1H), 6.22 (bs, 2H), 4.80 (bs, 2H), 4.22 (bs, 2H), 3.98 (s, 3H) ppm.

37. Methyl 4-amino-6-(2-amino-4-(trifluoromethyl)phenyl)-3-chloropyridine-2-carboxylate (Ex. No. 643)

The substance is prepared analogously to general synthesis method (B).

The yield is 37%. $^1$H NMR (CDCl$_3$): δ 7.48 (d, 1H), 7.05 (s, 1H), 6.93 (m, 2H), 5.82 (bs, 2H), 4.88 (bs, 2H), 3.98 (s, 3H) ppm.

38. Methyl 4-amino-6-(2-amino-3-chloro-5-cyanophenyl)-3-chloropyridine-2-carboxylate (Ex. No. 644)

The substance is prepared analogously to general synthesis method (B).

The yield is 23%. $^1$H NMR (CDCl$_3$): δ 7.74 (d, 1H), 7.68 (d, 1H), 7.07 (s, 1H), 7.05 (bs, 2H), 4.97 (bs, 2H), 4.00 (s, 3H) ppm.

39. Methyl 4-amino-6-(2-amino-4-fluoro-5-chlorophenyl)-3-chloropyridine-2-carboxylate (Ex. No. 645)

The substance is prepared analogously to general synthesis method (B).

The yield is 40%. $^1$H NMR (CDCl$_3$): δ 7.43 (d, 1H), 7.04 (s, 1H), 6.51 (d, 1H), 5.93 (bs, 2H), 5.21 (bs, 2H), 3.97 (s, 3H) ppm.

40. Methyl 4-amino-6-(2-amino-3-chloro-4-nitrophenyl)-3-chloropyridine-2-carboxylate (Ex. No. 646)

The substance is prepared analogously to general synthesis method (B).

The yield is 38%. $^1$H NMR (CDCl$_3$): δ 7.46 (d, 1H), 7.13 (m, 2H), 6.71 (bs, 2H), 5.50 (bs, 2H), 3.99 (s, 3H) ppm.

41. Methyl 4-amino-6-(2-amino-3,5-dichloro-4-nitrophenyl)-3-chloropyridine-2-carboxylate (Ex. No. 647)

The substance is prepared analogously to general synthesis method (B).

The yield is 10%. $^1$H NMR (CDCl$_3$): δ 7.48 (s, 1H), 7.04 (s, 1H), 6.67 (bs, 2H), 4.98 (bs, 2H), 4.00 (s, 3H) ppm.

42. Methyl 4-amino-6-(2-amino-4-(trifluoromethyl)-5-chlorophenyl)-3-chloropyridine-2-carboxylate (Ex. No. 648)

The substance is prepared analogously to general synthesis method (B).

The yield is 28%. $^1$H NMR (CDCl$_3$): δ 7.51 (s, 1H), 7.05 (s, 1H), 7.01 (s, 1H), 6.42 (bs, 2H), 4.92 (bs, 2H), 3.99 (s, 3H) ppm.

43. Methyl 4-amino-6-(2-amino-4-(trifluoromethyl)-5-chlorophenyl)-3,5-dichloropyridine-2-carboxylate (Ex. No. 649)

Methyl 4-amino-6-(2-amino-4-(trifluoromethyl)-5-chlorophenyl)-3-chloropyridine-2-carboxylate (Ex. No. 648) is dissolved in tetrahydrofuran, and N-chlorosuccinimide (2.0 equivalents) is added. The mixture is stirred at room temperature for 48 hours, added to ethyl acetate and then washed with water. The organic phase is dried over magnesium sulfate, concentrated and purified by chromatography. The yield is 34%. $^1$H NMR (CDCl$_3$): δ 7.46 (s, 1H), 7.05 (s, 1H), 6.59 (bs, 2H), 4.97 (bs, 2H), 4.00 (s, 3H) ppm.

44. Methyl 4-amino-6-(2-amino-6-fluorophenyl)-3-chloropyridine-2-carboxylate (Ex. No. 9)

The substance is prepared analogously to general synthesis method (B).

The yield is 53%. $^1$H NMR (CDCl$_3$): δ 7.05 (m, 2H), 6.47 (m, 2H), 5.21 (bs, 2H), 4.84 (bs, 2H), 3.97 (s, 3H) ppm.

45. Methyl 4-amino-6-(2-amino-3,5-dichloro-4-methylphenyl)-3-chloropyridine-2-carboxylate (Ex. No. 650)

The substance is prepared analogously to general synthesis method (B).

The yield is 27%. $^1$H NMR ([D$_6$]-DMSO): δ 7.44 (s, 1H), 7.20 (s, 1H), 6.79 (bs, 2H), 6.68 (bs, 2H), 3.91 (s, 3H), 2.42 (s, 3H) ppm.

46. Methyl 4-amino-6-(2-amino-4-chloro-6-fluorophenyl)-3-chloropyridine-2-carboxylate (Ex. No. 132)

The substance is prepared analogously to general synthesis method (A).

The yield is 11%. $^1$H NMR (CDCl$_3$): δ 7.02 (d, 1H), 6.50 (m, 2H), 5.42 (bs, 2H), 4.85 (bs, 2H), 3.97 (s, 3H).

47. Methyl 4-amino-6-(2-amino-4-fluoro-5-methoxyphenyl)-3-chloropyridine-2-carboxylate (Ex. No. 651)

The substance is prepared analogously to general synthesis method (B).

The yield is 9%. $^1$H NMR (CDCl$_3$): δ 7.02 (d, 1H), 6.96 (s, 1H), 6.48 (d, 1H), 4.83 (bs, 2H), 3.97 (s, 3H), 3.85 (s, 3H).

48. Methyl 4-amino-6-(2-amino-4-methyl-5-fluorophenyl)-3-chloropyridine-2-carboxylate (Ex. No. 652)

The substance is prepared analogously to general synthesis method (B).

The yield is 16%. $^1$H NMR (CDCl$_3$): δ 7.06 (d, 1H), 6.96 (s, 1H), 6.52 (d, 1H), 5.43 (bs, 2H), 4.82 (bs, 2H), 3.97 (s, 3H), 2.21 (s, 3H).

49. Methyl 4-amino-6-(2-amino-3,4,5-trifluorphenyl)-3-chloropyridine-2-carboxylate (Ex. No. 653)

The substance is prepared analogously to general synthesis method (B).

The yield is 10%. $^1$H NMR (CDCl$_3$): δ 7.08 (m, 1H), 6.94 (s, 1H), 5.78 (bs, 2H), 4.90 (bs, 2H), 3.99 (s, 3H).

50. Methyl 4-amino-6-(2-amino-5,6-difluorophenyl)-3-chloropyridine-2-carboxylate (Ex. No. 654)

The substance is prepared analogously to general synthesis method (B).

The yield is 30%. $^1$H NMR (CDCl$_3$): δ 7.02 (d, 1H), 6.97 (dd, 1H), 6.42 (m, 1H), 4.99 (bs, 2H), 4.88 (bs, 2H), 3.97 (s, 3H).

51. Methyl 4-amino-6-(2-amino-3-chloro-5-nitrophenyl)-3-chloropyridine-2-carboxylate (Ex. No. 655)

The substance is prepared analogously to general synthesis method (B).

The yield is 66%. $^1$H NMR ([D$_6$]-DMSO): δ 8.31 (d, 1H), 8.21 (d, 1H), 8.04 (bs, 2H), 7.36 (s, 1H), 6.92 (bs, 2H), 3.91 (s, 3H).

52. Methyl 4-amino-6-(2-amino-4-chloro-5-fluorophenyl)-3-chloropyridine-2-carboxylate (Ex. No. 153)

The substance is prepared analogously to general synthesis method (B).

The yield is 26%. $^1$H NMR (CDCl$_3$): δ 7.19 (d, 1H), 6.96 (s, 1H), 6.73 (d, 1H), 5.59 (bs, 2H), 4.87 (bs, 2H), 3.98 (s, 3H).

53. Methyl 4-amino-6-(2-amino-3,5-difluoro-4-methoxyphenyl)-3-chloropyridine-2-carboxylate (Ex. No. 656)

The substance is prepared analogously to general synthesis method (B).

The yield is 41%. $^1$H NMR (CDCl$_3$): δ 7.00 (dd, 1H), 6.94 (s, 1H), 5.68 (bs, 2H), 4.86 (bs, 2H), 4.04 (s, 3H), 3.98 (s, 3H).

54. Methyl 4-amino-6-(2-amino-4-(trifluoromethyl)-5-fluorophenyl)-3-chloropyridine-2-carboxylate (Ex. No. 657)

The substance is prepared analogously to general synthesis method (B).

The yield is 35%. $^1$H NMR (CDCl$_3$): δ 7.23 (d, 1H), 7.00 (s, 1H), 6.89 (d, 1H), 5.67 (bs, 2H), 4.92 (bs, 2H), 3.99 (s, 3H).

55. Methyl 4-amino-6-(2-amino-3-methyl-5-fluorophenyl)-3-chloropyridine-2-carboxylate (Ex. No. 658)

The substance is prepared analogously to general synthesis method (B).

The yield is 21%. $^1$H NMR (CDCl$_3$): δ 6.99 (dd, 1H), 6.97 (s, 1H), 6.85 (dd, 1H), 5.41 (bs, 2H), 4.85 (bs, 2H), 3.98 (s, 3H), 2.19 (s, 3H).

56. Methyl 4-amino-6-(2-amino-3-(trifluoromethyl)-5-fluorophenyl)-3-chloropyridine-2-carboxylate (Ex. No. 659)

The substance is prepared analogously to general synthesis method (B).

The yield is 18%. $^1$H NMR (CDCl$_3$): δ 7.28 (dd, 1H), 7.22 (dd, 1H), 6.96 (s, 1H), 6.07 (bs, 2H), 4.94 (bs, 2H), 3.99 (s, 3H).

57. Methyl 4-amino-6-(2-amino-3-methyl-5-nitrophenyl)-3-chloropyridine-2-carboxylate (Ex. No. 660)

The substance is prepared analogously to general synthesis method (B).

The yield is 36%. $^1$H NMR ([D$_6$]-DMSO): δ 8.25 (d, 1H), 7.96 (d, 1H), 7.72 (bs, 2H), 7.33 (s, 1H), 6.85 (bs, 2H), 3.90 (s, 3H), 2.22 (s, 3H).

58. Methyl 4-amino-6-(2-amino-5-nitrophenyl)-3-chloropyridine-2-carboxylate (Ex. No. 661)

The substance is prepared analogously to general synthesis method (B).

The yield is 19%. $^1$H NMR ([D$_6$]-DMSO): δ 8.33 (d, 1H), 7.99 (dd, 1H), 7.91 (bs, 2H), 7.33 (s, 1H), 6.84 (m, 3H), 3.90 (s, 3H).

59. Methyl 4-amino-6-(2-amino-4-fluoro-5-methylphenyl)-3-chloropyridine-2-carboxylate (Ex. No. 662)

The substance is prepared analogously to general synthesis method (B).

The yield is 17%. $^1$H NMR (CDCl$_3$): δ 7.20 (d, 1H), 6.98 (s, 1H), 6.39 (d, 1H), 5.60 (bs, 2H), 4.81 (bs, 2H), 3.97 (s, 3H), 2.17 (s, 3H).

60. Methyl 4-amino-6-(2-amino-4-methoxy-5-methylphenyl)-3-chloropyridine-2-carboxylate (Ex. No. 663)

By using tert-butyl [5-methoxy-4-methyl-2-(4,4,5,5-tetramethyl-1,3,2-dioxaborolan-2-yl)phenyl]carbamate, analogously to general synthesis method (A), the Boc-protected derivative is first prepared. The yield of this Suzuki coupling is 51%. The subsequent removal of the Boc protecting group is effected by dissolving the crude product in dichloromethane, adding trifluoroacetic acid, then neutralizing by means of aqueous sodium hydrogencarbonate solution and extraction from the aqueous phase. Recrystallization is effected from ethyl acetate/heptane. The yield here is 63%. $^1$H NMR (CDCl$_3$): δ 7.18 (s, 1H), 6.99 (s, H), 6.18 (s, 1H), 5.72 (bs, 2H), 4.76 (bs, 2H), 3.97 (s, 3H), 3.81 (s, 3H).

61. Methyl 4-amino-6-(2-amino-5-(trifluoromethoxy)phenyl)-3-chloropyridine-2-carboxylate (Ex. No. 664)

The substance is prepared analogously to general synthesis method (B).

The yield is 19%. $^1$H NMR (CDCl$_3$): δ 7.26 (s, 1H), 7.03 (m, 1H), 7.00 (s, 1H), 6.69 (d, 1H), 5.68 (bs, 2H), 4.88 (bs, 2H), 3.98 (s, 3H).

62. Methyl 4-amino-6-(2-amino-3-nitro-5-fluorophenyl)-3-chloropyridine-2-carboxylate (Ex. No. 665)

The substance is prepared analogously to general synthesis method (B).

The yield is 15%. $^1$H NMR ([D$_6$]-DMSO): δ 8.08 (bs, 2H), 7.94 (dd, 1H), 7.70 (dd, H), 7.14 (s, 1H), 6.92 (bs, 2H), 3.89 (s, 3H).

63. Methyl 4-amino-6-(2-amino-3-nitro-5-methylphenyl)-3-chloropyridine-2-carboxylate (Ex. No. 666)

The substance is prepared analogously to general synthesis method (B).

The yield is 21%. $^1$H NMR ([D$_6$]-DMSO): δ 8.06 (bs, 2H), 7.95 (s, 1H), 7.58 (s, H), 7.13 (s, 1H), 6.90 (bs, 2H), 3.89 (s, 3H), 2.27 (s, 3H).

64. Methyl 4-amino-6-(2-amino-4,5-dimethylphenyl)-3-chloropyridine-2-carboxylate (Ex. No. 667)

The substance is prepared analogously to general synthesis method (B).

The yield is 24%. $^1$H NMR (CDCl$_3$): δ 7.16 (s, 1H), 7.03 (s, 1H), 6.54 (s, 1H), 5.46 (bs, 2H), 4.78 (bs, 2H), 3.96 (s, 3H), 2.19 (s, 3H), 2.18 (s, 3H).

65. Methyl 4-amino-6-(2-amino-3-chloro-5,6-dimethylphenyl)-3-chloropyridine-2-carboxylate (Ex. No. 668)

The substance is prepared analogously to general synthesis method (B).

The yield is 14%. $^1$H NMR (CDCl$_3$): δ 7.12 (s, 1H), 7.02 (s, 1H), 6.08 (bs, 2H), 4.82 (bs, 2H), 3.98 (s, 3H), 2.33 (s, 3H), 2.24 (s, 3H).

66. Methyl 4-amino-6-(2-amino-4-chloro-5,6-dimethylphenyl)-3-chloropyridine-2-carboxylate (Ex. No. 669)

The substance is prepared analogously to general synthesis method (B).

The yield is 13%. $^1$H NMR (CDCl$_3$): δ 7.07 (s, 1H), 6.68 (s, 1H), 4.87 (bs, 2H), 4.04 (bs, 2H), 3.97 (s, 3H), 2.16 (s, 3H), 1.96 (s, 3H).

67. Methyl 4-amino-6-(2-amino-3,5-dimethylphenyl)-3-chloropyridine-2-carboxylate (Ex. No. 670)

The substance is prepared analogously to general synthesis method (B).

The yield is 33%. $^1$H NMR (CDCl$_3$): δ 7.07 (s, 1H), 7.02 (s, 1H), 6.92 (s, 1H), 5.40 (bs, 2H), 4.81 (bs, 2H), 3.97 (s, 3H), 2.24 (s, 3H), 2.18 (s, 3H).

68. Methyl 4-amino-6-(2-amino-3,4,6-trifluorophenyl)-3-chloropyridine-2-carboxylate (Ex. No. 671)

The substance is prepared analogously to general synthesis method (B).

The yield is 3%. $^1$H NMR (CDCl$_3$): δ 6.83 (s, 1H), 6.34 (m, 1H), 4.82 (bs, 2H), 3.98 (s, 3H).

69. Methyl 4-amino-6-(2-amino-3,4-dichloro-5-fluorophenyl)-3-chloropyridine-2-carboxylate (Ex. No. 672)

The substance is prepared analogously to general synthesis method (B).

The yield is 11%. $^1$H NMR ([D$_6$]-DMSO): δ 7.47 (d, 1H), 7.16 (s, 1H), 6.86 (bs, 2H), 6.64 (bs, 2H), 3.89 (s, 3H).

70. Methyl 4-amino-6-(2-amino-3-(methoxycarbonyl)-5-methylphenyl)-3-chloropyridine-2-carboxylate (Ex. No. 673)

The substance is prepared analogously to general synthesis method (B).

The yield is 16%. $^1$H NMR (CDCl$_3$): δ 7.76 (d, 1H), 7.34 (d, 1H), 7.00 (s, 1H), 4.87 (bs, 2H), 3.98 (s, 3H), 3.87 (s, 3H), 2.25 (s, 3H).

71. Methyl 4-amino-6-(2-amino-3-chloro-5-(trifluoromethyl)phenyl)-3-chloropyridine-2-carboxylate (Ex. No. 674)

The substance is prepared analogously to general synthesis method (B).

The yield is 30%. ¹H NMR (CDCl₃): δ 7.60 (s, 1H), 7.54 (s, 1H), 7.09 (s, 1H), 6.71 (bs, 2H), 4.94 (bs, 2H), 4.00 (s, 3H).

72. Methyl 4-amino-6-(2-amino-5-(trifluoromethyl)phenyl)-3-chloropyridine-2-carboxylate (Ex. No. 675)

The substance is prepared analogously to general synthesis method (B).

The yield is 19%. ¹H NMR (CDCl₃): δ 7.66 (s, 1H), 7.36 (d, 1H), 7.08 (s, 1H), 6.74 (d, 1H), 6.10 (bs, 2H), 4.90 (bs, 2H), 3.98 (s, 3H).

73. Methyl 4-amino-6-(2-amino-3-nitro-5-(trifluoromethyl)phenyl)-3-chloropyridine-2-carboxylate (Ex. No. 676)

The substance is prepared analogously to general synthesis method (B).

The yield is 31%. ¹H NMR (CDCl₃): δ 8.95 (bs, 2H), 8.53 (s, 1H), 7.84 (s, 1H), 7.09 (s, 1H), 5.04 (bs, 2H), 4.02 (s, 3H).

74. Methyl 4-amino-6-(2-amino-4,5-(difluoromethylenedioxy)phenyl)-3-chloropyridine-2-carboxylate (Ex. No. 677)

The substance is prepared analogously to general synthesis method (B).

The yield is 20%. ¹H NMR (CDCl₃): δ 7.07 (s, 1H), 6.91 (s, 1H), 6.45 (s, 1H), 5.70 (bs, 2H), 4.87 (bs, 2H), 3.98 (s, 3H).

75. Methyl 4-amino-6-(2-amino-4-(trifluoromethoxy)phenyl)-3-chloropyridine-2-carboxylate (Ex. No. 678)

The substance is prepared analogously to general synthesis method (B).

The yield is 14%. ¹H NMR (CDCl₃): δ 7.39 (d, 1H), 7.00 (s, 1H), 6.56 (m, 2H), 5.82 (bs, 2H), 4.87 (bs, 2H), 3.98 (s, 3H).

76. Methyl 4-amino-6-(2-amino-3-(trifluoromethyl)-5-chlorophenyl)-3-chloropyridine-2-carboxylate (Ex. No. 679)

The substance is prepared analogously to general synthesis method (B).

The yield is 51%. ¹H NMR (CDCl₃): δ 7.51 (d, 1H), 7.45 (d, 1H), 7.00 (s, 1H), 6.32 (bs, 2H), 4.94 (bs, 2H), 3.99 (s, 3H).

77. Methyl 4-amino-6-(2-amino-4-methylphenyl)-3-chloropyridine-2-carboxylate (Ex. No. 680)

The substance is prepared analogously to general synthesis method (B).

The yield is 24%. ¹H NMR (CDCl₃): δ 7.29 (d, 1H), 7.01 (s, 1H), 6.54 (m, 2H), 5.62 (bs, 2H), 4.79 (bs, 2H), 3.97 (s, 3H), 2.27 (s, 3H).

78. Methyl 4-amino-6-(2-amino-4-cyanophenyl)-3-chloropyridine-2-carboxylate (Ex. No. 681)

The substance is prepared analogously to general synthesis method (B).

The yield is 23%. ¹H NMR (CDCl₃): δ 7.46 (d, 1H), 7.04 (s, 1H), 6.97 (m, 2H), 5.89 (bs, 2H), 4.93 (bs, 2H), 3.99 (s, 3H).

The compounds described in tables 1-3 below are obtained analogously to the synthesis examples described above.

In tables 1-3:

Me=methyl

Ac=acetyl

Vin=vinyl

TABLE 1 compounds of the formula (I) where R' = methyl

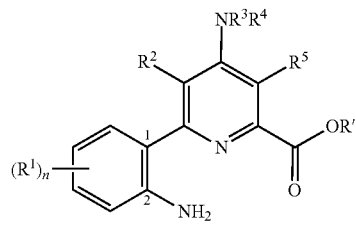

in which, by definition, the amino group in the phenyl radical is always fixed at the 2 position irrespective of the priority of further R¹ substituents.

| Ex. no. | R¹ | R² | R³ | R⁴ | R⁵ |
|---|---|---|---|---|---|
| 1. | — | H | H | H | F |
| 2. | — | H | H | H | Cl |
| 3. | — | F | H | H | Cl |
| 4. | — | H | H | Me | Cl |
| 5. | — | H | H | Ac | Cl |
| 6. | — | H | Me | Me | Cl |
| 7. | — | F | H | Ac | Cl |
| 8. | 6-fluoro | H | H | H | F |
| 9. | 6-fluoro | H | H | H | Cl |
| 10. | 6-fluoro | F | H | H | Cl |
| 11. | 6-fluoro | H | H | Me | Cl |
| 12. | 6-fluoro | H | H | Ac | Cl |
| 13. | 6-fluoro | H | Me | Me | Cl |
| 14. | 6-fluoro | F | H | Ac | Cl |
| 15. | 6-chloro | H | H | H | F |
| 16. | 6-chloro | H | H | H | Cl |
| 17. | 6-chloro | F | H | H | Cl |
| 18. | 6-chloro | H | H | Me | Cl |
| 19. | 6-chloro | H | H | Ac | Cl |
| 20. | 6-chloro | H | Me | Me | Cl |
| 21. | 6-chloro | F | H | Ac | Cl |
| 22. | 6-methoxy | H | H | H | F |
| 23. | 6-methoxy | H | H | H | Cl |
| 24. | 6-methoxy | F | H | H | Cl |
| 25. | 6-methoxy | H | H | Me | Cl |
| 26. | 6-methoxy | H | H | Ac | Cl |
| 27. | 6-methoxy | H | Me | Me | Cl |
| 28. | 6-methoxy | F | H | Ac | Cl |
| 29. | 5-fluoro | H | H | H | F |
| 30. | 5-fluoro | H | H | H | Cl |
| 31. | 5-fluoro | F | H | H | Cl |
| 32. | 5-fluoro | H | H | Me | Cl |
| 33. | 5-fluoro | H | H | Ac | Cl |
| 34. | 5-fluoro | H | Me | Me | Cl |
| 35. | 5-fluoro | F | H | Ac | Cl |
| 36. | 5-chloro | H | H | H | F |
| 37. | 5-chloro | H | H | H | Cl |
| 38. | 5-chloro | F | H | H | Cl |
| 39. | 5-chloro | H | H | Me | Cl |
| 40. | 5-chloro | H | H | Ac | Cl |
| 41. | 5-chloro | H | Me | Me | Cl |
| 42. | 5-chloro | F | H | Ac | Cl |
| 43. | 5-methoxy | H | H | H | F |
| 44. | 5-methoxy | H | H | H | Cl |
| 45. | 5-methoxy | F | H | H | Cl |
| 46. | 5-methoxy | H | H | Me | Cl |
| 47. | 5-methoxy | H | H | Ac | Cl |
| 48. | 5-methoxy | H | Me | Me | Cl |
| 49. | 5-methoxy | F | H | Ac | Cl |
| 50. | 4-fluoro | H | H | H | F |
| 51. | 4-fluoro | H | H | H | Cl |
| 52. | 4-fluoro | F | H | H | Cl |
| 53. | 4-fluoro | H | H | Me | Cl |
| 54. | 4-fluoro | H | H | Ac | Cl |
| 55. | 4-fluoro | H | Me | Me | Cl |
| 56. | 4-fluoro | F | H | Ac | Cl |
| 57. | 4-chloro | H | H | H | F |
| 58. | 4-chloro | H | H | H | Cl |

TABLE 1-continued compounds of the formula (I) where R' = methyl $$\text{(I)}$$

in which, by definition, the amino group in the phenyl radical is always fixed at the 2 position irrespective of the priority of further R¹ substituents.

| Ex. no. | R¹ | R² | R³ | R⁴ | R⁵ |
|---|---|---|---|---|---|
| 59. | 4-chloro | H | H | H | Me |
| 60. | 4-chloro | H | H | H | Vin |
| 61. | 4-chloro | H | H | H | OMe |
| 62. | 4-chloro | F | H | H | Cl |
| 63. | 4-chloro | H | H | Me | Cl |
| 64. | 4-chloro | H | H | Ac | Cl |
| 65. | 4-chloro | H | Me | Me | Cl |
| 66. | 4-chloro | F | H | Ac | Cl |
| 67. | 4-chloro | CN | H | H | Cl |
| 68. | 4-bromo | H | H | H | F |
| 69. | 4-bromo | H | H | H | Cl |
| 70. | 4-bromo | F | H | H | Cl |
| 71. | 4-bromo | H | H | Me | Cl |
| 72. | 4-bromo | H | H | Ac | Cl |
| 73. | 4-bromo | H | Me | Me | Cl |
| 74. | 4-bromo | F | H | Ac | Cl |
| 75. | 4-iodo | H | H | H | F |
| 76. | 4-iodo | H | H | H | Cl |
| 77. | 4-iodo | F | H | H | Cl |
| 78. | 4-iodo | H | H | Me | Cl |
| 79. | 4-iodo | H | H | Ac | Cl |
| 80. | 4-iodo | H | Me | Me | Cl |
| 81. | 4-iodo | F | H | Ac | Cl |
| 82. | 4-methoxy | H | H | H | F |
| 83. | 4-methoxy | H | H | H | Cl |
| 84. | 4-methoxy | F | H | H | Cl |
| 85. | 4-methoxy | H | H | Me | Cl |
| 86. | 4-methoxy | H | H | Ac | Cl |
| 87. | 4-methoxy | H | Me | Me | Cl |
| 88. | 4-methoxy | F | H | Ac | Cl |
| 89. | 4-methoxycarbonyl | H | H | H | F |
| 90. | 4-methoxycarbonyl | H | H | H | Cl |
| 91. | 4-methoxycarbonyl | F | H | H | Cl |
| 92. | 4-methoxycarbonyl | H | H | Me | Cl |
| 93. | 4-methoxycarbonyl | H | H | Ac | Cl |
| 94. | 4-methoxycarbonyl | H | Me | Me | Cl |
| 95. | 4-methoxycarbonyl | F | H | Ac | Cl |
| 96. | 3-fluoro | H | H | H | F |
| 97. | 3-fluoro | H | H | H | Cl |
| 98. | 3-fluoro | F | H | H | Cl |
| 99. | 3-fluoro | H | H | Me | Cl |
| 100. | 3-fluoro | H | H | Ac | Cl |
| 101. | 3-fluoro | H | Me | Me | Cl |
| 102. | 3-fluoro | F | H | Ac | Cl |
| 103. | 3-chloro | H | H | H | F |
| 104. | 3-chloro | H | H | H | Cl |
| 105. | 3-chloro | F | H | H | Cl |
| 106. | 3-chloro | H | H | Me | Cl |
| 107. | 3-chloro | H | H | Ac | Cl |
| 108. | 3-chloro | H | Me | Me | Cl |
| 109. | 3-chloro | F | H | Ac | Cl |
| 110. | 3-methyl | H | H | H | F |
| 111. | 3-methyl | H | H | H | Cl |
| 112. | 3-methyl | F | H | H | Cl |
| 113. | 3-methyl | H | H | Me | Cl |
| 114. | 3-methyl | H | H | Ac | Cl |
| 115. | 3-methyl | H | Me | Me | Cl |
| 116. | 3-methyl | F | H | Ac | Cl |
| 117. | 3-methoxy | H | H | H | F |
| 118. | 3-methoxy | H | H | H | Cl |
| 119. | 3-methoxy | F | H | H | Cl |
| 120. | 3-methoxy | H | H | Me | Cl |
| 121. | 3-methoxy | H | H | Ac | Cl |
| 122. | 3-methoxy | H | Me | Me | Cl |
| 123. | 3-methoxy | F | H | Ac | Cl |
| 124. | 3-methylthio | H | H | H | F |
| 125. | 3-methylthio | H | H | H | Cl |
| 126. | 3-methylthio | F | H | H | Cl |
| 127. | 3-methylthio | H | H | Me | Cl |
| 128. | 3-methylthio | H | H | Ac | Cl |
| 129. | 3-methylthio | H | Me | Me | Cl |
| 130. | 3-methylthio | F | H | Ac | Cl |
| 131. | 6-fluoro-4-chloro | H | H | H | F |
| 132. | 6-fluoro-4-chloro | H | H | H | Cl |
| 133. | 6-fluoro-4-chloro | F | H | H | Cl |
| 134. | 6-fluoro-4-chloro | H | H | Me | Cl |
| 135. | 6-fluoro-4-chloro | H | H | Ac | Cl |
| 136. | 6-fluoro-4-chloro | H | Me | Me | Cl |
| 137. | 6-fluoro-4-chloro | F | H | Ac | Cl |
| 138. | 6-fluoro-4-fluoro | H | H | H | F |
| 139. | 6-fluoro-4-fluoro | H | H | H | Cl |
| 140. | 6-fluoro-4-fluoro | F | H | H | Cl |
| 141. | 6-fluoro-4-fluoro | H | H | Me | Cl |
| 142. | 6-fluoro-4-fluoro | H | H | Ac | Cl |
| 143. | 6-fluoro-4-fluoro | H | Me | Me | Cl |
| 144. | 6-fluoro-4-fluoro | F | H | Ac | Cl |
| 145. | 6-fluoro-3-methoxy | H | H | H | F |
| 146. | 6-fluoro-3-methoxy | H | H | H | Cl |
| 147. | 6-fluoro-3-methoxy | F | H | H | Cl |
| 148. | 6-fluoro-3-methoxy | H | H | Me | Cl |
| 149. | 6-fluoro-3-methoxy | H | H | Ac | Cl |
| 150. | 6-fluoro-3-methoxy | H | Me | Me | Cl |
| 151. | 6-fluoro-3-methoxy | F | H | Ac | Cl |
| 152. | 5-fluoro-4-chloro | H | H | H | F |
| 153. | 5-fluoro-4-chloro | H | H | H | Cl |
| 154. | 5-fluoro-4-chloro | F | H | H | Cl |
| 155. | 5-fluoro-4-chloro | H | H | Me | Cl |
| 156. | 5-fluoro-4-chloro | H | H | Ac | Cl |
| 157. | 5-fluoro-4-chloro | H | Me | Me | Cl |
| 158. | 5-fluoro-4-chloro | F | H | Ac | Cl |
| 159. | 5-fluoro-4-fluoro | H | H | H | F |
| 160. | 5-fluoro-4-fluoro | H | H | H | Cl |
| 161. | 5-fluoro-4-fluoro | F | H | H | Cl |
| 162. | 5-fluoro-4-fluoro | H | H | Me | Cl |
| 163. | 5-fluoro-4-fluoro | H | H | Ac | Cl |
| 164. | 5-fluoro-4-fluoro | H | Me | Me | Cl |
| 165. | 5-fluoro-4-fluoro | F | H | Ac | Cl |
| 166. | 5-fluoro-3-fluoro | H | H | H | F |
| 167. | 5-fluoro-3-fluoro | H | H | H | Cl |
| 168. | 5-fluoro-3-fluoro | F | H | H | Cl |
| 169. | 5-fluoro-3-fluoro | H | H | Me | Cl |
| 170. | 5-fluoro-3-fluoro | H | H | Ac | Cl |
| 171. | 5-fluoro-3-fluoro | H | Me | Me | Cl |
| 172. | 5-fluoro-3-fluoro | F | H | Ac | Cl |
| 173. | 5-chloro-4-chloro | H | H | H | F |
| 174. | 5-chloro-4-chloro | H | H | H | Cl |

TABLE 1-continued compounds of the formula (I) where R' = methyl $$\text{(I)}$$

in which, by definition, the amino group in the phenyl radical is always fixed at the 2 position irrespective of the priority of further R¹ substituents.

| Ex. no. | R¹ | R² | R³ | R⁴ | R⁵ |
|---|---|---|---|---|---|
| 175. | 5-chloro-4-chloro | F | H | H | Cl |
| 176. | 5-chloro-4-chloro | H | H | Me | Cl |
| 177. | 5-chloro-4-chloro | H | H | Ac | Cl |
| 178. | 5-chloro-4-chloro | H | Me | Me | Cl |
| 179. | 5-chloro-4-chloro | F | H | Ac | Cl |
| 180. | 4-chloro-3-fluoro | H | H | H | F |
| 181. | 4-chloro-3-fluoro | H | H | H | Cl |
| 182. | 4-chloro-3-fluoro | F | H | H | Cl |
| 183. | 4-chloro-3-fluoro | H | H | Me | Cl |
| 184. | 4-chloro-3-fluoro | H | H | Ac | Cl |
| 185. | 4-chloro-3-fluoro | H | Me | Me | Cl |
| 186. | 4-chloro-3-fluoro | F | H | Ac | Cl |
| 187. | 4-chloro-3-methyl | H | H | H | F |
| 188. | 4-chloro-3-methyl | H | H | H | Cl |
| 189. | 4-chloro-3-methyl | F | H | H | Cl |
| 190. | 4-chloro-3-methyl | H | H | Me | Cl |
| 191. | 4-chloro-3-methyl | H | H | Ac | Cl |
| 192. | 4-chloro-3-methyl | H | Me | Me | Cl |
| 193. | 4-chloro-3-methyl | F | H | Ac | Cl |
| 194. | 4-chloro-3-cyclopropyl | H | H | H | F |
| 195. | 4-chloro-3-cyclopropyl | H | H | H | Cl |
| 196. | 4-chloro-3-cyclopropyl | F | H | H | Cl |
| 197. | 4-chloro-3-cyclopropyl | H | H | Me | Cl |
| 198. | 4-chloro-3-cyclopropyl | H | H | Ac | Cl |
| 199. | 4-chloro-3-cyclopropyl | H | Me | Me | Cl |
| 200. | 4-chloro-3-cyclopropyl | F | H | Ac | Cl |
| 201. | 4-chloro-3-methoxy | H | H | H | F |
| 202. | 4-chloro-3-methoxy | H | H | H | Cl |
| 203. | 4-chloro-3-methoxy | F | H | H | Cl |
| 204. | 4-chloro-3-methoxy | H | H | Me | Cl |
| 205. | 4-chloro-3-methoxy | H | H | Ac | Cl |
| 206. | 4-chloro-3-methoxy | H | Me | Me | Cl |
| 207. | 4-chloro-3-methoxy | F | H | Ac | Cl |
| 208. | 4-chloro-3-methylthio | H | H | H | F |
| 209. | 4-chloro-3-methylthio | H | H | H | Cl |
| 210. | 4-chloro-3-methylthio | F | H | H | Cl |
| 211. | 4-chloro-3-methylthio | H | H | Me | Cl |
| 212. | 4-chloro-3-methylthio | H | H | Ac | Cl |
| 213. | 4-chloro-3-methylthio | H | Me | Me | Cl |
| 214. | 4-chloro-3-methylthio | F | H | Ac | Cl |
| 215. | 4-chloro-3-dimethylamino | H | H | H | F |
| 216. | 4-chloro-3-dimethylamino | H | H | H | Cl |
| 217. | 4-chloro-3-dimethylamino | F | H | H | Cl |
| 218. | 4-chloro-3-dimethylamino | H | H | Me | Cl |
| 219. | 4-chloro-3-dimethylamino | H | H | Ac | Cl |
| 220. | 4-chloro-3-dimethylamino | H | Me | Me | Cl |
| 221. | 4-chloro-3-dimethylamino | F | H | Ac | Cl |
| 222. | 4-chloro-3-methoxymethyl | H | H | H | F |
| 223. | 4-chloro-3-methoxymethyl | H | H | H | Cl |
| 224. | 4-chloro-3-methoxymethyl | H | H | H | Me |
| 225. | 4-chloro-3-methoxymethyl | H | H | H | Vin |
| 226. | 4-chloro-3-methoxymethyl | H | H | H | OMe |
| 227. | 4-chloro-3-methoxymethyl | F | H | H | Cl |
| 228. | 4-chloro-3-methoxymethyl | H | H | Me | Cl |
| 229. | 4-chloro-3-methoxymethyl | H | H | Ac | Cl |
| 230. | 4-chloro-3-methoxymethyl | H | Me | Me | Cl |
| 231. | 4-chloro-3-methoxymethyl | F | H | Ac | Cl |
| 232. | 4-chloro-3-methoxymethyl | CN | H | H | Cl |
| 233. | 4-methyl-3-fluoro | H | H | H | F |
| 234. | 4-methyl-3-fluoro | H | H | H | Cl |
| 235. | 4-methyl-3-fluoro | F | H | H | Cl |
| 236. | 4-methyl-3-fluoro | H | H | Me | Cl |
| 237. | 4-methyl-3-fluoro | H | H | Ac | Cl |
| 238. | 4-methyl-3-fluoro | H | Me | Me | Cl |
| 239. | 4-methyl-3-fluoro | F | H | Ac | Cl |
| 240. | 4-methyl-3-methoxy | H | H | H | F |
| 241. | 4-methyl-3-methoxy | H | H | H | Cl |
| 242. | 4-methyl-3-methoxy | F | H | H | Cl |
| 243. | 4-methyl-3-methoxy | H | H | Me | Cl |
| 244. | 4-methyl-3-methoxy | H | H | Ac | Cl |
| 245. | 4-methyl-3-methoxy | H | Me | Me | Cl |
| 246. | 4-methyl-3-methoxy | F | H | Ac | Cl |
| 247. | 6-fluoro-5-trifluoromethyl-4-fluoro | H | H | H | F |
| 248. | 6-fluoro-5-trifluoromethyl-4-fluoro | H | H | H | Cl |
| 249. | 6-fluoro-5-trifluoromethyl-4-fluoro | F | H | H | Cl |
| 250. | 6-fluoro-5-trifluoromethyl-4-fluoro | H | H | Me | Cl |
| 251. | 6-fluoro-5-trifluoromethyl-4-fluoro | H | H | Ac | Cl |
| 252. | 6-fluoro-5-trifluoromethyl-4-fluoro | H | Me | Me | Cl |
| 253. | 6-fluoro-5-trifluoromethyl-4-fluoro | F | H | Ac | Cl |
| 254. | 6-fluoro-4-chloro-3-methoxy | H | H | H | F |
| 255. | 6-fluoro-4-chloro-3-methoxy | H | H | H | Cl |
| 256. | 6-fluoro-4-chloro-3-methoxy | H | H | H | Me |
| 257. | 6-fluoro-4-chloro-3-methoxy | H | H | H | Vin |
| 258. | 6-fluoro-4-chloro-3-methoxy | H | H | H | OMe |
| 259. | 6-fluoro-4-chloro-3-methoxy | F | H | H | Cl |
| 260. | 6-fluoro-4-chloro-3-methoxy | H | H | Me | Cl |
| 261. | 6-fluoro-4-chloro-3-methoxy | H | H | Ac | Cl |
| 262. | 6-fluoro-4-chloro-3-methoxy | H | Me | Me | Cl |
| 263. | 6-fluoro-4-chloro-3-methoxy | F | H | Ac | Cl |
| 264. | 6-fluoro-4-chloro-3-methoxy | CN | H | H | Cl |
| 265. | 6-fluoro-4-chloro-3-methylthio | H | H | H | F |
| 266. | 6-fluoro-4-chloro-3-methylthio | H | H | H | Cl |
| 267. | 6-fluoro-4-chloro-3-methylthio | F | H | H | Cl |
| 268. | 6-fluoro-4-chloro-3-methylthio | H | H | Me | Cl |
| 269. | 6-fluoro-4-chloro-3-methylthio | H | H | Ac | Cl |
| 270. | 6-fluoro-4-chloro-3-methylthio | H | Me | Me | Cl |
| 271. | 6-fluoro-4-chloro-3-methylthio | F | H | Ac | Cl |
| 272. | 6-fluoro-4-chloro-3-methyl | H | H | H | F |
| 273. | 6-fluoro-4-chloro-3-methyl | H | H | H | Cl |
| 274. | 6-fluoro-4-chloro-3-methyl | F | H | H | Cl |
| 275. | 6-fluoro-4-chloro-3-methyl | H | H | Me | Cl |
| 276. | 6-fluoro-4-chloro-3-methyl | H | H | Ac | Cl |

TABLE 1-continued compounds of the formula (I) where R' = methyl in which, by definition, the amino group in the phenyl radical is always fixed at the 2 position irrespective of the priority of further R¹ substituents.

| Ex. no. | R¹ | R² | R³ | R⁴ | R⁵ |
|---|---|---|---|---|---|
| 277. | 6-fluoro-4-chloro-3-methyl | H | Me | Me | Cl |
| 278. | 6-fluoro-4-chloro-3-methyl | F | H | Ac | Cl |
| 279. | 5-fluoro-4-chloro-3-fluoro | H | H | H | F |
| 280. | 5-fluoro-4-chloro-3-fluoro | H | H | H | Cl |
| 281. | 5-fluoro-4-chloro-3-fluoro | F | H | H | Cl |
| 282. | 5-fluoro-4-chloro-3-fluoro | H | H | Me | Cl |
| 283. | 5-fluoro-4-chloro-3-fluoro | H | H | Ac | Cl |
| 284. | 5-fluoro-4-chloro-3-fluoro | H | Me | Me | Cl |
| 285. | 5-fluoro-4-chloro-3-fluoro | F | H | Ac | Cl |
| 286. | 5-fluoro-4-chloro-3-methyl | H | H | H | F |
| 287. | 5-fluoro-4-chloro-3-methyl | H | H | H | Cl |
| 288. | 5-fluoro-4-chloro-3-methyl | F | H | H | Cl |
| 289. | 5-fluoro-4-chloro-3-methyl | H | H | Me | Cl |
| 290. | 5-fluoro-4-chloro-3-methyl | H | H | Ac | Cl |
| 291. | 5-fluoro-4-chloro-3-methyl | H | Me | Me | Cl |
| 292. | 5-fluoro-4-chloro-3-methyl | F | H | Ac | Cl |
| 293. | 5-fluoro-4-chloro-3-methoxy | H | H | H | F |
| 294. | 5-fluoro-4-chloro-3-methoxy | H | H | H | Cl |
| 295. | 5-fluoro-4-chloro-3-methoxy | F | H | H | Cl |
| 296. | 5-fluoro-4-chloro-3-methoxy | H | H | Me | Cl |
| 297. | 5-fluoro-4-chloro-3-methoxy | H | H | Ac | Cl |
| 298. | 5-fluoro-4-chloro-3-methoxy | H | Me | Me | Cl |
| 299. | 5-fluoro-4-chloro-3-methoxy | F | H | Ac | Cl |
| 300. | 6-fluoro-5-fluoro-4-fluoro-3-methoxy | H | H | H | F |
| 301. | 6-fluoro-5-fluoro-4-fluoro-3-methoxy | H | H | H | Cl |
| 302. | 6-fluoro-5-fluoro-4-fluoro-3-methoxy | F | H | H | Cl |
| 303. | 6-fluoro-5-fluoro-4-fluoro-3-methoxy | H | H | Me | Cl |
| 304. | 6-fluoro-5-fluoro-4-fluoro-3-methoxy | H | H | Ac | Cl |
| 305. | 6-fluoro-5-fluoro-4-fluoro-3-methoxy | H | Me | Me | Cl |
| 306. | 6-fluoro-5-fluoro-4-fluoro-3-methoxy | F | H | Ac | Cl |
| 307. | 6-fluoro-5-fluoro-4-fluoro-3-chloro | H | H | H | F |
| 308. | 6-fluoro-5-fluoro-4-fluoro-3-chloro | H | H | H | Cl |
| 309. | 6-fluoro-5-fluoro-4-fluoro-3-chloro | F | H | H | Cl |
| 310. | 6-fluoro-5-fluoro-4-fluoro-3-chloro | H | H | Me | Cl |
| 311. | 6-fluoro-5-fluoro-4-fluoro-3-chloro | H | H | Ac | Cl |
| 312. | 6-fluoro-5-fluoro-4-fluoro-3-chloro | H | Me | Me | Cl |
| 313. | 6-fluoro-5-fluoro-4-fluoro-3-chloro | F | H | Ac | Cl |

TABLE 2 compounds of the formula (I) where R' = hydrogen in which, by definition, the amino group in the phenyl radical is always fixed at the 2 position irrespective of the priority of further R¹ substituents.

| Ex. no. | R¹ | R² | R³ | R⁴ | R⁵ |
|---|---|---|---|---|---|
| 314. | — | H | H | H | F |
| 315. | — | H | H | H | Cl |
| 316. | — | F | H | H | Cl |
| 317. | — | H | H | Me | Cl |
| 318. | — | H | H | Ac | Cl |
| 319. | — | H | Me | Me | Cl |
| 320. | — | F | H | Ac | Cl |
| 321. | 6-fluoro | H | H | H | F |
| 322. | 6-fluoro | H | H | H | Cl |
| 323. | 6-fluoro | F | H | H | Cl |
| 324. | 6-fluoro | H | H | Me | Cl |
| 325. | 6-fluoro | H | H | Ac | Cl |
| 326. | 6-fluoro | H | Me | Me | Cl |
| 327. | 6-fluoro | F | H | Ac | Cl |
| 328. | 6-chloro | H | H | H | F |
| 329. | 6-chloro | H | H | H | Cl |
| 330. | 6-chloro | F | H | H | Cl |
| 331. | 6-chloro | H | H | Me | Cl |
| 332. | 6-chloro | H | H | Ac | Cl |
| 333. | 6-chloro | H | Me | Me | Cl |
| 334. | 6-chloro | F | H | Ac | Cl |
| 335. | 6-methoxy | H | H | H | F |
| 336. | 6-methoxy | H | H | H | Cl |
| 337. | 6-methoxy | F | H | H | Cl |
| 338. | 6-methoxy | H | H | Me | Cl |
| 339. | 6-methoxy | H | H | Ac | Cl |
| 340. | 6-methoxy | H | Me | Me | Cl |
| 341. | 6-methoxy | F | H | Ac | Cl |
| 342. | 5-fluoro | H | H | H | F |
| 343. | 5-fluoro | H | H | H | Cl |
| 344. | 5-fluoro | F | H | H | Cl |
| 345. | 5-fluoro | H | H | Me | Cl |
| 346. | 5-fluoro | H | H | Ac | Cl |
| 347. | 5-fluoro | H | Me | Me | Cl |
| 348. | 5-fluoro | F | H | Ac | Cl |
| 349. | 5-chloro | H | H | H | F |
| 350. | 5-chloro | H | H | H | Cl |
| 351. | 5-chloro | F | H | H | Cl |
| 352. | 5-chloro | H | H | Me | Cl |
| 353. | 5-chloro | H | H | Ac | Cl |
| 354. | 5-chloro | H | Me | Me | Cl |
| 355. | 5-chloro | F | H | Ac | Cl |
| 356. | 5-methoxy | H | H | H | F |
| 357. | 5-methoxy | H | H | H | Cl |
| 358. | 5-methoxy | F | H | H | Cl |
| 359. | 5-methoxy | H | H | Me | Cl |
| 360. | 5-methoxy | H | H | Ac | Cl |
| 361. | 5-methoxy | H | Me | Me | Cl |
| 362. | 5-methoxy | F | H | Ac | Cl |
| 363. | 4-fluoro | H | H | H | F |
| 364. | 4-fluoro | H | H | H | Cl |
| 365. | 4-fluoro | F | H | H | Cl |
| 366. | 4-fluoro | H | H | Me | Cl |
| 367. | 4-fluoro | H | H | Ac | Cl |
| 368. | 4-fluoro | H | Me | Me | Cl |
| 369. | 4-fluoro | F | H | Ac | Cl |
| 370. | 4-chloro | H | H | H | F |
| 371. | 4-chloro | H | H | H | Cl |
| 372. | 4-chloro | H | H | H | Me |

TABLE 2-continued compounds of the formula (I) where R' = hydrogen $$\text{(I)}$$

in which, by definition, the amino group in the phenyl radical is always fixed at the 2 position irrespective of the priority of further $R^1$ substituents.

| Ex. no. | $R^1$ | $R^2$ | $R^3$ | $R^4$ | $R^5$ |
|---|---|---|---|---|---|
| 373. | 4-chloro | H | H | H | Vin |
| 374. | 4-chloro | H | H | H | OMe |
| 375. | 4-chloro | F | H | H | Cl |
| 376. | 4-chloro | H | H | Me | Cl |
| 377. | 4-chloro | H | H | Ac | Cl |
| 378. | 4-chloro | H | Me | Me | Cl |
| 379. | 4-chloro | F | H | Ac | Cl |
| 380. | 4-chloro | CN | H | H | Cl |
| 381. | 4-bromo | H | H | H | F |
| 382. | 4-bromo | H | H | H | Cl |
| 383. | 4-bromo | F | H | H | Cl |
| 384. | 4-bromo | H | H | Me | Cl |
| 385. | 4-bromo | H | H | Ac | Cl |
| 386. | 4-bromo | H | Me | Me | Cl |
| 387. | 4-bromo | F | H | Ac | Cl |
| 388. | 4-iodo | H | H | H | F |
| 389. | 4-iodo | H | H | H | Cl |
| 390. | 4-iodo | F | H | H | Cl |
| 391. | 4-iodo | H | H | Me | Cl |
| 392. | 4-iodo | H | H | Ac | Cl |
| 393. | 4-iodo | H | Me | Me | Cl |
| 394. | 4-iodo | F | H | Ac | Cl |
| 395. | 4-methoxy | H | H | H | F |
| 396. | 4-methoxy | H | H | H | Cl |
| 397. | 4-methoxy | F | H | H | Cl |
| 398. | 4-methoxy | H | H | Me | Cl |
| 399. | 4-methoxy | H | H | Ac | Cl |
| 400. | 4-methoxy | H | Me | Me | Cl |
| 401. | 4-methoxy | F | H | Ac | Cl |
| 402. | 4-methoxycarbonyl | H | H | H | F |
| 403. | 4-methoxycarbonyl | H | H | H | Cl |
| 404. | 4-methoxycarbonyl | F | H | H | Cl |
| 405. | 4-methoxycarbonyl | H | H | Me | Cl |
| 406. | 4-methoxycarbonyl | H | H | Ac | Cl |
| 407. | 4-methoxycarbonyl | H | Me | Me | Cl |
| 408. | 4-methoxycarbonyl | F | H | Ac | Cl |
| 409. | 3-fluoro | H | H | H | F |
| 410. | 3-fluoro | H | H | H | Cl |
| 411. | 3-fluoro | F | H | H | Cl |
| 412. | 3-fluoro | H | H | Me | Cl |
| 413. | 3-fluoro | H | H | Ac | Cl |
| 414. | 3-fluoro | H | Me | Me | Cl |
| 415. | 3-fluoro | F | H | Ac | Cl |
| 416. | 3-chloro | H | H | H | F |
| 417. | 3-chloro | H | H | H | Cl |
| 418. | 3-chloro | F | H | H | Cl |
| 419. | 3-chloro | H | H | Me | Cl |
| 420. | 3-chloro | H | H | Ac | Cl |
| 421. | 3-chloro | H | Me | Me | Cl |
| 422. | 3-chloro | F | H | Ac | Cl |
| 423. | 3-methyl | H | H | H | F |
| 424. | 3-methyl | H | H | H | Cl |
| 425. | 3-methyl | F | H | H | Cl |
| 426. | 3-methyl | H | H | Me | Cl |
| 427. | 3-methyl | H | H | Ac | Cl |
| 428. | 3-methyl | H | Me | Me | Cl |
| 429. | 3-methyl | F | H | Ac | Cl |
| 430. | 3-methoxy | H | H | H | F |
| 431. | 3-methoxy | H | H | H | Cl |
| 432. | 3-methoxy | F | H | H | Cl |
| 433. | 3-methoxy | H | H | Me | Cl |
| 434. | 3-methoxy | H | H | Ac | Cl |
| 435. | 3-methoxy | H | Me | Me | Cl |
| 436. | 3-methoxy | F | H | Ac | Cl |
| 437. | 3-methylthio | H | H | H | F |
| 438. | 3-methylthio | H | H | H | Cl |
| 439. | 3-methylthio | F | H | H | Cl |
| 440. | 3-methylthio | H | H | Me | Cl |
| 441. | 3-methylthio | H | H | Ac | Cl |
| 442. | 3-methylthio | H | Me | Me | Cl |
| 443. | 3-methylthio | F | H | Ac | Cl |
| 444. | 6-fluoro-4-chloro | H | H | H | F |
| 445. | 6-fluoro-4-chloro | H | H | H | Cl |
| 446. | 6-fluoro-4-chloro | F | H | H | Cl |
| 447. | 6-fluoro-4-chloro | H | H | Me | Cl |
| 448. | 6-fluoro-4-chloro | H | H | Ac | Cl |
| 449. | 6-fluoro-4-chloro | H | Me | Me | Cl |
| 450. | 6-fluoro-4-chloro | F | H | Ac | Cl |
| 451. | 6-fluoro-4-fluoro | H | H | H | F |
| 452. | 6-fluoro-4-fluoro | H | H | H | Cl |
| 453. | 6-fluoro-4-fluoro | F | H | H | Cl |
| 454. | 6-fluoro-4-fluoro | H | H | Me | Cl |
| 455. | 6-fluoro-4-fluoro | H | H | Ac | Cl |
| 456. | 6-fluoro-4-fluoro | H | Me | Me | Cl |
| 457. | 6-fluoro-4-fluoro | F | H | Ac | Cl |
| 458. | 6-fluoro-3-methoxy | H | H | H | F |
| 459. | 6-fluoro-3-methoxy | H | H | H | Cl |
| 460. | 6-fluoro-3-methoxy | F | H | H | Cl |
| 461. | 6-fluoro-3-methoxy | H | H | Me | Cl |
| 462. | 6-fluoro-3-methoxy | H | H | Ac | Cl |
| 463. | 6-fluoro-3-methoxy | H | Me | Me | Cl |
| 464. | 6-fluoro-3-methoxy | F | H | Ac | Cl |
| 465. | 5-fluoro-4-chloro | H | H | H | F |
| 466. | 5-fluoro-4-chloro | H | H | H | Cl |
| 467. | 5-fluoro-4-chloro | F | H | H | Cl |
| 468. | 5-fluoro-4-chloro | H | H | Me | Cl |
| 469. | 5-fluoro-4-chloro | H | H | Ac | Cl |
| 470. | 5-fluoro-4-chloro | H | Me | Me | Cl |
| 471. | 5-fluoro-4-chloro | F | H | Ac | Cl |
| 472. | 5-fluoro-4-fluoro | H | H | H | F |
| 473. | 5-fluoro-4-fluoro | H | H | H | Cl |
| 474. | 5-fluoro-4-fluoro | F | H | H | Cl |
| 475. | 5-fluoro-4-fluoro | H | H | Me | Cl |
| 476. | 5-fluoro-4-fluoro | H | H | Ac | Cl |
| 477. | 5-fluoro-4-fluoro | H | Me | Me | Cl |
| 478. | 5-fluoro-4-fluoro | F | H | Ac | Cl |
| 479. | 5-fluoro-3-fluoro | H | H | H | F |
| 480. | 5-fluoro-3-fluoro | H | H | H | Cl |
| 481. | 5-fluoro-3-fluoro | F | H | H | Cl |
| 482. | 5-fluoro-3-fluoro | H | H | Me | Cl |
| 483. | 5-fluoro-3-fluoro | H | H | Ac | Cl |
| 484. | 5-fluoro-3-fluoro | H | Me | Me | Cl |
| 485. | 5-fluoro-3-fluoro | F | H | Ac | Cl |
| 486. | 5-chloro-4-chloro | H | H | H | F |
| 487. | 5-chloro-4-chloro | H | H | H | Cl |
| 488. | 5-chloro-4-chloro | F | H | H | Cl |
| 489. | 5-chloro-4-chloro | H | H | Me | Cl |
| 490. | 5-chloro-4-chloro | H | H | Ac | Cl |

TABLE 2-continued compounds of the formula (I) where R' = hydrogen $$\text{(I)}$$

in which, by definition, the amino group in the phenyl radical is always fixed at the 2 position irrespective of the priority of further $R^1$ substituents.

| Ex. no. | $R^1$ | $R^2$ | $R^3$ | $R^4$ | $R^5$ |
|---|---|---|---|---|---|
| 491. | 5-chloro-4-chloro | H | Me | Me | Cl |
| 492. | 5-chloro-4-chloro | F | H | Ac | Cl |
| 493. | 4-chloro-3-fluoro | H | H | H | F |
| 494. | 4-chloro-3-fluoro | H | H | H | Cl |
| 495. | 4-chloro-3-fluoro | F | H | H | Cl |
| 496. | 4-chloro-3-fluoro | H | H | Me | Cl |
| 497. | 4-chloro-3-fluoro | H | H | Ac | Cl |
| 498. | 4-chloro-3-fluoro | H | Me | Me | Cl |
| 499. | 4-chloro-3-fluoro | F | H | Ac | Cl |
| 500. | 4-chloro-3-methyl | H | H | H | F |
| 501. | 4-chloro-3-methyl | H | H | H | Cl |
| 502. | 4-chloro-3-methyl | F | H | H | Cl |
| 503. | 4-chloro-3-methyl | H | H | Me | Cl |
| 504. | 4-chloro-3-methyl | H | H | Ac | Cl |
| 505. | 4-chloro-3-methyl | H | Me | Me | Cl |
| 506. | 4-chloro-3-methyl | F | H | Ac | Cl |
| 507. | 4-chloro-3-cyclopropyl | H | H | H | F |
| 508. | 4-chloro-3-cyclopropyl | H | H | H | Cl |
| 509. | 4-chloro-3-cyclopropyl | F | H | H | Cl |
| 510. | 4-chloro-3-cyclopropyl | H | H | Me | Cl |
| 511. | 4-chloro-3-cyclopropyl | H | H | Ac | Cl |
| 512. | 4-chloro-3-cyclopropyl | H | Me | Me | Cl |
| 513. | 4-chloro-3-cyclopropyl | F | H | Ac | Cl |
| 514. | 4-chloro-3-methoxy | H | H | H | F |
| 515. | 4-chloro-3-methoxy | H | H | H | Cl |
| 516. | 4-chloro-3-methoxy | F | H | H | Cl |
| 517. | 4-chloro-3-methoxy | H | H | Me | Cl |
| 518. | 4-chloro-3-methoxy | H | H | Ac | Cl |
| 519. | 4-chloro-3-methoxy | H | Me | Me | Cl |
| 520. | 4-chloro-3-methoxy | F | H | Ac | Cl |
| 521. | 4-chloro-3-methylthio | H | H | H | F |
| 522. | 4-chloro-3-methylthio | H | H | H | Cl |
| 523. | 4-chloro-3-methylthio | F | H | H | Cl |
| 524. | 4-chloro-3-methylthio | H | H | Me | Cl |
| 525. | 4-chloro-3-methylthio | H | H | Ac | Cl |
| 526. | 4-chloro-3-methylthio | H | Me | Me | Cl |
| 527. | 4-chloro-3-methylthio | F | H | Ac | Cl |
| 528. | 4-chloro-3-dimethylamino | H | H | H | F |
| 529. | 4-chloro-3-dimethylamino | H | H | H | Cl |
| 530. | 4-chloro-3-dimethylamino | F | H | H | Cl |
| 531. | 4-chloro-3-dimethylamino | H | H | Me | Cl |
| 532. | 4-chloro-3-dimethylamino | H | H | Ac | Cl |
| 533. | 4-chloro-3-dimethylamino | H | Me | Me | Cl |
| 534. | 4-chloro-3-dimethylamino | F | H | Ac | Cl |
| 535. | 4-chloro-3-methoxymethyl | H | H | H | F |
| 536. | 4-chloro-3-methoxymethyl | H | H | H | Cl |
| 537. | 4-chloro-3-methoxymethyl | H | H | H | Me |
| 538. | 4-chloro-3-methoxymethyl | H | H | H | Vin |
| 539. | 4-chloro-3-methoxymethyl | H | H | H | OMe |
| 540. | 4-chloro-3-methoxymethyl | F | H | H | Cl |
| 541. | 4-chloro-3-methoxymethyl | H | H | Me | Cl |
| 542. | 4-chloro-3-methoxymethyl | H | H | Ac | Cl |
| 543. | 4-chloro-3-methoxymethyl | H | Me | Me | Cl |
| 544. | 4-chloro-3-methoxymethyl | F | H | Ac | Cl |
| 545. | 4-chloro-3-methoxymethyl | CN | H | H | Cl |
| 546. | 4-methyl-3-fluoro | H | H | H | F |
| 547. | 4-methyl-3-fluoro | H | H | H | Cl |
| 548. | 4-methyl-3-fluoro | F | H | H | Cl |
| 549. | 4-methyl-3-fluoro | H | H | Me | Cl |
| 550. | 4-methyl-3-fluoro | H | H | Ac | Cl |
| 551. | 4-methyl-3-fluoro | H | Me | Me | Cl |
| 552. | 4-methyl-3-fluoro | F | H | Ac | Cl |
| 553. | 4-methyl-3-methoxy | H | H | H | F |
| 554. | 4-methyl-3-methoxy | H | H | H | Cl |
| 555. | 4-methyl-3-methoxy | F | H | H | Cl |
| 556. | 4-methyl-3-methoxy | H | H | Me | Cl |
| 557. | 4-methyl-3-methoxy | H | H | Ac | Cl |
| 558. | 4-methyl-3-methoxy | H | Me | Me | Cl |
| 559. | 4-methyl-3-methoxy | F | H | Ac | Cl |
| 560. | 6-fluoro-5-trifluoromethyl-4-fluoro | H | H | H | F |
| 561. | 6-fluoro-5-trifluoromethyl-4-fluoro | H | H | H | Cl |
| 562. | 6-fluoro-5-trifluoromethyl-4-fluoro | F | H | H | Cl |
| 563. | 6-fluoro-5-trifluoromethyl-4-fluoro | H | H | Me | Cl |
| 564. | 6-fluoro-5-trifluoromethyl-4-fluoro | H | H | Ac | Cl |
| 565. | 6-fluoro-5-trifluoromethyl-4-fluoro | H | Me | Me | Cl |
| 566. | 6-fluoro-5-trifluoromethyl-4-fluoro | F | H | Ac | Cl |
| 567. | 6-fluoro-4-chloro-3-methoxy | H | H | H | F |
| 568. | 6-fluoro-4-chloro-3-methoxy | H | H | H | Cl |
| 569. | 6-fluoro-4-chloro-3-methoxy | H | H | H | Me |
| 570. | 6-fluoro-4-chloro-3-methoxy | H | H | H | Vin |
| 571. | 6-fluoro-4-chloro-3-methoxy | H | H | H | OMe |
| 572. | 6-fluoro-4-chloro-3-methoxy | F | H | H | Cl |
| 573. | 6-fluoro-4-chloro-3-methoxy | H | H | Me | Cl |
| 574. | 6-fluoro-4-chloro-3-methoxy | H | H | Ac | Cl |
| 575. | 6-fluoro-4-chloro-3-methoxy | H | Me | Me | Cl |
| 576. | 6-fluoro-4-chloro-3-methoxy | F | H | Ac | Cl |
| 577. | 6-fluoro-4-chloro-3-methoxy | CN | H | H | Cl |
| 578. | 6-fluoro-4-chloro-3-methylthio | H | H | H | F |
| 579. | 6-fluoro-4-chloro-3-methylthio | H | H | H | Cl |
| 580. | 6-fluoro-4-chloro-3-methylthio | F | H | H | Cl |
| 581. | 6-fluoro-4-chloro-3-methylthio | H | H | Me | Cl |
| 582. | 6-fluoro-4-chloro-3-methylthio | H | H | Ac | Cl |
| 583. | 6-fluoro-4-chloro-3-methylthio | H | Me | Me | Cl |
| 584. | 6-fluoro-4-chloro-3-methylthio | F | H | Ac | Cl |
| 585. | 6-fluoro-4-chloro-3-methyl | H | H | H | F |
| 586. | 6-fluoro-4-chloro-3-methyl | H | H | H | Cl |
| 587. | 6-fluoro-4-chloro-3-methyl | F | H | H | Cl |
| 588. | 6-fluoro-4-chloro-3-methyl | H | H | Me | Cl |
| 589. | 6-fluoro-4-chloro-3-methyl | H | H | Ac | Cl |
| 590. | 6-fluoro-4-chloro-3-methyl | H | Me | Me | Cl |
| 591. | 6-fluoro-4-chloro-3-methyl | F | H | Ac | Cl |
| 592. | 5-fluoro-4-chloro-3-fluoro | H | H | H | F |
| 593. | 5-fluoro-4-chloro-3-fluoro | H | H | H | Cl |
| 594. | 5-fluoro-4-chloro-3-fluoro | F | H | H | Cl |

TABLE 2-continued compounds of the formula (I) where R' = hydrogen

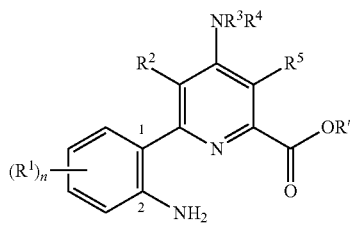

in which, by definition, the amino group in the phenyl radical is always fixed at the 2 position irrespective of the priority of further $R^1$ substituents.

| Ex. no. | $R^1$ | $R^2$ | $R^3$ | $R^4$ | $R^5$ |
|---|---|---|---|---|---|
| 595. | 5-fluoro-4-chloro-3-fluoro | H | H | Me | Cl |
| 596. | 5-fluoro-4-chloro-3-fluoro | H | H | Ac | Cl |
| 597. | 5-fluoro-4-chloro-3-fluoro | H | Me | Me | Cl |
| 598. | 5-fluoro-4-chloro-3-fluoro | F | H | Ac | Cl |
| 599. | 5-fluoro-4-chloro-3-methyl | H | H | H | F |
| 600. | 5-fluoro-4-chloro-3-methyl | H | H | H | Cl |
| 601. | 5-fluoro-4-chloro-3-methyl | F | H | H | Cl |
| 602. | 5-fluoro-4-chloro-3-methyl | H | H | Me | Cl |
| 603. | 5-fluoro-4-chloro-3-methyl | H | H | Ac | Cl |
| 604. | 5-fluoro-4-chloro-3-methyl | H | Me | Me | Cl |
| 605. | 5-fluoro-4-chloro-3-methyl | F | H | Ac | Cl |
| 606. | 5-fluoro-4-chloro-3-methoxy | H | H | H | F |
| 607. | 5-fluoro-4-chloro-3-methoxy | H | H | H | Cl |
| 608. | 5-fluoro-4-chloro-3-methoxy | F | H | H | Cl |
| 609. | 5-fluoro-4-chloro-3-methoxy | H | H | Me | Cl |
| 610. | 5-fluoro-4-chloro-3-methoxy | H | H | Ac | Cl |
| 611. | 5-fluoro-4-chloro-3-methoxy | H | Me | Me | Cl |
| 612. | 5-fluoro-4-chloro-3-methoxy | F | H | Ac | Cl |
| 613. | 6-fluoro-5-fluoro-4-fluoro-3-methoxy | H | H | H | F |
| 614. | 6-fluoro-5-fluoro-4-fluoro-3-methoxy | H | H | H | Cl |
| 615. | 6-fluoro-5-fluoro-4-fluoro-3-methoxy | F | H | H | Cl |
| 616. | 6-fluoro-5-fluoro-4-fluoro-3-methoxy | H | H | Me | Cl |
| 617. | 6-fluoro-5-fluoro-4-fluoro-3-methoxy | H | H | Ac | Cl |
| 618. | 6-fluoro-5-fluoro-4-fluoro-3-methoxy | H | Me | Me | Cl |
| 619. | 6-fluoro-5-fluoro-4-fluoro-3-methoxy | F | H | Ac | Cl |
| 620. | 6-fluoro-5-fluoro-4-fluoro-3-chloro | H | H | H | F |
| 621. | 6-fluoro-5-fluoro-4-fluoro-3-chloro | H | H | H | Cl |
| 622. | 6-fluoro-5-fluoro-4-fluoro-3-chloro | F | H | H | Cl |
| 623. | 6-fluoro-5-fluoro-4-fluoro-3-chloro | H | H | Me | Cl |
| 624. | 6-fluoro-5-fluoro-4-fluoro-3-chloro | H | H | Ac | Cl |
| 625. | 6-fluoro-5-fluoro-4-fluoro-3-chloro | H | Me | Me | Cl |
| 626. | 6-fluoro-5-fluoro-4-fluoro-3-chloro | F | H | Ac | Cl |

TABLE 3

Further compounds of the formula (I) where R' = methyl

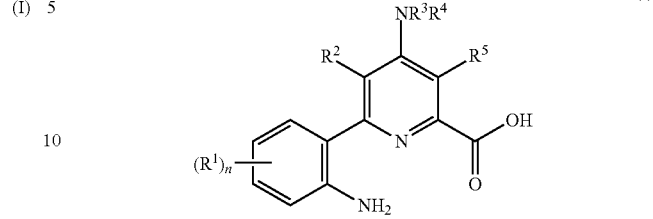

in which the amino group in the phenyl radical, irrespective of the priority of further $R^1$ substituents, is by definition always fixed at the 2 position.

| Ex. No. | $R^1$ | $R^2$ | $R^3$ | $R^4$ | $R^5$ |
|---|---|---|---|---|---|
| 627. | 6-fluoro-3-chloro | H | H | H | Cl |
| 628. | 6-fluoro-5-fluoro-4-fluoro | H | H | H | Cl |
| 629. | 5-methyl | H | H | H | Cl |
| 630. | 5-methoxy-4-chloro | H | H | H | Cl |
| 631. | 5-chloro-4-chloro-3-chloro | F | H | H | Cl |
| 632. | 5-methyl-3-fluoro | H | H | H | Cl |
| 633. | 5-chloro-3-fluoro | H | H | H | Cl |
| 634. | 4-nitro | H | H | H | Cl |
| 635. | 5-chloro-3-methyl | H | H | H | Cl |
| 636. | 5-methyl-4-chloro | H | H | H | Cl |
| 637. | 5-cyano | H | H | H | Cl |
| 638. | 5-fluoro-3-chloro | H | H | H | Cl |
| 639. | 5-chloro-3-fluoro | Cl | H | H | Cl |
| 640. | 5-chloro-3-fluoro | F | H | H | Cl |
| 641. | 5-chloro-4-chloro-3-chloro | H | H | H | Cl |
| 642. | 5-fluoro-4-amino-3-chloro | H | H | H | Cl |
| 643. | 4-trifluoromethyl | H | H | H | Cl |
| 644. | 5-cyano-3-chloro | H | H | H | Cl |
| 645. | 5-chloro-4-fluoro | H | H | H | Cl |
| 646. | 4-nitro-3-chloro | H | H | H | Cl |
| 647. | 5-chloro-4-nitro-3-chloro | H | H | H | Cl |
| 648. | 5-chloro-4-trifluoromethyl | H | H | H | Cl |
| 649. | 5-chloro-4-trifluoromethyl | Cl | H | H | Cl |
| 650. | 5-chloro-4-methyl-3-chloro | H | H | H | Cl |
| 651. | 5-methoxy-4-fluoro | H | H | H | Cl |
| 652. | 5-fluoro-4-methyl | H | H | H | Cl |
| 653. | 5-fluoro-4-fluoro-3-fluoro | H | H | H | Cl |
| 654. | 6-fluoro-5-fluoro | H | H | H | Cl |
| 655. | 5-nitro-3-chloro | H | H | H | Cl |
| 656. | 5-fluoro-4-methoxy-3-fluoro | H | H | H | Cl |
| 657. | 5-fluoro-4-trifluoromethyl | H | H | H | Cl |
| 658. | 5-fluoro-3-methyl | H | H | H | Cl |
| 659. | 5-fluoro-3-trifluoromethyl | H | H | H | Cl |
| 660. | 5-nitro-3-methyl | H | H | H | Cl |
| 661. | 5-nitro | H | H | H | Cl |
| 662. | 5-methyl-4-fluoro | H | H | H | Cl |
| 663. | 5-methyl-4-methoxy | H | H | H | Cl |
| 664. | 5-trifluoromethoxy | H | H | H | Cl |
| 665. | 5-fluoro-3-nitro | H | H | H | Cl |
| 666. | 5-methyl-3-nitro | H | H | H | Cl |
| 667. | 5-methyl-4-methyl | H | H | H | Cl |
| 668. | 6-methyl-5-methyl-3-chloro | H | H | H | Cl |
| 669. | 6-methyl-5-methyl-4-chloro | H | H | H | Cl |
| 670. | 5-methyl-3-methyl | H | H | H | Cl |
| 671. | 6-fluoro-4-fluoro-3-fluoro | H | H | H | Cl |
| 672. | 5-fluoro-4-chloro-3-chloro | H | H | H | Cl |
| 673. | 4-methyl-3-methoxycarbonyl | H | H | H | Cl |
| 674. | 5-trifluoromethyl-3-chloro | H | H | H | Cl |
| 675. | 5-trifluoromethyl | H | H | H | Cl |
| 676. | 5-trifluoromethyl-3-nitro | H | H | H | Cl |
| 677. | 4,5-difluoromethylenedioxy | H | H | H | Cl |
| 678. | 4-trifluoromethoxy | H | H | H | Cl |
| 679. | 5-chloro-3-trifluoromethyl | H | H | H | Cl |
| 680. | 4-methyl | H | H | H | Cl |
| 681. | 4-cyano | H | H | H | Cl |

B. Formulation Examples
a) A dusting product is obtained by mixing 10 parts by weight of a compound of the formula (I) and/or a salt thereof and 90 parts by weight of talc as an inert substance, and comminuting the mixture in a hammer mill.
b) A readily water-dispersible wettable powder is obtained by mixing 25 parts by weight of a compound of the formula (I) and/or salts thereof, 64 parts by weight of kaolin-containing quartz as an inert substance, 10 parts by weight of potassium lignosulfonate and 1 part by weight of sodium oleylmethyltaurate as a wetting agent and dispersant, and grinding the mixture in a pinned-disk mill.
c) A readily water-dispersible dispersion concentrate is obtained by mixing parts by weight of a compound of the formula (I) and/or salts thereof with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.), and grinding the mixture in a ball mill to a fineness of below 5 microns.
d) An emulsifiable concentrate is obtained from 15 parts by weight of a compound of the formula (I) and/or salts thereof, 75 parts by weight of cyclohexanone as a solvent and 10 parts by weight of ethoxylated nonylphenol as an emulsifier.
e) Water-dispersible granules are obtained by mixing
  75 parts by weight of a compound of the formula (I) and/or salts thereof,
  10 parts by weight of calcium lignosulfonate,
  5 parts by weight of sodium laurylsulfate,
  3 parts by weight of polyvinyl alcohol and
  7 parts by weight of kaolin,
  grinding the mixture in a pinned-disk mill and granulating the powder in a fluidized bed by spraying on water as a granulating liquid.
f) Water-dispersible granules are also obtained by homogenizing and precomminuting
  25 parts by weight of a compound of the formula (I) and/or salts thereof,
  5 parts by weight of sodium 2,2'-dinaphthylmethane-6,6'-disulfonate,
  2 parts by weight of sodium oleylmethyltaurate,
  1 part by weight of polyvinyl alcohol,
  17 parts by weight of calcium carbonate and
  50 parts by weight of water
  in a colloid mill, then grinding the mixture in a bead mill and atomizing and drying the resulting suspension in a spray tower by means of a one-substance nozzle.

C. Biological Examples

Post-emergence herbicidal effect and crop plant compatibility

Seeds of monocotyledonous and dicotyledonous weed and crop plants are placed in sandy loam in wood-fibre pots, covered with soil and cultivated in a greenhouse under good growth conditions. 2 to 3 weeks after sowing, the test plants are treated at the one-leaf stage. The inventive compounds, formulated in the form of wettable powders (WP) or as emulsion concentrates (EC), are then sprayed onto the green parts of the plants as an aqueous suspension or emulsion at a water application rate of 600 to 800 l/ha (converted) with addition of 0.2% by weight of wetting agent. After the test plants have been left to stand in the greenhouse under optimal growth conditions for about 3 weeks, the action of the formulations is scored visually in comparison to untreated controls (herbicidal action in percent (%): 100% action=the plants have died, 0% action=like control plants).

As the results show, inventive compounds have good herbicidal post-emergence efficacy against a broad spectrum of gramineous and broadleaf weeds. For example, compounds no. 58 and other compounds from tables 1-3 have very good herbicidal action of at least 90% against weed plants such as *Amaranthus retroflexus, Matricaria inodora, Pharbitis (Ipomoea) purpurea, Polygonum (Fallopia) convolvulus, Stellaria media, Veronica persica* and *Viola tricolor* when applied post-emergence at an application rate of 1.28 kg or less active substance per hectare. At the same time, inventive compounds leave Gramineae crops such as barley, wheat, rye, millet/sorghum, corn or rice undamaged when applied post-emergence, even at high active ingredient dosages. In addition, some substances are also harmless to dicotyledonous crops such as soya, cotton, oilseed rape, sugar beet or potatoes. Some of the inventive compounds exhibit high selectivity and are therefore suitable for controlling unwanted vegetation in agricultural crops by the post-emergence method.

Pre-emergence Herbicidal Effect and Crop Plant Compatibility

Seeds of monocotyledonous and dicotyledonous weed plants and crop plants are placed in wood-fibre pots in sandy loam and covered with soil. The inventive compounds, formulated in the form of wettable powders (WP) or as emulsion concentrates (EC), are then applied to the surface of the covering soil as an aqueous suspension or emulsion at a water application rate of 600 to 800 l/ha (converted) with addition of 0.2% wetting agent. After the treatment, the pots are placed in a greenhouse and kept under good growth conditions for the test plants. The damage to the test plants is assessed visually after a test period of 3 weeks by comparison with untreated controls (herbicidal activity in percent (%): 100% action=the plants have died, 0% action=like control plants).

As the results show, inventive compounds have good herbicidal pre-emergence efficacy against a broad spectrum of gramineous and broadleaf weeds. For example, compounds no. 58 and other compounds from tables 1-3 have very good herbicidal action of at least 90% against weed plants such as *Amaranthus retroflexus, Polygonum* (Fallopia) *convolvulus* and *Viola tricolor* when applied pre-emergence at an application rate of 1.28 kg of active substance per hectare. At the same time, inventive compounds leave dicotyledonous crops such as soya, cotton, oilseed rape, sugar beet or potatoes undamaged when applied pre-emergence, even at high active ingredient dosages. In addition, some substances are also harmless to Gramineae crops such as barley, wheat, rye, millet/sorghum, corn or rice. Some of the inventive compounds exhibit high selectivity and are therefore suitable for controlling unwanted vegetation in agricultural crops by the pre-emergence method.

The invention claimed is:
1. A 6-(2-aminophenyl)picolinate of formula (I)

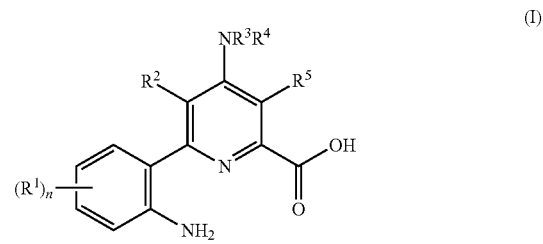

or an agrochemically suitable carboxylic derivative thereof selected from salts, esters, acyl hydrazides, imidates, thioimidates, amidines, amides, orthoesters, acyl cyanides, acyl halides, thioesters, thionoesters, dithiol esters, and nitrile or an agrochemically suitable amino derivative selected from salts, N-oxides, amides, sulfonanamides, and carbamates,
in which
n is 0, 1, 2, 3, or 4;
$R^1$ is selected from the group consisting of hydrogen, halogen, cyano, nitro, amino, hydroxyl, $(C_1$-$C_6)$alkyl, $(C_1$-$C_6)$haloalkyl, $(C_1$-$C_4)$hydroxyalkyl, $(C_2$-$C_6)$alkoxyalkyl, $(C_2$-$C_6)$halo-alkoxyalkyl, $(C_2$-$C_6)$alkenyl, $(C_2$-$C_6)$haloalkenyl, $(C_2$-$C_6)$alkynyl, $(C_3$-$C_6)$haloalkynyl, $(C_1$-$C_6)$alkoxy, $(C_1$-$C_6)$haloalkoxy, $(C_2$-$C_6)$alkenyloxy, $(C_2$-$C_6)$haloalkenyloxy, $(C_2$-$C_6)$-alkynyloxy, $(C_3$-$C_6)$haloalkynyloxy, $(C_1$-$C_6)$alkylthio, $(C_2$-$C_6)$alkylthioalkyl, $(C_1$-$C_6)$halo-alkylthio, $(C_1$-$C_6)$alkylsulfinyl, $(C_1$-$C_6)$haloalkylsulfinyl, $(C_1$-$C_6)$alkylsulfonyl, $(C_1$-$C_6)$-haloalkylsulfonyl, $(C_2$-$C_6)$alkenylthio, $(C_2$-$C_6)$haloalkenylthio, $(C_2$-$C_6)$alkenylsulfinyl, $(C_2$-$C_6)$haloalkenylsulfinyl, $(C_2$-$C_6)$alkenylsulfonyl, $(C_2$-$C_6)$haloalkenylsulfonyl, $(C_2$-$C_6)$-alkynylthio, $(C_3$-$C_6)$haloalkynylthio, $(C_3$-$C_6)$alkynylsulfinyl, $(C_3$-$C_6)$haloalkynylsulfinyl, $(C_3$-$C_6)$alkynylsulfonyl, $(C_3$-$C_6)$haloalkynylsulfonyl, $(C_1$-$C_6)$alkylamino, $(C_2$-$C_6)$dialkyl-amino, $(C_2$-$C_6)$alkylaminoalkyl, $(C_2$-$C_6)$alkylcarbonyl, $(C_2$-$C_6)$alkoxycarbonyl, $(C_2$-$C_6)$-aminocarbonyl, $(C_2$-$C_6)$alkylaminocarbonyl, $(C_3$-$C_8)$dialkylaminocarbonyl, $(C_3$-$C_6)$-trialkylsilyl, phenyl, phenoxy and 5- or 6-membered heteroaromatic rings, where each phenyl ring, phenoxy ring or 5- or 6-membered heteroaromatic ring may optionally be substituted by one to three $R^{25}$ radicals; or where two adjacent $R^1$ radicals may together form an —OCH$_2$O—, —CH$_2$CH$_2$O—, —OCH$_2$CH$_2$O—, —OCH(CH$_3$)O—, —OC(CH$_3$)$_2$O—,—OCF$_2$O—, —CF$_2$CF$_2$O—,— OCF$_2$CF$_2$O— or —CH═CH—CH═CH— group;
$R^2$ is hydrogen, halogen, cyano, nitro, $(C_1$-$C_6)$alkyl, $(C_1$-$C_6)$haloalkyl, $(C_1$-$C_6)$alkoxy, $(C_1$-$C_6)$-alkylamino, $(C_1$-$C_6)$dialkylamino, $(C_1$-$C_6)$thioalkoxy, $(C_2$-$C_6)$alkenyl, $(C_2$-$C_6)$haloalkenyl, $(C_2$-$C_6)$alkynyl;
$R^3$ is hydrogen, $(C_1$-$C_4)$alkyl optionally substituted by one or two $R^6$ radicals, $(C_2$-$C_4)$alkenyl optionally substituted by one or two $R^7$ radicals, or $(C_2$-$C_4)$alkynyl optionally substituted by one or two $R^8$ radicals; or $R^3$ is $C(═O)R^9$, $NO_2$, $OR^{10}$, $S(O)_2R^{11}$, $N(R^{12})R^{13}$ or $N═C(R^{14})R^{15}$;
$R^4$ is hydrogen, $(C_1$-$C_4)$alkyl optionally substituted by one or two $R^6$ radicals, or $C(═O)R^9$; or
$R^3$ and $R^4$ together form a —(CH$_2)_4$—, —(CH$_2)_5$—, —CH$_2$CH═CHCH$_2$— or —(CH$_2)_2$O(CH$_2)_2$— group which is optionally substituted by one or two $R^{16}$ radicals; or $R^3$ and $R^4$ together form a ═C($R^{17}$)N($R^{18}$)$R^{19}$ or ═C($R^{20}$)OR$^{21}$ group;
$R^5$ is hydrogen, halogen, cyano, nitro, formyl, $(C_1$-$C_6)$alkyl, $(C_2$-$C_6)$alkenyl, $(C_2$-$C_6)$alkynyl, $(C_1$-$C_6)$haloalkyl, $(C_2$-$C_6)$haloalkenyl, $(C_1$-$C_6)$alkoxy, $(C_1$-$C_6)$thioalkoxy, $(C_2$-$C_6)$alkoxy-alkyl, $(C_2$-$C_6)$thioalkoxyalkyl;
$R^6$, $R^7$ and $R^8$ are each independently selected from halogen, $(C_1$-$C_3)$alkoxy, $(C_1$-$C_3)$haloalkoxy, $(C_1$-$C_3)$alkylthio, $(C_1$-$C_3)$haloalkylthio, amino, $(C_1$-$C_3)$alkylamino, $(C_2$-$C_4)$dialkylamino and $(C_2$-$C_4)$ alkoxycarbonyl;
$R^9$ is hydrogen, $(C_1$-$C_4)$alkyl, $(C_1$-$C_4)$haloalkyl, $(C_1$-$C_4)$alkoxy, phenyl, phenoxy, benzyl or benzyloxy;
$R^{10}$ is hydrogen, $(C_1$-$C_4)$alkyl, $(C_1$-$C_3)$haloalkyl or CHR$^{22}$C(O)OR$^{23}$;
$R^{11}$ is $(C_1$-$C_4)$alkyl, $(C_1$-$C_4)$haloalkyl or phenyl optionally substituted by one, two or three radicals selected independently from CH$_3$, Cl and OCH$_3$;
$R^{12}$ is hydrogen, $(C_1$-$C_4)$alkyl or C(═O)$R^{24}$;
$R^{13}$ is hydrogen or $(C_1$-$C_4)$alkyl;

$R^{14}$ is hydrogen, $(C_1$-$C_4)$alkyl or phenyl optionally substituted by one, two or three radicals selected independently from CH$_3$, Cl or OCH$_3$;
$R^{15}$ is hydrogen or $(C_1$-$C_4)$alkyl; or $R^{14}$ and $R^{15}$ together form a —(CH$_2)_4$— or —(CH$_2)_5$— group;
$R^{16}$ is independently halogen, $(C_1$-$C_3)$alkyl, $(C_1$-$C_3)$alkoxy, $(C_1$-$C_3)$haloalkoxy, $(C_1$-$C_3)$alkylthio, $(C_1$-$C_3)$haloalkylthio, amino, $(C_1$-$C_3)$alkylamino, $(C_2$-$C_4)$dialkylamino or $(C_2$-$C_4)$alkoxycarbonyl;
$R^{17}$ is hydrogen or $(C_1$-$C_4)$alkyl;
$R^{18}$ and $R^{19}$ are each independently selected from hydrogen and $(C_1$-$C_4)$alkyl; or $R^{18}$ and $R^{19}$ together form a —(CH$_2)_4$—, —(CH$_2)_5$—, —CH$_2$CH═CHCH$_2$— or —(CH$_2)_2$O(CH$_2)_2$— group;
$R^{20}$ is hydrogen or $(C_1$-$C_4)$alkyl;
$R^{21}$ is $(C_1$-$C_4)$alkyl;
$R^{22}$ is hydrogen, $(C_1$-$C_4)$alkyl, $(C_1$-$C_3)$haloalkyl, $(C_1$-$C_4)$alkoxy, phenyl, phenoxy or benzyloxy;
$R^{23}$ is hydrogen, $(C_1$-$C_4)$alkyl or $(C_1$-$C_4)$alkoxy;
$R^{24}$ is hydrogen, $C_1$-$C_4$ alkyl or benzyl; and
$R^{25}$ is, optionally independently of further $R^{25}$ radicals, selected from halogen, cyano, nitro, $(C_1$-$C_6)$alkyl, $(C_1$-$C_6)$haloalkyl, $(C_2$-$C_4)$alkenyl, $(C_2$-$C_4)$haloalkenyl, $(C_3$-$C_4)$alkynyl, $(C_3$-$C_4)$haloalkynyl, $(C_1$-$C_4)$alkoxy, $(C_1$-$C_4)$haloalkoxy, $(C_1$-$C_4)$alkylthio, $(C_1$-$C_4)$haloalkylthio, $(C_1$-$C_4)$alkylsulfinyl, $(C_1$-$C_4)$alkylsulfonyl, $(C_1$-$C_4)$alkylamino, $(C_2$-$C_8)$dialkylamino, $(C_2$-$C_4)$alkylcarbonyl, $(C_2$-$C_6)$alkoxycarbonyl, $(C_2$-$C_6)$alkylaminocarbonyl, $(C_3$-$C_8)$dialkylaminocarbonyl and $(C_3$-$C_6)$ trialkylsilyl.

2. A compound of at least one of the formulae (I-a) to (I-c)

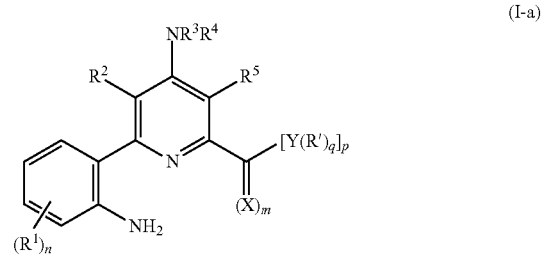

(I-a)

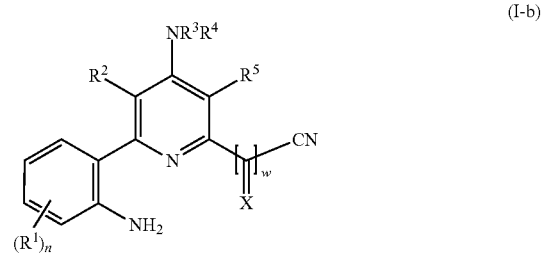

(I-b)

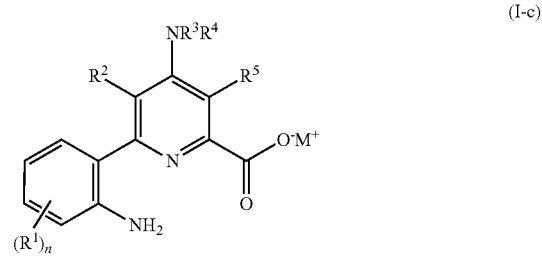

(I-c)

where
(A) the radicals in formula (I-a) are each defined as follows:
X is selected from the group consisting of O, S, NH and NR" where R" is a $(C_1$-$C_4)$alkyl group;

m is 0 or 1;

Y is selected from the group consisting of halogen, O, S and N;

q is 0, 1 or 2;

p is 1, 2 or 3;

R' is selected from the group consisting of hydrogen, halogen, $(C_1\text{-}C_4)$alkyl, $(C_1\text{-}C_4)$haloalkyl, $(C_2\text{-}C_4)$alkoxyalkyl, $(C_2\text{-}C_4)$alkylthioalkyl, $(C_2\text{-}C_4)$alkenyl, oxiranyl, $(C_1\text{-}C_4)$alkyloxiranyl, oxiranyl-$(C_1\text{-}C_4)$alkyl, $(C_2\text{-}C_4)$haloalkenyl, 2-halooxiranyl, 3-halooxiranyl, 2,3-dihalooxiranyl, $(C_3\text{-}C_6)$alkoxyalkenyl, $(C_3\text{-}C_6)$alkylthioalkenyl, $(C_2\text{-}C_4)$alkynyl, $(C_2\text{-}C_4)$haloalkynyl, formyl, $(C_2\text{-}C_4)$-alkylcarbonyl, and $(C_2\text{-}C_4)$haloalkylcarbonyl provided that Y is not halogen, where n, $R^1$, $R^2$, $R^3$, $R^4$, and $R^5$ are as defined below;

(B) the radicals in formula (I-b) are each defined as follows:

X is selected from the group consisting of O and S;

w is 0 or 1;

where n, $R^1$, $R^2$, $R^3$, $R^4$, and $R^5$ each are as defined below;

(C) $M^{30}$ in formula (I-c) is a cation:

where n, $R^1$, $R^2$, $R^3$, $R^4$, and $R^5$ each are as defined below;

n is 0, 1, 2, 3, or 4;

$R^1$ is selected from the group consisting of hydrogen, halogen, cyano, nitro, amino, hydroxyl, $(C_1\text{-}C_6)$alkyl, $(C_1\text{-}C_6)$haloalkyl, $(C_1\text{-}C_4)$hydroxyalkyl, $(C_2\text{-}C_6)$alkoxyalkyl, $(C_2\text{-}C_6)$halo-alkoxyalkyl, $(C_2\text{-}C_6)$alkenyl, $(C_2\text{-}C_6)$haloalkenyl, $(C_2\text{-}C_6)$alkynyl, $(C_3\text{-}C_6)$haloalkynyl, $(C_1\text{-}C_6)$alkoxy, $(C_1\text{-}C_6$haloalkoxy, $(C_2\text{-}C_6)$alkenyloxy, $(C_2\text{-}C_6)$haloalkenyloxy, $(C_2\text{-}C_6)$-alkynyloxy, $(C_3\text{-}C_6)$haloalkynyloxy, $(C_1\text{-}C_6)$alkylthio, $(C_2\text{-}C_6)$alkylthioalkyl, $(C_1\text{-}C_6)$halo-alkylthio, $(C_1\text{-}C_6)$alkylsulfinyl, $(C_1\text{-}C_6)$haloalkylsulfinyl, $(C_1\text{-}C_6)$alkylsulfonyl, $(C_1\text{-}C_6)$halo-alkylsulfonyl, $(C_2\text{-}C_6)$alkenylthio, $(C_2\text{-}C_6)$haloalkenylthio, $(C_2\text{-}C_6)$alkenylsulfinyl, $(C_2\text{-}C_6)$-haloalkenylsulfinyl, $(C_2\text{-}C_6)$alkenylsulfonyl, $(C_2\text{-}C_6)$haloalkenylsulfonyl, $(C_2\text{-}C_6)$alkynyl-thio, $(C_3\text{-}C_6)$haloalkynylthio, $(C_3\text{-}C_6)$alkynylsulfinyl, $(C_3\text{-}C_6)$haloalkynylsulfinyl, $(C_3\text{-}C_6)$alkynylsulfonyl, $(C_3\text{-}C_6)$haloalkynylsulfonyl, $(C_1\text{-}C_6)$alkylamino, $(C_2\text{-}C_6)$dialkylamino, $(C_2\text{-}C_6)$alkylaminoalkyl, $(C_2\text{-}C_6)$alkylcarbonyl, $(C_2\text{-}C_6)$alkoxycarbonyl, $(C_2\text{-}C_6)$amino-carbonyl, $(C_2\text{-}C_6)$alkylaminocarbonyl, $(C_3\text{-}C_8)$dialkylaminocarbonyl, $(C_3\text{-}C_6)$trialkylsilyl, phenyl, phenoxy and 5- or 6-membered heteroaromatic rings, where each phenyl ring, phenoxy ring or 5- or 6-membered heteroaromatic ring may optionally be substituted by one to three $R^{25}$ radicals; or where two adjacent $R^1$ radicals may together form an —OCH$_2$O—, —CH$_2$CH$_2$O—, —OCH$_2$CH$_2$O—, —OCH(CH$_3$)O—, —OC(CH$_3$)$_2$O—, —OCF$_2$O—, —CF$_2$CF$_2$O—, —OCF$_2$CF$_2$O— or —CH=CH—CH=CH— group;

$R^2$ is hydrogen, halogen, cyano, nitro, $(C_1\text{-}C_6)$alkyl, $(C_1\text{-}C_6)$haloalkyl, $(C_1\text{-}C_6)$alkoxy, $(C_1\text{-}C_6)$alkylamino, $(C_1\text{-}C_6)$dialkylamino, $(C_1\text{-}C_6)$thioalkoxy, $(C_2\text{-}C_6)$alkenyl, $(C_2\text{-}C_6)$-haloalkenyl, $(C_2\text{-}C_6)$alkynyl;

$R^3$ is hydrogen, $(C_1\text{-}C_4)$alkyl optionally substituted by one or two $R^6$ radicals, $(C_2\text{-}C_4)$alkenyl optionally substituted by one or two $R^7$ radicals, or $(C_2\text{-}C_4)$alkynyl optionally substituted by one or two $R^8$ radicals; or $R^3$ is C(=O)$R^9$, NO$_2$, OR$^{10}$, S(O)$_2$R$^{11}$, N(R$^{12}$)R$^{13}$ or N=C(R$^{14}$)R$^{15}$;

$R^4$ is hydrogen, $(C_1\text{-}C_4)$alkyl optionally substituted by one or two $R^6$ radicals, or C(=O)$R^9$; or $R^3$ and $R^4$ together form a —(CH$_2$)$_4$—, —(CH$_2$)$_5$—, —CH$_2$CH=CHCH$_2$— or —(CH$_2$)$_2$O (CH$_2$)$_2$— group which is optionally substituted by one or two $R^{16}$ radicals; or $R^3$ and $R^4$ together form a =C(R$^{17}$)N(R$^{18}$)R$^{19}$ or =C(R$^{20}$)OR$^{21}$ group;

$R^5$ is hydrogen, halogen, cyano, nitro, formyl, $(C_1\text{-}C_6)$alkyl, $(C_2\text{-}C_6)$alkenyl, $(C_2\text{-}C_6)$alkynyl, $(C_1\text{-}C_6)$haloalkyl, $(C_2\text{-}C_6)$haloalkenyl, $(C_1\text{-}C_6)$alkoxy, $(C_1\text{-}C_6)$thioalkoxy, $(C_2\text{-}C_6)$alkoxy-alkyl, $(C_2\text{-}C_6)$thioalkoxyalkyl;

$R^6$, $R^7$ and $R^8$ are each independently selected from halogen, $(C_1\text{-}C_3)$alkoxy, $(C_1\text{-}C_3)$haloalkoxy, $(C_1\text{-}C_3)$alkylthio, $(C_1\text{-}C_3)$haloalkylthio, amino, $(C_1\text{-}C_3)$alkylamino, $(C_2\text{-}C_4)$dialkylamino and $(C_2\text{-}C_4)$alkoxycarbonyl;

$R^9$ is hydrogen, $(C_1\text{-}C_4)$alkyl, $(C_1\text{-}C_4)$haloalkyl, $(C_1\text{-}C_4)$alkoxy, phenyl, phenoxy, benzyl or benzyloxy;

$R^{10}$ is hydrogen, $(C_1\text{-}C_4)$alkyl, $(C_1\text{-}C_3)$haloalkyl or CHR$^{22}$C(O)OR$^{23}$;

$R^{11}$ is $(C_1\text{-}C_4)$alkyl, $(C_1\text{-}C_4)$haloalkyl or phenyl optionally substituted by one, two or three radicals selected independently from CH$_3$, Cl and OCH$_3$;

$R^{12}$ is hydrogen, $(C_1\text{-}C_4)$alkyl or C(=O)$R^{24}$;

$R^{13}$ is hydrogen or $(C_1\text{-}C_4)$alkyl;

$R^{14}$ is hydrogen, $(C_1\text{-}C_4)$alkyl or phenyl optionally substituted by one, two or three radicals selected independently from CH$_3$, Cl or OCH$_3$;

$R^{15}$ is hydrogen or $(C_1\text{-}C_4)$alkyl; or $R^{14}$ and $R^{15}$ together form a —(CH$_2$)$_4$— or —(CH$_2$)$_5$— group;

$R^{16}$ is independently halogen, $(C_1\text{-}C_3)$alkyl, $(C_1\text{-}C_3)$alkoxy, $(C_1\text{-}C_3)$haloalkoxy, $(C_1\text{-}C_3)$alkyl-thio, $(C_1\text{-}C_3)$haloalkylthio, amino, $(C_1\text{-}C_3)$alkylamino, $(C_2\text{-}C_4)$dialkylamino or $(C_2\text{-}C_4)$-alkoxycarbonyl;

$R^{17}$ is hydrogen or $(C_1\text{-}C_4)$alkyl;

$R^{18}$ and $R^{19}$ are each independently selected from hydrogen and $(C_1\text{-}C_4)$alkyl; or $R^{18}$ and $R^{19}$ together form a —(CH$_2$)$_4$—, —(CH$_2$)$_5$—, —CH$_2$CH=CHCH$_2$— or —(CH$_2$)$_2$O(CH$_2$)$_2$— group;

$R^{20}$ is hydrogen or $(C_1\text{-}C_4)$alkyl;

$R^{21}$ is $(C_1\text{-}C_4)$alkyl;

$R^{22}$ is hydrogen, $(C_1\text{-}C_4)$alkyl, $(C_1\text{-}C_3)$haloalkyl, $(C_1\text{-}C_4)$alkoxy, phenyl, phenoxy or benzyloxy;

$R^{23}$ is hydrogen, $(C_1\text{-}C_4)$alkyl or $(C_1\text{-}C_4)$alkoxy;

$R^{24}$ is hydrogen, $C_1$-$C_4$ alkyl or benzyl; and $R^{25}$ is, optionally independently of further $R^{25}$ radicals, selected from the group consisting of halogen, cyano, nitro, $(C_1\text{-}C_6)$alkyl, $(C_1\text{-}C_6)$haloalkyl, $(C_2\text{-}C_4)$alkenyl, $(C_2\text{-}C_4)$haloalkenyl, $(C_3\text{-}C_4)$alkynyl, $(C_3\text{-}C_4)$haloalkynyl, $(C_1\text{-}C_4)$alkoxy, $(C_1\text{-}C_4)$haloalkoxy, $(C_1\text{-}C_4)$alkylthio, $(C_1\text{-}C_4)$haloalkylthio, $(C_1\text{-}C_4)$alkylsulfinyl, $(C_1\text{-}C_4)$alkylsulfonyl, $(C_1\text{-}C_4)$alkylamino, $(C_2\text{-}C_8)$dialkylamino, $(C_2\text{-}C_4)$alkylcarbonyl, $(C_2\text{-}C_6)$alkoxycarbonyl, $(C_2\text{-}C_6)$alkyl-aminocarbonyl, $(C_3\text{-}C_8)$dialkylaminocarbonyl and $(C_3\text{-}C_6)$trialkylsilyl.

3. The compound as claimed in claim 1, in which the radicals are each defined as follows:

n is 0, 1, 2, 3, or 4;

$R^1$ is, optionally independently of further $R^1$ radicals, selected from the group consisting of hydrogen, halogen, cyano, nitro, amino, $(C_1\text{-}C_6)$alkyl, $(C_1\text{-}C_6)$haloalkyl, $(C_2\text{-}C_6)$alkoxy-alkyl, $(C_2\text{-}C_6)$haloalkoxyalkyl, $(C_2\text{-}C_6)$alkenyl, $(C_2\text{-}C_6)$haloalkenyl, $(C_2\text{-}C_6)$alkynyl, $(C_1\text{-}C_6)$alkoxy, $(C_1\text{-}C_6)$haloalkoxy, $(C_2\text{-}C_6)$haloalkenyloxy, $(C_1\text{-}C_6)$alkylthio, $(C_2\text{-}C_6)$-alkylthioalkyl, $(C_1\text{-}C_6)$haloalkylthio, $(C_1\text{-}C_6)$alkylsulfonyl, $(C_1\text{-}C_6)$haloalkylsulfonyl, $(C_2\text{-}C_6)$alkenylthio, $(C_2\text{-}C_6)$haloalkenylthio, $(C_1\text{-}C_6)$alkylamino, $(C_2\text{-}C_6)$dialkylamino, $(C_2\text{-}C_6)$alkylaminoalkyl, $(C_2\text{-}C_6)$alkylcarbonyl, $(C_2\text{-}C_6)$alkoxycarbonyl, (C₂-C₆)amino-carbonyl, (C₂-C₆)alkylaminocarbonyl, (C₃-C₈)dialkylaminocarbonyl, or two adjacent R¹ radicals together form an —OCH₂O—, —CH₂CH₂O—, —OCH₂CH₂O—, —OCH(CH₃)O—, —OC(CH₃)₂O—, —OCF₂O—, —CF₂CF₂O—, —OCF₂CF₂O— or —CH=CH—CH=CH— group;

R² is hydrogen, halogen, cyano;

R³ is hydrogen, (C₁-C₄)alkyl, (C₂-C₄)alkenyl, (C₂-C₄)alkynyl or C(=O)R⁹, OR¹⁰,S(O)₂R¹¹, N(R¹²)R¹³ or N=C(R¹⁴)R¹⁵;

R⁴ is hydrogen, (C₁-C₄)alkyl optionally substituted by one or two R⁶ radicals, or C(=O)R⁹; or R³ and R⁴ together form a —(CH₂)₄—, —(CH₂)₅, —(CH₂)₂O (CH₂)— or =C(R¹⁷)N(R¹⁸)R¹⁹ group; each R⁶ radical, optionally independently of further R⁶ radicals, is selected from the group consisting of halogen, (C₁-C₃)alkoxy, (C₁-C₃)haloalkoxy, (C₁-C₃)alkylthio, (C₁-C₃)halo-alkylthio, amino, (C₁-C₃)alkylamino, (C₂-C₄)dialkylamino and (C₂-C₄)alkoxycarbonyl;

R⁵ is hydrogen, halogen, cyano;

R⁹ is, optionally independently of further R⁹ radicals, selected from the group consisting of hydrogen, (C₁-C₄)alkyl, (C₁-C₄)haloalkyl, (C₁-C₄)alkoxy, phenyl, phenoxy, benzyl and benzyloxy;

R¹⁰ is hydrogen, (C₁-C₄)alkyl or (C₁-C₃)haloalkyl;

R¹¹ is (C₁-C₄)alkyl or phenyl optionally substituted by one, two or three radicals selected independently from the group consisting of CH₃, Cl and OCH₃;

R¹² is hydrogen, (C₁-C₄)alkyl or C(=O)R²⁴;

R¹³ is hydrogen or (C₁-C₄)alkyl;

R¹⁴ is hydrogen or (C₁-C₄)alkyl;

R¹⁵ is hydrogen or (C₁-C₄)alkyl; or

R¹⁴ and R¹⁵ together form a —(CH₂)₄— or —(CH₂)₅— group;

R¹⁷ is hydrogen or (C₁-C₄)alkyl;

R¹⁸ and R¹⁹ are each independently hydrogen or (C₁-C₄) alkyl; or R¹⁸ and R¹⁹ together form a —(CH₂)₄—, —(CH₂)₅—, —CH₂CH=CHCH₂— or —(CH₂)₂O (CH₂)₂— group; and R²⁴ is hydrogen, (C₁-C₄) alkyl or benzyl.

4. The compound as claimed in claim 1, in which the radicals are each defined as follows:

n is 0, 1, 2, 3, or 4,

R¹ is, optionally independently of further R¹ radicals, selected from hydrogen, fluorine, chlorine, bromine, iodine, methyl, cyclopropyl, trifluoromethyl, methoxymethyl, methoxy, methylthio, methoxycarbonyl, dimethylamino;

R² is hydrogen, fluorine or chlorine;

R³ is hydrogen, methyl, ethyl or C(=O)CH₃ (acetyl);

R⁴ is hydrogen, methyl, ethyl or C(=O)CH₃ (acetyl); and

R⁵ is hydrogen, fluorine or chlorine.

5. A process for preparing a compound as claimed in claim 1 comprising (A) reacting a halogen compound of formula (II) where
R' is (C₁-C₁₂)alkyl or hydrogen,
n is 0, 1, 2, 3, or 4;
R¹ is selected from the group consisting of hydrogen, halogen, cyano, nitro, amino, hydroxyl, (C₁-C₆)alkyl, (C₁-C₆)haloalkyl, (C₁-C₄)hydroxyalkyl, (C₂-C₆)alkoxyalkyl, (C₂-C₆)haloalkoxyalkyl, (C₂-C₆)alkenyl, (C₂-C₆)haloalkenyl, (C₂-C₆)alkynyl, (C₃-C₆)haloalkynyl, (C₁-C₆)alkoxy, (C₁-C₆)haloalkoxy, (C₂-C₆)alkenyloxy, (C₂-C₆)-haloalkenyloxy, (C₂-C₆)alkynyloxy, (C₃-C₆)haloalkynyloxy, (C₁-C₆)alkylthio, (C₂-C₆)alkylthioalkyl, (C₁-C₆)haloalkylthio, (C₁-C₆)alkylsulfinyl, (C₁-C₆)haloalkyl-sulfinyl, (C₁-C₆)alkylsulfonyl, (C₁-C₆)haloalkylsulfonyl, (C₂-C₆)alkenylthio, (C₂-C₆)haloalkenylthio, (C₂-C₆)alkenylsulfinyl, (C₂-C₆)haloalkenylsulfinyl, (C₂-C₆)alkenylsulfonyl, (C₂-C₆)haloalkenylsulfonyl, (C₂-C₆)alkynylthio, (C₃-C₆)haloalkynylthio, (C₃-C₆)alkynylsulfinyl, (C₃-C₆)haloalkynylsulfinyl, (C₃-C₆)alkynylsulfonyl, (C₃-C₆)haloalkynylsulfonyl, (C₁-C₆)alkylamino, (C₂-C₆)dialkylamino, (C₂-C₆)alkylaminoalkyl, (C₂-C₆)alkylcarbonyl, (C₂-C₆)-alkoxycarbonyl, (C₂-C₆)aminocarbonyl, (C₂-C₆)alkylaminocarbonyl, (C₃-C₈)-dialkylaminocarbonyl, (C₃-C₆)trialkylsilyl, phenyl, phenoxy and 5- or 6-membered heteroaromatic rings, where each phenyl ring, phenoxy ring or 5- or 6-membered heteroaromatic ring may optionally be substituted by one to three R²⁵radicals; or where two adjacent R¹ radicals may together form an —OCH₂O—, —CH₂CH₂O—, —OCH₂CH₂O—, —OCH(CH₃)O—, —OC(CH₃)₂O—, —OCF₂O—, —CF₂CF₂O—, —OCF₂CF₂O— or —CH=CH—CH=CH— group;

R² is hydrogen, halogen, cyano, nitro, (C₁-C₆)alkyl, (C₁-C₆)haloalkyl, (C₁-C₆)alkoxy, (C₁-C₆)alkylamino, (C₁-C₆)dialkylamino, (C₁-C₆)thioalkoxy, (C₂-C₆)alkenyl, (C₂-C₆)haloalkenyl, (C₂-C₆)alkynyl;

R³ is hydrogen, (C₁-C₄)alkyl optionally substituted by one or two R⁶ radicals, (C₂-C₄)alkenyl optionally substituted by one or two R⁷ radicals, or (C₂-C₄)alkynyl optionally substituted by one or two R⁸ radicals; or R³ is C(=O)R⁹, NO₂, OR¹⁰,S(O)₂R¹¹, N(R¹²)R¹³ or N=C(R¹⁴)R¹⁵;

R⁴ is hydrogen, (C₁-C₄)alkyl optionally substituted by one or two R⁶ radicals, or C(=O)R⁹; or R³ and R⁴ together form a —(CH₂)₄—, —(CH₂)₅—, —CH₂CH=CHCH₂— or —(CH₂)₂O(CH₂)₂— group which is optionally substituted by one or two R¹⁶ radicals; or R³ and R⁴ together form a =C(R¹⁷)N(R¹⁸)R¹⁹ or =C(R²⁰)OR²¹ group;

R⁵ is hydrogen, halogen, cyano, nitro, formyl, (C₁-C₆)alkyl, (C₂-C₆)alkenyl, (C₂-C₆)-alkynyl, (C₁-C₆)haloalkyl, (C₂-C₆)haloalkenyl, (C₁-C₆)alkoxy, (C₁-C₆)thioalkoxy, (C₂-C₆)alkoxyalkyl, (C₂-C₆)thioalkoxyalkyl; and R⁶, R⁷ and R⁸ are each independently selected from halogen, (C₁-C₃)alkoxy, (C₁-C₃)halo-alkoxy, (C₁-C₃)alkylthio, (C₁-C₃)haloalkylthio, amino, (C₁-C₃)alkylamino, (C₂-C₄)dialkylamino and (C₂-C₄)alkoxycarbonyl;

with a boron compound of formula (III) where the Rˣ and Rʸ radicals are both hydrogen or where the Rˣ and Rʸ radicals are each independently (C₁-C₆)alkyl or (C₆-C₁₂)aryl or where Rˣ and Rʸ together with the boron atom to which they are bonded optionally also form cyclic structures, or with a trifluoroborate salt thereof in the presence of a palladium catalyst

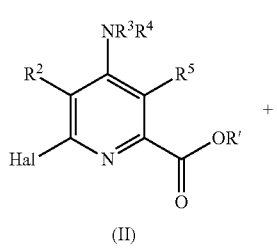

(II)

-continued

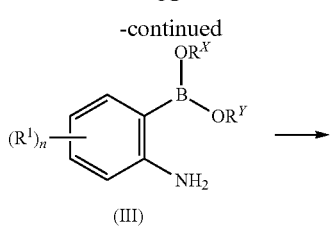

(III)

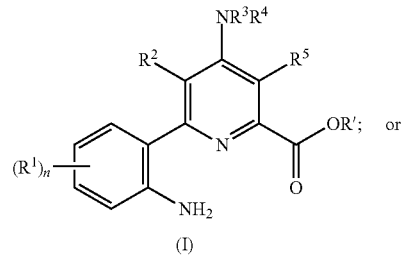

(I)

(B) reacting a tin compound of formula (V) where $R^5$ is $(C_1\text{-}C_6)$alkyl, $(C_1\text{-}C_6)$alkenyl or $(C_1C_6)$alkynyl with a halogenated compound of formula (I-1) where Hal is chlorine, bromine or iodine

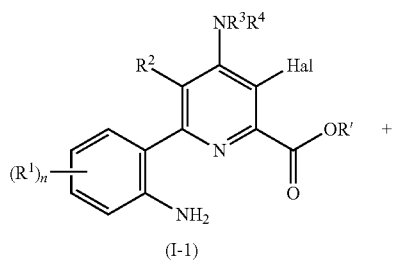

(I-1)

-continued $(n\text{-}Bu)_3Sn\text{---}R^5 \longrightarrow$ (V)

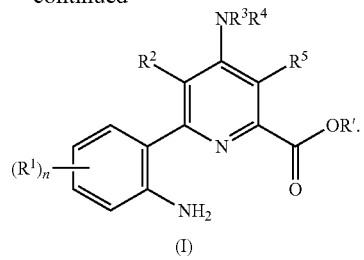

(I)

6. An agrochemical composition comprising a) at least one compound claim 1, and one or more b) auxiliaries and/or additives customary in crop protection.

7. An agrochemical composition comprising:
  a) at least one compound of claim 1,
  b) at least one active agrochemical ingredient other than component a), and optionally
  c) one or more auxiliaries and/or additives customary in crop protection.

8. A method for controlling an unwanted plant and/or for regulating growth of a plant, comprising applying an effective amount of at least one compound as defined in claim 1, to a plant, seed and/or an area on which a plant grows.

9. The compound as defined in claim 1, capable of being used as a herbicide and/or plant growth regulator.

10. The compound capable of being used as claimed in claim 9, wherein said compound is capable of being used to control a weed plant and/or to regulate growth in a plant crop.

11. The compound capable of being used as claimed in claim 10, wherein said crop plant comprises a transgenic or nontransgenic crop plant.

12. A crop plant which has been treated with a compound of claim 1.

* * * * *